(12) United States Patent
Orentas et al.

(10) Patent No.: US 10,421,810 B2
(45) Date of Patent: Sep. 24, 2019

(54) CHIMERIC ANTIGEN RECEPTORS AND METHODS OF USE

(71) Applicant: MILTENYI BIOTEC TECHNOLOGY, INC., Gaithersburg, MD (US)

(72) Inventors: Rimas Orentas, Washington, DC (US); Dina Schneider, Potomac, MD (US); Boro Dropulic, Ellicott City, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 0 days.

(21) Appl. No.: 15/767,076

(22) PCT Filed: Oct. 7, 2016

(86) PCT No.: PCT/US2016/056073
§ 371 (c)(1),
(2) Date: Apr. 9, 2018

(87) PCT Pub. No.: WO2017/062820
PCT Pub. Date: Apr. 13, 2017

(65) Prior Publication Data
US 2018/0305452 A1 Oct. 25, 2018

Related U.S. Application Data

(60) Provisional application No. 62/239,509, filed on Oct. 9, 2015.

(51) Int. Cl.
| | |
|---|---|
| *A61K 39/395* | (2006.01) |
| *C07K 16/28* | (2006.01) |
| *C07K 14/705* | (2006.01) |
| *C07K 14/725* | (2006.01) |
| *C07K 19/00* | (2006.01) |
| *A61K 35/17* | (2015.01) |
| *C12N 15/87* | (2006.01) |
| *A61P 35/00* | (2006.01) |
| *A61K 39/00* | (2006.01) |

(52) U.S. Cl.
CPC .......... *C07K 16/2803* (2013.01); *A61K 35/17* (2013.01); *C07K 14/705* (2013.01); *C07K 14/7051* (2013.01); *C07K 14/70578* (2013.01); *C07K 19/00* (2013.01); *C12N 15/87* (2013.01); *A61K 2039/505* (2013.01); *A61P 35/00* (2018.01); *C07K 2317/622* (2013.01); *C07K 2319/00* (2013.01); *C07K 2319/02* (2013.01); *C07K 2319/03* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 2014/0134720 A1* | 5/2014 | Stauss | C07K 14/7051 435/328 |
| 2014/0286973 A1 | 9/2014 | Powell | |
| 2015/0283178 A1 | 10/2015 | June et al. | |

FOREIGN PATENT DOCUMENTS

| | | |
|---|---|---|
| WO | WO 2014/130635 | 8/2014 |
| WO | WO 2015/090230 | 1/2015 |

OTHER PUBLICATIONS

International Search Report and Written Opinion in PCT/US2016/056073, dated Jan. 5, 2017 (11 pages).

* cited by examiner

*Primary Examiner* — Michael D Pak
(74) *Attorney, Agent, or Firm* — Serge Sira, Esq.; Fish & Richardson P.C.

(57) ABSTRACT

Chimeric antigen receptors containing tumor necrosis factor receptor superfamily member transmembrane domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

19 Claims, 16 Drawing Sheets

Specification includes a Sequence Listing.

```
Feature:            1 2 3       456 789
CD8:       CDIYIWAPLAGTCGV-LLLSLVILYCKR
CD4:       PM-AL-IVLGGVAGLLLFIGLGIFFCVRC
TNFRSF16:  TTDNL-IPVYCSILAAVVVGLVAYIAFKR
TNFRSF19:  TA--L-AAVICSALATVLLALLILCVIYC
```

FIGURE 2

I. SP-CD19binder-CD8link-CD8tm-signaling (LTG1494)

Amino acid sequence

*MLLLVTSLLLCELPHPAFLLIP*DTDIQMTQTTSSLSASLGD
RVTISCRASQDISKYLNWYQQKPDGTVKLLIYHTSRLHSGVPSRFSGSGS
GTDYSLTISNLEQEDIATYFCQQGNTLPYTFGGGTKLEITGSTSGSGKPG
SGEGSTKGEVKLQESGPGLVAPSQSLSVTCTVSGVSLPDYGVSWIRQPPR
KGLEWLGVIWGSETTYYNSALKSRLTIIKDNSKSQVFLKMNSLQTDDTAIYYC
AKHYYYGGSYAMDYWGQGTSVTVSSAAATTTPAPRPPTPAPTIASQPLSLRPE
ACRPAAGGAVHTRGLDF<u>ACDIYIWAPLAGTCGVLLLSLVITLY</u>CKRGRKKLLY
IFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEA
YSEIGMKGERRRGKGHDGLYQGLSTATKDTYDALHMQALPPR

Nucleic acid sequence (DNA)

atgctgctgctggtgaccagcctgctgctgtgcgaactgccgcatccggcgtttctgctg
attccggataccgatattcagatgacccagaccaccagcagcctgagcgcgagcctgggc
gatcgcgtgaccattagctgccgcgcgagccaggatattagcaaatatctgaactggtat
cagcagaaaccggatggcaccgtgaaactgctgatttatcataccagccgcctgcatagc
ggcgtgccgagccgctttagcggcagcggcagcggcaccgattatagcctgaccattagc
aacctggaacaggaagatattgcgacctattttgccagcagggcaacaccctgccgtat
acctttggcggcggcaccaaactggaaattaccggcagcaccagcggcagcggcaaaccg
ggcagcggcgaaggcagcaccaaaggcgaagtgaaactgcaggaaagcggcccgggcctg
gtggcgccgagccagagcctgagcgtgacctgcaccgtgagcggcgtgagcctgccggat
tatggcgtgagctggattcgccagccgccgcgcaaaggcctggaatggctgggcgtgatt
tggggcagcgaaaccacctattataacagcgcgctgaaaagccgcctgaccattattaaa
gataacagcaaaagccaggtgtttctgaaaatgaacagcctgcagaccgatgataccgcg
atttattattgcgcgaaacattattattatggcggcagctatgcgatggattattgggc
cagggcaccagcgtgaccgtgagcagcgcggcggcgaccaccaccccggcgccgcgcccg
ccgaccccggcgccgaccattgcgagccagccgctgagcctgcgccccggaagcgtgccgc
ccggcggcgggcggcgcggtgcatacccgcggcctggattttgcgtgcgatatttatatt
tgggcgccgctggcgggcacctgcggcgtgctgctgctgagcctggtgattaccctgtat
tgcaaacgcggccgcaaaaaactgctgtatatttttaaacagccgtttatgcgcccggtg
cagaccacccaggaagaagatggctgcagctgccgctttccggaagaagaagaaggcggc
tgcgaactgcgcgtgaaatttagccgcagcgcggatgcgccggcgtatcagcagggccag
aaccagctgtataacgaactgaacctgggccgccgcgaagaatatgatgtgctggataaa
cgccgcggccgcgatccggaaatgggcggcaaaccgcgccgcaaaaacccgcaggaaggc
ctgtataacgaactgcagaaagataaaatggcggaagcgtatagcgaaattggcatgaaa
ggcgaacgccgccgcggcaaaggccatgatggcctgtatcagggcctgagcaccgcgacc
aaagatacctatgatgcgctgcatatgcaggcgctgccgccgcgc

FIGURE 3A

II. SP-CD19binder-CD8link-CD8tm-signals (LTI re-engineered) (LTG1538)

*MLLLVTSLLLCELPHPAFLLIPDIQMTQTTSSLSASLGD*
*RVTISCRASQDISKYLNWYQQKPDGTVKLLIYHTSRLHSGVPSRFSGSGS*
*GTDYSLTISNLEQEDIATYFCQQGNTLPYTFGGGTKLEITGGGGSGGGGS*
*GGGGSEVKLQESGPGLVAPSQSLSVTCTVSGVSLPDYGVSWIRQPPRKGL*
*EWLGVIWGSETTYYNSALKSRLTIIKDNSKSQVFLKMNSLQTDDTAIYYC*
*AKHYYYGGSYAMDYWGQGTSVTVSS*__AAA__TTTPAPRPPTPAPTIASQPLSLRPE
ACRPAAGGAVHTRGLDF__ACDIYIWAPLAGTCGVLLLSLVITLY__CKRGRKKLLY
IFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEA
YSEIGMKGERRRGKGHDGLYQGLSTATKDTYDALHMQALPPR

```
atgctgctgctggtgaccagcctgctgctgtgcgaactgccgcatccggcgtttctgctg
attccggatattcagatgacccagaccaccagcagcctgagcgcgagcctgggcgatcgc
gtgaccattagctgccgcgcgagccaggatattagcaaatatctgaactggtatcagcag
aaaccggatggcaccgtgaaactgctgatttatcataccagccgcctgcatagcggcgtg
ccgagccgctttagcggcagcggcagcggcaccgattatagcctgaccattagcaacctg
gaacaggaagatattgcgacctattttgccagcagggcaacaccctgccgtatacctt
ggcggcggcaccaaactggaaattaccggcggcggcggcagcggcggcggcggcagcggc
ggcggcggcagcgaagtgaaactgcaggaaagcggcccgggcctggtggcgccgagccag
agcctgagcgtgacctgcaccgtgagcggcgtgagcctgccggattatggcgtgagctgg
attcgccagccgccgcgcaaaggcctggaatggctgggcgtgatttggggcagcgaaacc
acctattataacagcgcgctgaaaagccgcctgaccattattaaagataacagcaaaagc
caggtgtttctgaaaatgaacagcctgcagaccgatgataccgcgatttattattgcgcg
aaacattattattatggcggcagctatgcgatggattattggggccagggcaccagcgtg
accgtgagcagcgcggcggcgaccaccaccccggcgccgcgcccgccgaccccggcgccg
accattgcgagccagccgctgagcctgcgcccggaagcgtgccgcccggcggcggcggc
gcggtgcatacccgcggcctggattttgcgtgcgatatttatatttgggcgccgctggcg
ggcacctgcggcgtgctgctgctgagcctggtgattaccctgtattgcaaacgcggccgc
aaaaaactgctgtatattttaaacagccgtttatgcgcccggtgcagaccacccaggaa
gaagatggctgcagctgccgctttccggaagaagaagaaggcggctgcgaactgcgcgtg
aaatttagccgcagcgcggatgcgccggcgtatcagcagggccagaaccagctgtataac
gaactgaacctgggccgccgcgaagaatatgatgtgctggataaacgccgcggccgcgat
ccggaaatggcggcaaaccgcgccgcaaaaaccgcaggaaggcctgtataacgaactg
cagaaagataaaatggcggaagcgtatagcgaaattggcatgaaaggcgaacgccgccgc
ggcaaaggccatgatggcctgtatcagggcctgagcaccgcgaccaaagatacctatgat
gcgctgcatatgcaggcgctgccgccgcgc
```

FIG. 3B

III. SP-CD19binder-CD8link-CD4tm-signals LTG1562

*MLLLVTSLLLCELPHPAFLLIPDIQMTQTTSSLSASLGD*
*RVTISCRASQDISKYLNWYQQKPDGTVKLLIYHTSRLHSGVPSRFSGSGS*
*GTDYSLTISNLEQEDIATYFCQQGNTLPYTFGGGTKLEITGGGSGGGS*
*GGGGSEVKLQESGPGLVAPSQSLSVTCTVSGVSLPDYGVSWIRQPPRKGL*
*EWLGVIWGSETTYYNSALKSRLTIIKDNSKSQVFLKMNSLQTDDTAIYYC*
*AKHYYYGGSYAMDYWGQGTSVTVSS*AAAPAPRPPTPAPTIASQPLSLRPE
ACRPAAGGAVHTRGLDF<u>VQPMALIVLGGVAGLLLFIGLGIFFCVRCRPRR</u>
KKLLYIFKQPFMRPVQTTQEEDGCSCRFPEEEEGGCELRVKFSRSADAPA
YQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR atgctgctgctggtgaccagcctgctgctgtgcgaactgccgcatccggcgtttctgctg
attccggatattcagatgacccagaccaccagcagcctgagcgcgagcctgggcgatcgc
gtgaccattagctgccgcgcgagccaggatattagcaaatatctgaactggtatcagcag
aaaccggatggcaccgtgaaactgctgatttatcataccagccgcctgcatagcggcgtg
ccgagccgctttagcggcagcggcagcggcaccgattatagcctgaccattagcaacctg
gaacaggaagatattgcgacctattttgccagcagggcaacaccctgccgtatacctt
ggcggcggcaccaaactggaaattaccggcggcggcggcagcggcggcggcggcagcggc
ggcggcggcagcgaagtgaaactgcaggaaagcggcccgggcctggtggcgccgagccag
agcctgagcgtgacctgcaccgtgagcggcgtgagcctgccggattatggcgtgagctgg
attcgccagccgccgcgcaaaggcctggaatggctgggcgtgatttggggcagcgaaacc
acctattataacagcgcgctgaaaagccgcctgaccattattaaagataacagcaaaagc
caggtgtttctgaaaatgaacagcctgcagaccgatgataccgcgatttattattgcgcg
aaacattattattatggcggcagctatgcgatggattattggggccagggcaccagcgtg
accgtgagcagcgcggcggcgccggcgccgcgcccgccgaccccggcgccgaccattgcg
agccagccgctgagcctgcgcccggaagcgtgccgcccggcggcgggcggcgcggtgcat
acccgcggcctggattttgtgcagccgatggcgctgattgtgctgggcggcgtggcgggc
ctgctgctgtttattggcctgggcatttttttttgcgtgcgctgccgcccgcgccgcaaa
aaactgctgtatatttttaaacagccgtttatgcgcccggtgcagaccacccaggaagaa
gatggctgcagctgccgctttccggaagaagaagaaggcggctgcgaactgcgcgtgaaa
tttagccgcagcgcggatgcgccggcgtatcagcagggccagaaccagctgtataacgaa
ctgaacctgggccgccgcgaagaatatgatgtgctggataaacgccgcggccgcgatccg
gaaatgggcggcaaaccgcgccgcaaaaacccgcaggaaggcctgtataacgaactgcag
aaagataaaatggcggaagcgtatagcgaaattggcatgaaaggcgaacgccgccgcggc
aaaggccatgatggcctgtatcagggcctgagcaccgcgaccaaagatacctatgatgcg
ctgcatatgcaggcgctgccgccgcgc

FIG. 3C

IV. SP-CD19binder-CD8link-TNFRSF19tm-signals LTG1563

1 <u>MLLLVTSLLLCELPHPAFLLIP</u>DIQMTQTTSSLSASLGD
51 RVTISCRASQDISKYLNWYQQKPDGTVKLLIYHTSRLHSGVPSRFSGSGS
101 GTDYSLTISNLEQEDIATYFCQQGNTLPYTFGGGTKLEITGGGGSGGGGS
151 GGGGSEVKLQESGPGLVAPSQSLSVTCTVSGVSLPDYGVSWIRQPPRKGL
201 EWLGVIWGSETTYYNSALKSRLTIIKDNSKSQVFLKMNSLQTDDTAIYYC
251 AKHYYYGGSYAMDYWGQGTSVTVSSAAAPAPRPPTPAPTIASQPLSLRPE
301 ACRPAAGGAVHTRGLD<u>FDTALAAVICSALATVLLALLILCVIY</u>CKRQPRR
351 KKLLYIFKQPFMRPVQTTQEEDGCSCRFPEEEEGGCELRVKFSRSADAPA
401 YQQGQNQLYNELNLGRREEYDVLDKRRGRDPEMGGKPRRKNPQEGLYNEL
451 QKDKMAEAYSEIGMKGERRRGKGHDGLYQGLSTATKDTYDALHMQALPPR

```
atgctgctgctggtgaccagcctgctgctgtgcgaactgccgcatccggcgtttctgctg
attccggatattcagatgacccagaccaccagcagcctgagcgcgagcctgggcgatcgc
gtgaccattagctgccgcgcgagccaggatattagcaaatatctgaactggtatcagcag
aaaccggatggcaccgtgaaactgctgatttatcataccagccgcctgcatagcggcgtg
ccgagccgctttagcggcagcggcagcggcaccgattatagcctgaccattagcaacctg
gaacaggaagatattgcgacctatttttgccagcagggcaacacccctgccgtataccttt
ggcggcggcaccaaactggaaattaccggcggcggcggcagcggcggcggcggcagcggc
ggcggcggcagcgaagtgaaactgcaggaaagcggcccgggcctggtggcgccgagccag
agcctgagcgtgacctgcaccgtgagcggcgtgagcctgccggattatggcgtgagctgg
attcgccagccgccgcgcaaaggcctggaatggctgggcgtgatttggggcagcgaaacc
acctattataacagcgcgctgaaaagccgcctgaccattattaaagataacagcaaaagc
caggtgtttctgaaaatgaacagcctgcagaccgatgataccgcgatttattattgcgcg
aaacattattattatggcggcagctatgcgatggattattggggccagggcaccagcgtg
accgtgagcagc**gcggcggcgccggcgccgcgcccgccgaccccggcgccgaccattgcg
agccagccgctgagcctgcgcccggaagcgtgccgcccggcggcggcggcgcggtgcat
acccgcggcctggatttt**gataccgcgctggcggcggtgatttgcagcgcgctggcgacc
gtgctgctggcgctgctgattctgtgcgtgatttattgcaaacgccagccgcgccgcaaa
aaactgctgtatatttttaaacagccgtttatgcgcccggtgcagaccacccaggaagaa
gatggctgcagctgccgctttccggaagaagaagaaggcggctgcgaactgcgcgtgaaa
tttagccgcagcgcggatgcgccggcgtatcagcagggccagaaccagctgtataacgaa
ctgaacctgggccgccgcgaagaatatgatgtgctggataaacgccgcggccgcgatccg
gaaatgggcggcaaaccgcgccgcaaaaacccgcaggaaggcctgtataacgaactgcag
aaagataaaatggcggaagcgtatagcgaaattggcatgaaaggcgaacgccgccgcggc
aaaggccatgatggcctgtatcagggcctgagcaccgcgaccaaagatacctatgatgcg
ctgcatatgcaggcgctgccgccgcgc
```

FIG. 3D

V. SP-CD19binder-TNFRSF19link-TNFRSF19tm-signals
LTG1564

*MLLLVTSLLLCELPHPAFLLIP*DIQMTQTTSSLSASLGD
RVTISCRASQDISKYLNWYQQKPDGTVKLLIYHTSRLHSGVPSRFSGSGS
GTDYSLTISNLEQEDIATYFCQQGNTLPYTFGGGTKLEITGGGGSGGGGS
GGGGSEVKLQESGPGLVAPSQSLSVTCTVSGVSLPDYGVSWIRQPPRKGL
EWLGVIWGSETTYYNSALKSRLTIIKDNSKSQVFLKMNSLQTDDTAIYYC
AKHYYYGGSYAMDYWGQGTSVTVSSAAAVGFQDMECVPCGDPPPPYEPHC
ASKVNLVKIASTASSPRDTALAAVICSALATVLLALLILCVIYCKRQPRR
KKLLYIFKQPFMRPVQTTQEEDGCSCRFPEEEEGGCELRVKFSRSADAPA
YQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR atgctgctgctggtgaccagcctgctgctgtgcgaactgccgcatccggcgtttctgctg
attccggatattcagatgacccagaccaccagcagcctgagcgcgagcctgggcgatcgc
gtgaccattagctgccgcgcgagccaggatattagcaaatatctgaactggtatcagcag
aaaccggatggcaccgtgaaactgctgatttatcataccagccgcctgcatagcggcgtg
ccgagccgctttagcggcagcggcagcggcaccgattatagcctgaccattagcaacctg
gaacaggaagatattgcgacctattttgccagcagggcaacaccctgccgtatacctttt
ggcggcggcaccaaactggaaattaccggcggcggcggcagcggcggcggcggcagcggc
ggcggcggcagcgaagtgaaactgcaggaaagcggcccgggcctggtggcgccgagccag
agcctgagcgtgacctgcaccgtgagcggcgtgagcctgccggattatggcgtgagctgg
attcgccagccgccgcgcaaaggcctggaatggctgggcgtgatttggggcagcgaaacc
acctattataacagcgcgctgaaaagccgcctgaccattattaaagataacagcaaaagc
caggtgtttctgaaaaatgaacagcctgcagaccgatgataccgcgatttattattgcgcg
aaacattattattatggcggcagctatgcgatggattattggggccagggcaccagcgtg
accgtgagcagcgcggcggcggtgggctttcaggatatggaatgcgtgccgtgcggcgat
ccgccgccgccgtatgaaccgcattgcgcgagcaaagtgaacctggtgaaaattgcgagc
accgcgagcagcccgcgcgataccgcgctggcggcggtgatttgcagcgcgctggcgacc
gtgctgctggcgctgctgattctgtgcgtgatttattgcaaacgccagccgcgccgcaaa
aaactgctgtatattttaaacagccgtttatgcgcccggtgcagaccacccaggaagaa
gatggctgcagctgccgctttccggaagaagaagaaggcggctgcgaactgcgcgtgaaa
tttagccgcagcgcggatgcgccggcgtatcagcagggccagaaccagctgtataacgaa
ctgaacctgggccgccgcgaagaatatgatgtgctggataaacgccgcggccgcgatccg
gaaatgggcggcaaaccgcgccgcaaaaacccgcaggaaggcctgtataacgaactgcag
aaagataaaatggcggaagcgtatagcgaaattggcatgaaaggcgaacgccgccgcggc
aaaggccatgatggcctgtatcagggcctgagcaccgcgaccaaagatacctatgatgcg
ctgcatatgcaggcgctgccgccgcgc

CHIMERIC ANTIGEN RECEPTORS AND METHODS OF USE

CROSS-REFERENCE TO RELATED APPLICATIONS

This application is a 371 U.S. National Phase Application of PCT/US2016/056073, filed on Oct. 7, 2016, which claims the benefit of priority under 35 U.S.C. Section 119(e) to U.S. Provisional Patent Application No. 62/239,509, filed on Oct. 9, 2015, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 6, 2018, is named Sequence Listing.txt and is 68 kilobytes in size.

FIELD OF THE DISCLOSURE

This application relates to the field of cancer, particularly to chimeric antigen receptors (CARs) containing tumor necrosis factor receptor superfamily member transmembrane domains and methods of use.

BACKGROUND

Cancer is one of the deadliest threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after a single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single scFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5).

Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. Accordingly, there is an urgent and long felt need in the art for discovering compositions and methods for treatment of cancer using CARs that can exhibit intended therapeutic attributes without the aforementioned short comings.

The present invention addresses these needs by providing CAR compositions and therapeutic methods that can be used to treat cancers and other diseases and/or conditions. In particular, the present invention as disclosed and described herein provides CARs that exhibit a high surface expression on transduced T cells, exhibit a high degree of cytolysis and transduced T cell in vivo expansion and persistence.

SUMMARY

Novel chimeric antigen receptors (CARs) that contain tumor necrosis factor receptor superfamily (TNFRSF) member transmembrane domains are provided herein, as well as host cells (e.g., T cells) expressing the receptors, and nucleic acid molecules encoding the receptors. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

In one aspect, an isolated nucleic acid molecule encoding a chimeric antigen receptor (CAR) is provided comprising, from N-terminus to C-terminus, at least one extracellular antigen binding domain, at least one transmembrane TNFRSF domain, and at least one intracellular signaling domain.

In one embodiment, an isolated nucleic acid molecule encoding the CAR is provided wherein the encoded extracellular antigen binding domain comprises at least one single chain variable fragment of an antibody that binds to the antigen.

In another embodiment, an isolated nucleic acid molecule encoding the CAR is provided wherein the encoded extracellular antigen binding domain comprises at least one heavy chain variable region of an antibody that binds to the antigen.

In yet another embodiment, an isolated nucleic acid molecule encoding the CAR is provided wherein the encoded CAR extracellular antigen binding domain comprises at least one lipocalin-based antigen binding antigen (anticalins) that binds to the antigen.

In one embodiment, an isolated nucleic acid molecule is provided wherein the encoded extracellular antigen binding domain is connected to the TNFRSF transmembrane domain by a linker domain.

In another embodiment, an isolated nucleic acid molecule encoding the CAR is provided wherein the encoded extracellular antigen binding domain is preceded by a sequence encoding a leader or signal peptide.

In yet another embodiment, an isolated nucleic acid molecule encoding the CAR is provided wherein the encoded extracellular antigen binding domain targets an antigen that includes, but is not limited to, CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8, and is linked to the transmembrane TNFRSF16 domain, the transmembrane TNFRSF19 domain, or a combination thereof.

In another embodiment, an isolated nucleic acid molecule encoding the CAR is provided wherein the encoded linker domain is derived from the extracellular domain of TNFRSF 16 or TNFRSF 19, and is linked to the transmembrane TNFRSF16 domain, the transmembrane TNFRSF19 domain, or a combination thereof.

In a further embodiment, an isolated nucleic acid molecule encoding the CAR is provided wherein the encoded transmembrane TNFRSF domain comprises a transmembrane TNFRSF16 domain, a transmembrane TNFRSF19 domain, or a combination thereof.

In yet another embodiment, an isolated nucleic acid molecule encoding the CAR is provided wherein the nucleic acid sequence encoding the TNFRSF16 transmembrane domain comprises a sequence of SEQ ID NO: 1, or a sequence with 85%, 90%, 95%, 96%, 97%, 98% or 99% identity thereof.

In one embodiment, an isolated nucleic acid molecule encoding the CAR is provided wherein the encoded TNFRSF16 transmembrane domain comprises a sequence of SEQ ID NO: 2, or an amino acid sequence comprising at least one but not more 10 modifications of the amino acid sequence of SEQ ID NO: 2, or a sequence with 85%, 90%, 95%, 96%, 97%, 98% or 99% identity to an amino acid sequence of SEQ ID NO: 2.

In yet another embodiment, an isolated nucleic acid molecule encoding the CAR is provided wherein the nucleic acid sequence encoding the TNFRSF19 transmembrane domain comprises a sequence of SEQ ID NO: 3, or a sequence with 85%, 90%, 95%, 96%, 97%, 98% or 99% identity thereof.

In one embodiment, an isolated nucleic acid molecule encoding the CAR is provided wherein the encoded TNFRSF19 transmembrane domain comprises a sequence of SEQ ID NO: 4, or an amino acid sequence comprising at least one but not more than 10 modifications of the amino acid sequence of SEQ ID NO: 4, or a sequence with 85%, 90%, 95%, 96%, 97%, 98% or 99% identity to an amino acid sequence of SEQ ID NO: 4.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 5.

In yet another embodiment, an isolated nucleic acid molecule encoding the CAR is provided wherein the encoded leader sequence comprises the amino acid sequence of SEQ ID NO: 6.

In one aspect, a chimeric antigen receptor (CAR) is provided herein comprising, from N-terminus to C-terminus, at least one extracellular antigen binding domain, at least one transmembrane TNFRSF domain, and at least one intracellular signaling domain.

In one embodiment, a CAR is provided wherein the extracellular antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane TNFRSF domain comprises a transmembrane TNFRSF19 domain, a transmembrane TNFRSF16 domain, or a combination thereof.

In some embodiments, the CAR is provided wherein the extracellular antigen binding domain comprises CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 7. In one embodiment, the nucleic acid sequence encodes a CAR comprising the amino acid sequence of SEQ ID NO: 8.

In another embodiment, the nucleic acid sequence encoding a CAR comprises the nucleic acid sequence of SEQ ID NO: 9. In one embodiment, the nucleic acid sequence encodes a CAR comprising the amino acid sequence of SEQ ID NO: 10.

In another embodiment, the nucleic acid sequence encoding a CAR comprises the nucleic acid sequence of SEQ ID NO: 21. In one embodiment, the nucleic acid sequence encodes a CAR comprising the amino acid sequence of SEQ ID NO: 22.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain, at least one linker domain, at least one transmembrane TNFRSF domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane TNFRSF domain of the CAR contains a transmembrane TNFRSF16 domain, a transmembrane TNFRSF19 domain or a combination thereof.

In another embodiment, a pharmaceutical composition is provided wherein the human cancer includes an adult carcinoma comprising coral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds an antigen, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In another embodiment, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds one or more of the aforementioned antigens, under conditions sufficient to form an immune complex of the antigen binding domain on the CAR and the extracellular domain of one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular antigen binding domain, at least one linker or spacer domain, at least one transmembrane TNFRSF domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one extracellular antigen binding domain, at least one linker or spacer domain, at least one transmembrane TNFRSF domain, at least one intracellular signaling domain, wherein the T cells are T cells of the subject having cancer. In some embodiments of the aforementioned methods, the at least one transmembrane TNFRSF domain comprises a transmembrane TNFRSF16 domain, a transmembrane TNFRSF19 domain or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one extracellular antigen binding domain, at least one transmembrane TNFRSF domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 2 depicts certain transmembrane amino acid motifs in TNFRSF16 and TNFRSF19. The transmembrane amino acid sequences of CD8, CD4, TNFRSF16 and TNFRSF19 are also shown. Nine distinct features are highlighted in the header of FIG. 2. Each is an amino acid encoded by the human genome in the context of a transmembrane plasma membrane protein. The Amino acid abbreviations used herein are according to the IUPAC-IUB Joint Commission on Biochemical Nomenclature (JCBN).

FIGS. 3A, 3B, 3C, 3D, and 3 depicts several chimeric antigen receptors (CARs). The general scheme for the CARs includes, from the N terminus to the C terminus, a Signal peptide, Anti-CD19 scFv/FMC63, extracellular linker, transmembrane, 4-1BB, CD3 zeta wherein the bolded text represents the cloning sites for linking domains. FIG. 3A depicts a lentiviral vector expressing the CAR containing SP-CD19binder-CD8link-CD8tm-signaling (LTG1494). FIG. 3B depicts a lentiviral vector expressing the CAR containing SP-CD19binder-CD8link-CD8tm-signals (LTI re-engineered) (LTG1538). FIG. 3C depicts a lentiviral vector expressing the CAR containing SP-CD19binder-CD8link-CD4tm-signals (LTG1562). FIG. 3D depicts a lentiviral vector expressing the CAR containing SP-CD19binder-CD8link-TNFRSF19tm-signals (LTG1563). FIG. 3E depicts a lentiviral vector expressing the CAR containing SP-CD19binder-TNFRSF19link-TNFRSF19tm-signals (LTG1564).

FIG. 11A. NSG mice were inoculated with half million Raji cells stably expressing firefly luciferase on day 0, and tumor engraftment was verified on day 6. Then, mice were distributed into groups based on bioluminescence and were dosed with 10 million CAR T cells via tailvein on day 7. Tumor burden was evaluated by bioluminescence up to day 32. Construct 1563 was more efficient than 1494 in Raji tumor elimination in this model. FIG. 11B. Kaplan Meier plot demonstrating survival analysis of mice treated with CAR T cells. Statistical analysis was performed using GraphPad Prism. The surviving group is significantly different from non-surviving by Log-rank (Mantel-Cox) test, *p<0.05. Median survival: GFP-19 days, No Treatment (N.T.)-20 days, 1494-24 days.

DETAILED DESCRIPTION

Definitions

Figure 1:
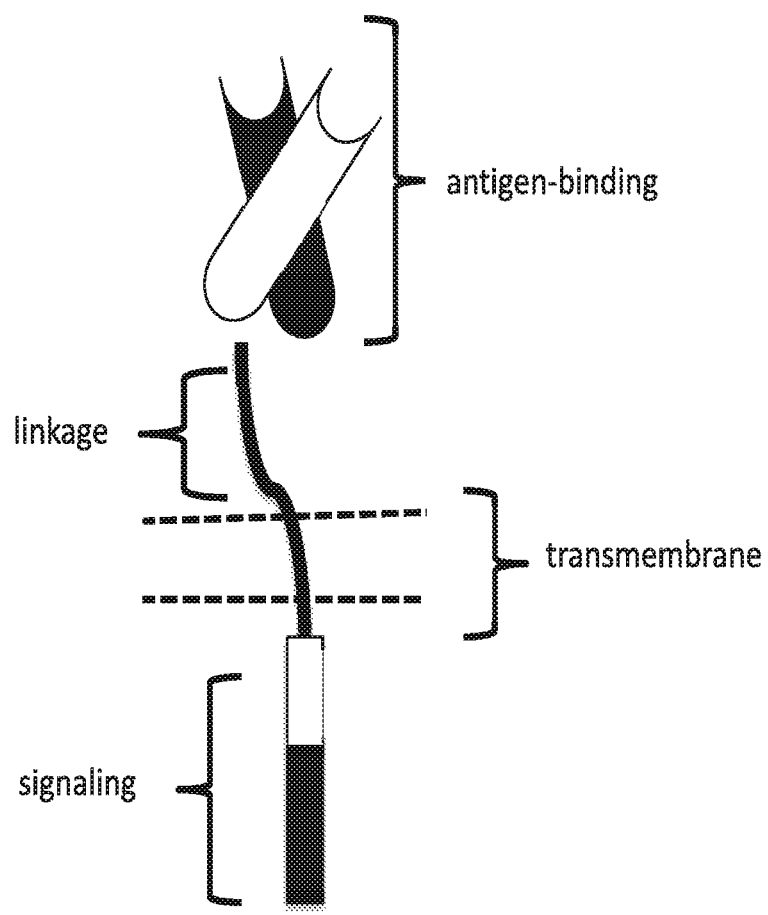
FIG. 1 depicts a schematic of a chimeric antigen receptor (CAR). The CAR contains an antigen binding domain, a linkage domain, a transmembrane domain and an intracellular signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−0.20% or in some instances .+−0.10%, or in some instances .+−0.5%, or in some instances .+−0.1%, or in some instances .+−0.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for chimeric antigen receptors (CARs) having tumor necrosis factor receptor superfamily (TNFRSF) member transmembrane domains and/or a modified linkage domain for linking the transmembrane domain to the extracellular antigen binding domain. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. This indicates that structural and sequence components of the protein domains used to create CARs, thought to be biologically inert, can have completely unexpected functional effects and thereby affect the therapeutic potential of a CAR.

While the ability to bind target antigen and the ability to transmit an activation signal to the T cell through these extracellular and intracellular domains, respectively, are important CAR design aspects, what has also become apparent is that other structural domains in the composition of a CAR also have a defining role for the function and clinical utility of the CAR.

Surprisingly and unexpectedly, it has now been discovered by the inventors that the transmembrane domain itself, and the way in which it links to the extracellular antigen binding domain and/or intracellular signaling domain of a CAR, also determine the functional activity of a CAR-expressing T cell. The CARs disclosed herein are expressed at a high level in a cell. A cell expressing the CAR has a high in vivo proliferation rate, produces large amounts of cytokines, and has a high cytotoxic activity against a cell having, on its surface, an antigen to which a CAR binds.

What follows is a detailed description of the inventive CARs including a description of their extracellular domain, the transmembrane domain and the intracellular domain, along with additional description of CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one extracellular domain capable of binding to an antigen, at least one tumor necrosis factor receptor superfamily (TNFRSF) transmembrane domain, and at least one intracellular domain.

A chimeric antigen receptor (CAR) is an artificially constructed hybrid protein or polypeptide containing the antigen binding domains of an antibody (e.g., single chain variable fragment (scFv)) linked to T-cell signaling domains via the novel tumor necrosis factor receptor superfamily (TNFRSF) member transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33, c-Met, PSMA, Glycolipid F77, EGFRvIII, GD-2, MY-ESO-1 TCR, MAGE A3 TCR, and the like.

Depending on the desired antigen to be targeted, the CAR can be engineered to include the appropriate antigen bind domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR targets CD19. Preferably, the antigen binding domain in the CAR is anti-CD19 scFV, wherein the nucleic acid sequence of the anti-CD19 scFV comprises the sequence set forth in SEQ ID NO: 27 In one embodiment, the anti-CD19 scFV comprises the nucleic acid sequence that encodes the amino acid sequence of SEQ ID NO: 28. In another embodiment, the anti-CD19 scFV portion of the CAR comprises the amino acid sequence set forth in SEQ ID NO: 28.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter pyloris, Legionella pneumophilia*, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more TNFRSF transmembrane domains fused to the extracellular domain of the CAR.

In one embodiment, the TNFRSF transmembrane domain comprises at least one TNFRSF16 transmembrane domain, at least one TNFRSF19 transmembrane domain, or a combination thereof. In one embodiment, an isolated nucleic acid molecule is provided wherein the encoded TNFRSF transmembrane domain comprises a TNFRSF16 transmembrane domain, a TNFRSF19 transmembrane domain, or a combination thereof.

In one embodiment, the isolated nucleic acid molecule encoding the TNFRSF16 transmembrane domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded TNFRSF16 transmembrane domain comprises an amino acid sequence of SEQ ID NO: 2, or an amino acid sequence with 85%, 90%, 95%, 96%, 97%, 98% or 99% identity to an amino acid sequence of SEQ ID NO: 2.

In another embodiment, the isolated nucleic acid molecule encoding the TNFRSF19 transmembrane domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded TNFRSF19 transmembrane domain comprises an amino acid sequence of SEQ ID NO: 4, or an amino acid sequence with 85%, 90%, 95%, 96%, 97%, 98% or 99% identity to an amino acid sequence of SEQ ID NO: 4.

As shown in Example 1 herein, certain important transmembrane amino acid motifs in TNFRSF16 and TNFRSF19 are depicted in FIG. 2 which shows the transmembrane amino acid sequences of CD8, CD4, TNFRSF16 and TNFRSF19. Nine distinct features are highlighted in the header. Each is an amino acid encoded by the human genome in the context of a transmembrane plasma membrane protein. The Amino acid abbreviations used herein are according to the IUPAC-IUB Joint Commission on Biochemical Nomenclature (JCBN) The features are expressed in two groupings. In feature 1, 2, and 3, the amino acid is composed of I, A, or L within the first 10 transmembrane residues. Feature 2 is adjacent or one amino acid removed from feature 1 and is either an A or I. Feature three is either an L or a V and is spaced one amino acid away from feature 2. The second group of features begins at least 5 but not more than 10 amino acids away from feature 3. Feature 4, 5, and 6 are a consecutive string of 3 amino acids composed of L or V. Feature 7 is one amino acid away from feature 6 and is composed solely of L. Feature 8 is adjacent to feature 7 and is composed of a V or L. This feature is lacking in CD4. Feature 9 is adjacent to feature 8 and is composed of an I or an A. The significance of these features is that they form a unique secondary structure within the plasma membrane of the cell, allowing for optimal signal transduction and subsequent T cell activation by the chimeric antigen receptor (CAR).

In the various embodiments of the CARs disclosed herein, the general scheme is set forth in FIGS. 3A, 3B, 3C, 3D, and 3E and includes, from the N-terminus to the C-terminus, a signal or leader peptide, anti-CD19 scFv/FMC63, extracellular linker, transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 29, and encodes the CAR comprising the amino acid sequence as set forth in SEQ ID NO: 30 [SP-CD19binder-CD8link-CD8tm-signaling (LTG1494)(as depicted in FIG. 3A)].

In one embodiment, the nucleic acid sequence encoding a CAR comprises the nucleic acid sequence of SEQ ID NO: 31, and encodes the CAR comprising the amino acid sequence as set forth in SEQ ID NO: 32 [SP-CD19binder-CD8link-CD8tm-signals (LTI re-engineered) (LTG1538) (as depicted in FIG. 3B)].

In another embodiment, the nucleic acid sequence encoding a CAR comprises the nucleic acid sequence of SEQ ID NO: 21, and encodes the CAR comprising the amino acid sequence as set forth in SEQ ID NO: 22 [SP-CD19binder-CD8link-CD4tm-signals (LTG1562) (as depicted in FIG. 3C)]. In another embodiment, the nucleic acid sequence encoding a CAR comprises the nucleic acid sequence of SEQ ID NO: 39, and encodes the CAR comprising the amino acid sequence as set forth in SEQ ID NO: 22 [SP-CD19binder-CD8link-CD4tm-signals (LTG1562) (as depicted in FIG. 3C)].

In yet another embodiment, the nucleic acid sequence encoding a CAR comprises the nucleic acid sequence of SEQ ID NO: 7, and encodes the CAR comprising the amino acid sequence as set forth in SEQ ID NO: 8 [SP-CD19binder-CD8link-TNFRSF19tm-signals (LTG1563)(as depicted in FIG. 3D)]. In yet another embodiment, the nucleic acid sequence encoding a CAR comprises the nucleic acid sequence of SEQ ID NO: 40, and encodes the CAR comprising the amino acid sequence as set forth in SEQ ID NO: 8 [SP-CD19binder-CD8link-TNFRSF 19tm-signals (LTG1563)(as depicted in FIG. 3D)].

In yet another embodiment, the nucleic acid sequence encoding a CAR comprises the nucleic acid sequence of SEQ ID NO: 9, and encodes the CAR comprising the amino acid sequence as set forth in SEQ ID NO: 10 [SP-SP-CD19binder-TNFRSF19link-TNFRSF19tm-signals LTG1564 (LTG1564) (as depicted in FIG. 3E)]. In yet another embodiment, the nucleic acid sequence encoding a CAR comprises the nucleic acid sequence of SEQ ID NO: 41, and encodes the CAR comprising the amino acid sequence as set forth in SEQ ID NO: 10 [SP-SP-CD19binder-TNFRSF19link-TNFRSF19tm-signals LTG1564 (LTG1564) (as depicted in FIG. 3E)].

Figure 5:
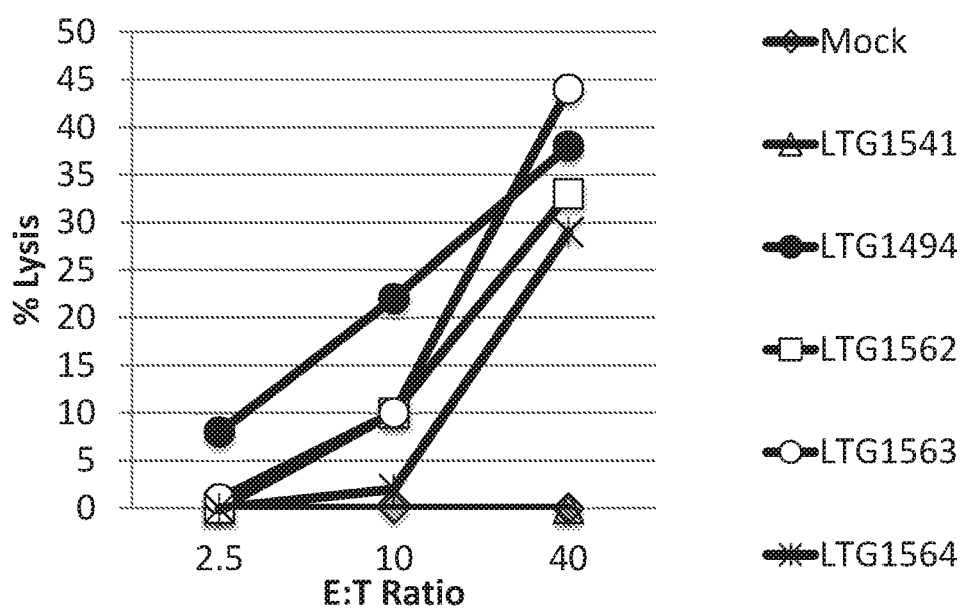
FIG. 5 depicts the anti-tumor activity of CARs containing the FMC63-derived anti-CD19 binding motif, the 4-1BB/CD3-zeta chain signaling motif and the TNFRSF transmembrane domains. Non-transduced expanded T cells (mock, open diamond) or T cells transduced with a LV expressing a control protein (LNGFR, LTG, open triangle) served as controls. The CAR-T featuring a CD8-derived linker and CD8-transmembrane domain (LTG1494, solid circles) showed strong lytic activity at the effector to target (E:T) ratios listed on the x-axis. The CAR-T expressing the CD8 linker and CD4 transmembrane (LTG1562, open square) or TNFRSF19 linker and transmembrane domains both showed appreciable lytic activity as well (LTG1564, star). The CAR-T expressed CD8 linker and TNFRSF19 transmembrane regions were tested (LTG1563, open circle) exhibited very strong lytic activity.

As shown in Example 2 and FIG. 5, respectively, the unexpected high cytolytic activity of the TNFRSF-containing CARs was demonstrated when lentiviral vectors (LV) expressing the following CARs were created and tested for anti-leukemia activity. Each experimental CAR contains the 4-1BB/CD3-zeta chain signaling motif and the FMC63-derived anti-CD19 binding motif. The Raji leukemia cell line was used as a target in cytolysis assays. The CAR-T featuring a CD8-derived linker and CD8-transmembrane domain (c.f, FIG. 5, LTG1494, solid circles) showed strong lytic activity at the effector to target (E:T) ratios listed on the x-axis. CAR-T expressing the CD8 linker and CD4 transmembrane (c.f, FIG. 5, LTG1562, open square) or TNFRSF19 linker and transmembrane domains both showed appreciable lytic activity as well (c.f, FIG. 5, LTG1564, star). Surprisingly, it was found that very strong lytic activity was seen when the CAR-T containing an expressed CD8 linker and TNFRSF19 transmembrane regions were tested (c.f, FIG. 5, LTG1563, open circle).

It is expected that due to the high amino acid conservation between the transmembrane regions of TNFRSF16 and TNFRSF19 in the conserved region depicted in FIG. 2 infra, a CAR-T-containing expressed CD8 linker and TNFRSF16 transmembrane regions would also exhibit very strong cytolytic activity when the CAR-T expressed CD8 linker and TNFRSF16 transmembrane regions are tested.

The surface expression of the TNFRSF transmembrane domain-containing CARs is shown in Example 2 and summarized in Table 2. The expression level for each CAR domain was determined by flow cytometric analysis of LV-transduced T cells using biotinylated protein L and streptavidin-conjugated phycoerythrin (PE). The TNFRSF19 transmembrane domain-containing CAR (LTG1564) exhibited high surface expression compared to an LNGFR-mCherry CAR (LTG1541) which expresses a control protein (LNGFR-mCherry) and has no surface expression or cytolytic activity (c.f, Example 1, FIG. 5, and Table 2).

It is also expected that due to the high amino acid conservation between the transmembrane domain regions of TNFRSF16 and TNFRSF19 in the conserved region depicted in FIG. 2 infra, a CAR-T-containing expressed CD8 linker and TNFRSF16 transmembrane regions would also exhibit high surface expression when the CAR-T expressed CD8 linker and TNFRSF16 transmembrane regions are tested compared to the LNGFR-mCherry CAR (LTG1541) control.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with TNFRSF16 and TNFRSF19 as exemplary transmembrane domains, other members within the tumor necrosis factor receptor superfamily may be used to derive the TNFRSF transmembrane domains and/or linker or spacer domains for use in the CARs described herein. Table 1 infra depicts the members within the tumor necrosis factor receptor superfamily.

TABLE 1

Tumor Necrosis Factor Receptor Superfamily (TNFRSF)

| Approved Symbol | Approved Name | Previous Symbols | Synonyms | Chromosome |
|---|---|---|---|---|
| EDAR | ectodysplasin A receptor | ED3, DL | ED5, EDA3, Edar, ED1R, EDA1R | 2q13 |
| TNFRSF1A | tumor necrosis factor receptor superfamily, member 1A | TNFR1 | TNF-R, TNFAR, TNFR60, TNF-R-I, CD120a, TNF-R55 | 12p13.2 |
| TNFRSF1B | tumor necrosis factor receptor superfamily, member 1B | TNFR2 | TNFBR, TNFR80, TNF-R75, TNF-R-II, p75, CD120b | 1p36.22 |
| LTBR | lymphotoxin beta receptor (TNFR superfamily, member 3) | D12S370 | TNF-R-III, TNFCR, TNFRSF3, TNFR2-RP, TNFR-RP | 12p13 |
| TNFRSF4 | tumor necrosis factor receptor superfamily, member 4 | TXGP1L | ACT35, OX40, CD134 | 1p36 |
| CD40 | CD40 molecule, TNF receptor superfamily member 5 | TNFRSF5 | p50, Bp50 | 20q12-q13.2 |
| FAS | Fas cell surface death receptor | APT1, FAS1, TNFRSF6 | CD95, APO-1 | 10q24.1 |
| TNFRSF6B | tumor necrosis factor receptor superfamily, member 6b, decoy | | DcR3, DCR3, TR6, M68 | 20q13.33 |
| CD27 | CD27 molecule | TNFRSF7 | S152, Tp55 | 12p13 |
| TNFRSF8 | tumor necrosis factor receptor superfamily, member 8 | CD30, D1S166E | KI-1 | 1p36 |
| TNFRSF9 | tumor necrosis factor receptor superfamily, member 9 | ILA | CD137, 4-1BB | 1p36 |
| TNFRSF10A | tumor necrosis factor receptor superfamily, member 10a | | DR4, Apo2, TRAILR-1, CD261 | 8p21 |
| TNFRSF10B | tumor necrosis factor receptor superfamily, member 10b | | DR5, KILLER, TRICK2A, TRAIL-R2, TRICKB, CD262 | 8p22-p21 |

TABLE 1-continued

Tumor Necrosis Factor Receptor Superfamily (TNFRSF)

| Approved Symbol | Approved Name | Previous Symbols | Synonyms | Chromosome |
|---|---|---|---|---|
| TNFRSF10C | tumor necrosis factor receptor superfamily, member 10c, decoy without an intracellular domain | | DcR1, TRAILR3, LIT, TRID, CD263 | 8p22-p21 |
| TNFRSF10D | tumor necrosis factor receptor superfamily, member 10d, decoy with truncated death domain | | DcR2, TRUNDD, TRAILR4, CD264 | 8p21 |
| TNFRSF11A | tumor necrosis factor receptor superfamily, member 11a, NFKB activator | PDB2, LOH18CR1 | RANK, CD265, FEO | 18q22.1 |
| TNFRSF11B | tumor necrosis factor receptor superfamily, member 11b | OPG | OCIF, TR1 | 8q24 |
| TNFRSF12A | tumor necrosis factor receptor superfamily, member 12A | | FN14, TweakR, CD266 | 16p13.3 |
| TNFRSF13B | tumor necrosis factor receptor superfamily, member 13B | | TACI, CD267, IGAD2 | 17p11.2 |
| TNFRSF13C | tumor necrosis factor receptor superfamily, member 13C | | BAFFR, CD268 | 22q13.1-q13.3 |
| TNFRSF14 | tumor necrosis factor receptor superfamily, member 14 | | HVEM, ATAR, TR2, LIGHTR, HVEA, CD270 | 1p36.32 |
| NGFR | nerve growth factor receptor | | TNFRSF16, p75NTR, CD271 | 17q21-q22 |
| TNFRSF17 | tumor necrosis factor receptor superfamily, member 17 | BCMA | BCM, CD269, TNFRSF13A | 16p13.1 |
| TNFRSF18 | tumor necrosis factor receptor superfamily, member 18 | | AITR, GITR, CD357 | 1p36.3 |
| TNFRSF19 | tumor necrosis factor receptor superfamily, member 19 | | TAJ-alpha, TROY, TAJ, TRADE | 13q12.11-q12.3 |
| RELT | RELT tumor necrosis factor receptor | TNFRSF19L | FLJ14993 | 11q13.2 |
| TNFRSF21 | tumor necrosis factor receptor superfamily, member 21 | | DR6, CD358 | 6p21.1 |
| TNFRSF25 | tumor necrosis factor receptor superfamily, member 25 | TNFRSF12 | DR3, TRAMP, WSL-1, LARD, WSL-LR, DDR3, TR3, APO-3 | 1p36.2 |
| EDA2R | ectodysplasin A2 receptor | | XEDAR, EDAA2R, EDA-A2R, TNFRSF27 | Xq11.1 |
| EDAR | ectodysplasin A receptor | ED3, DL | ED5, EDA3, Edar, ED1R, EDA1R | 2q13 |

The data depicted in Table 1 supra was used with permission of the HGNC Database, HUGO Gene Nomenclature Committee (HGNC), EMBL Outstation-Hinxton, European Bioinformatics Institute, Wellcome Trust Genome Campus, Hinxton, Cambridgeshire, CB10 1SD, UK www.genenames.org. [Gray K A, Yates B, Seal R L, Wright M W, Bruford E A. genenames.org: the HGNC resources in 2015. Nucleic Acids Res. 2015 January; 43 (Database issue): D1079-85. doi: 10.1093/nar/gku1071. PMID: 25361968].

In one embodiment, an isolated nucleic acid molecule is provided wherein the encoded linker domain is derived from the extracellular domain of CD8, and is linked to the transmembrane TNFRSF16 domain, the transmembrane TNFRSF19 domain, or a combination thereof.

In one embodiment, an isolated nucleic acid molecule is provided wherein the encoded linker domain is derived from the extracellular domain of TNFRSF 16 or TNFRSF 19, and is linked to the TNFRSF16 transmembrane domain, the TNFRSF19 transmembrane domain, or a combination thereof.

In one embodiment, the transmembrane domain that naturally is associated with one of the domains in the CAR is used in addition to the novel TNFRSF transmembrane domains described supra.

In some instances, the transmembrane domain can be selected or by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 11. In one embodiment, the CD8 transmembrane domain comprises the nucleic acid sequence that encodes the amino acid sequence of SEQ ID NO: 12. In another embodiment, the CD8 transmembrane domain comprises the amino acid sequence of SEQ ID NO: 12.

In some instances, the transmembrane domain of the CAR comprises the CD8.alpha.hinge domain. In one embodiment, the CD8 hinge domain comprises the nucleic acid sequence of SEQ ID NO: 13. In one embodiment, the CD8 hinge domain comprises the nucleic acid sequence that encodes the amino acid sequence of SEQ ID NO: 14. In another embodiment, the CD8 hinge domain comprises the amino acid sequence of SEQ ID NO: 14.

3. Spacer Domain

In the CAR, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 15) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain (CH1 region or CL region, for example, a peptide having an amino acid sequence shown in SEQ ID NO.: 16) can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 6).

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3.delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 19.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 20.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 18 and the signaling domain of CD3-zeta comprises the amino acid sequence set forth in SEQ ID NO: 20.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbomane)-carboxylic acid, γ-diaminobutyric acid, 3-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from)

the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Also, a CAR, a T cell expressing a CAR, an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.) In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as a-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-β-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λϋTIO, λυTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417

(1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Thi and Th2 cells, CD8+ T cells (e.g., cytotoxic T cells), tumor infiltrating cells, memory T cells, na'ive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., meduUoblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol. 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a non-toxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science,* 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems,* Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly.

See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, Kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Chimeric Antigen Receptors Containing TNFRSF Transmembrane Domains

Generation of CARs with novel transmembrane sequences was achieved according to the procedure described herein.

The transgene expression cassette for the CAR (vector genome) was created by in vitro synthesis of the entire open reading frame encoding the antigen binding, linker, transmembrane and T cell signaling domains. Lentivirus expression vectors (LV) expressing the CARs were created by co-transfection of envelope, helper, and vector genome-encoding plasmids into a producer cell line and vector containing supernatants harvested and titrated on an indicator cell line using standard methods for mammalian cell culture and DNA transfection. Vector containing supernatants were then used to transduce primary human lymphocytes isolated from peripheral blood and expression of the CAR-encoded transgene demonstrated by flow cytometric analysis of the transduced T cell population. Lymphocyte populations expressing CAR were then tested in functional assays. For cytokine production, CAR-T cells were co-cultured with tumor cell line expressing the cognate antigen. Supernatants were collected and analyzed by ELISA assay at 24 hours. For cytotoxicity, tumor cell lines were co-cultured with CAR-T cells and the degree of cell death monitored by flow cytometric analysis of the loss of membrane integrity in the target cell population or biochemical activation of cell death pathways.

Figure 4:
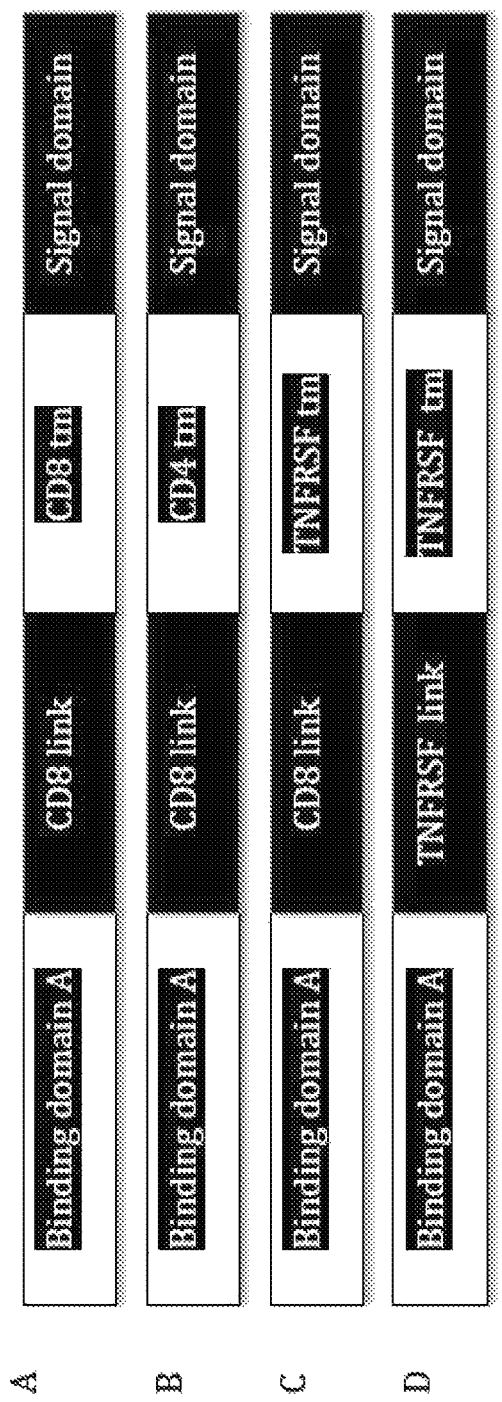
FIG. 4 depicts a schematic of the general domain structure of CARs with novel transmembrane sequences. Depicted is a series of unique CARs utilizing an anti-CD19 antibody FMC63 (binding domain A). Binding domains were linked to CD8 linkers and CD8 transmembrane domains, CAR format (A), CD4 (B), TNFRSF19 (C) transmembrane domains, or to a TNFRSF19 linker and transmembrane domain (D).

For proof of principle, each CAR utilized the 4-1BB/CD3-zeta chain signaling motif and the FMC63-derived anti-CD19 binding motif and featured the CD8-derived linker and CD8-transmembrane domain (c.f., FIG. 2 and FIG. 4 (*a*)), the CD8 linker and CD4 transmembrane (cf., FIG. 2 and FIG. 4 (*b*)), TNFRSF19 linker and transmembrane domains (c.f., FIG. 2 and FIG. 4 (*c*)), or an expressed CD8 linker and TNFRSF19 transmembrane regions (c.f., FIG. 2 and FIG. 4 (*d*)).

The core residues defining the transmembrane motif of TNFRSF16 and TNFRSF19 in comparison to the transmembrane motifs present in the human CD4 and CD8a proteins reveal the presence of a core pattern of sequence homology that the inventors claim to be associated with signal transducing activity in CARs.

A schematic of a chimeric antigen receptor showing the relative position of the transmembrane domain to the extracellular antigen binding domain and the intracellular signaling domain has been shown in FIG. 1.

The transmembrane amino acid sequences of CD8, CD4, TNFRSF16 and TNFRSF19 and certain important transmembrane amino acid motifs in TNFRSF16 and TNFRSF19 have been shown in FIG. 2. Nine distinct features are highlighted in the header of FIG. 2. Each is an amino acid encoded by the human genome in the context of a transmembrane plasma membrane protein. The Amino acid abbreviations used herein are according to the IUPAC-IUB Joint Commission on Biochemical Nomenclature (JCBN). The features were expressed in two groupings. In feature 1, 2, and 3, the amino acid is composed of I, A, or L within the first 10 transmembrane residues. Feature 2 is adjacent or one amino acid removed from feature 1 and is either an A or I. Feature three is either an L or a V and is spaced one amino acid away from feature 2. The second group of features begins at least 5 but not more than 10 amino acids away from feature 3. Feature 4, 5, and 6 are a consecutive string of 3 amino acids composed of L or V. Feature 7 is one amino acid away from feature 6 and is composed solely of L. Feature 8 is adjacent to feature 7 and is composed of a V or L. This feature is lacking in CD4. Feature 9 is adjacent to feature 8 and is composed of an I or an A. The significance of these features is that they form a unique secondary structure within the plasma membrane of the cell, allowing for optimal signal transduction and subsequent T cell activation by the chimeric antigen receptor (CAR).

Example 2

T Cells Expressing Chimeric Receptors Exhibit High Surface Expression and Cytolytic Activity The CARs disclosed herein were expressed at a high level in the Raji cell line. The cells expressing the CAR had a high proliferation rate, produced large amounts of cytokines, and had a high cytotoxic activity against a cell having, on its surface, an antigen to which a CAR binds.

To demonstrate the cytolytic activity of the identified transmembrane motifs, chimeric antigen receptors were created that include a portion of TNFRSF19 transmembrane or transmembrane and linker domains as depicted in FIG. 3.

Lentivirus expression vectors (LV) expressing the CARs utilizing the 4-1BB/CD3-zeta chain signaling motif and the FMC63-derived anti-CD19 binding motif featured either the CD8-derived linker and CD8-transmembrane domain (c.f, FIG. 2 and FIG. 4 (a), LTG1494, solid circles depicted in FIG. 5), the CD8 linker and CD4 transmembrane (c.f, FIG. 2 and FIG. 4 (b), LTG1562, open square depicted in FIG. 5), TNFRSF19 linker and transmembrane domains (c.f, FIG. 2 and FIG. 4 (c), LTG1564, star depicted in FIG. 5), or an expressed CD8 linker and TNFRSF19 transmembrane regions (c.f, FIG. 2 and FIG. 4 (d), LTG1563, open circle depicted in FIG. 5) were constructed by the methods described in Example 1 supra.

a) Cytolysis Assay of CARs

The CARs were then tested in a cytolysis assay which involved a Raji cell line (CCL-86 from ATCC) which was transduced with a LV encoding luciferase (Raji-luc). Raji-luc culture and the cytolysis assay itself are carried out in RPMI-1640 medium containing 10% fetal bovine serum under standard tissue culture conditions. The addition of a luciferase substrate allows the number of viable Raji cells to be accurately measured in each well of a 96-well tissue culture plate containing a constant number of target cells. CAR T cells were generated by stimulation with anti-CD3/CD28 beads (TransACT, Miltenyi Bitoec) under serum free conditions in TexMACS medium (Miltenyi Biotec) containing IL-2. Cells were activated for 3 days, exposed to LV, and cultured for up to 10 additional days. Determination of cytolytic activity of CAR-expressing T cells was carried out by co-incubation of Raji-luc with activated T cells (control), activated T cell expressing a LV-encoded control protein (LNGFR control), or a LV encoding a CAR specific for a cell surface antigen present on Raji-luc (in this case CD19). Increasing the number of effector CAR-T cells per well allowed different effector to target ratios to be tested. Viable Raji-luc at the end of a 24 hour co-incubation period was determined by adding luciferase substrate and measuring light emission in a plate reader. Cytotoxicity was quantified as a percentage of the luciferase signal from viable Raji-luc per well with no T cells in comparison to Raji-luc co-incubated with CAR-T cells.

b) Cell Surface Expression Assay of CARs

The CAR-T cells were then tested in a flow cytometry based cell surface expression assay which involved exposure to biotinylated protein L, which binds to the light chain-derived domain of the extracellular aspect of CARs. The amount of biotinylated protein L binding to the CAR domain was determined by secondary staining with avidin conjugated to phycoerythrin (PE). The percentage of single cells positively staining for protein L-binding as determined by the PE signal on a MACS-Quant flow cytometer was used to calculate CAR expression.

c) Cytolysis Assay of CARs

An unexpected high lytic activity of the TNFRSF-containing the CARs was demonstrated when lentivirus expression vectors (LV) expressing the following CARs were created and tested for anti-leukemia activity (See FIG. 5).

Each experimental CAR contains the 4-1BB/CD3-zeta chain signaling motif and the FMC63-derived anti-CD19 binding motif. The CAR-T featuring a CD8-derived linker and CD8-transmembrane domain (c.f, FIG. 4, LTG1494, solid circles) showed strong lytic activity at the effector to target (E:T) ratios listed on the x-axis. CAR-T expressing the CD8 linker and CD4 transmembrane (c.f, FIG. 4, LTG1562, open square) or TNFRSF19 linker and transmembrane domains both showed appreciable lytic activity as well (c.f, FIG. 4, LTG1564, star). Surprisingly, it was found that very strong lytic activity was seen when the CAR-T containing an expressed CD8 linker and TNFRSF19 transmembrane regions were tested (c.f, FIG. 4, LTG1563, open circle).

In this analysis, while high cytolytic activity was seen by the TNFRSF19 transmembrane domain containing CARs, there was also a marked difference between the different formats, with LTG1563 (containing CD8 linker and TNFRSF19 transmembrane) showing both strong lytic activity and high surface expression of LV-transduced T cells.

As there was high amino acid conservation between the transmembrane regions of TNFRSF16 and TNFRSF19 in the conserved region as depicted in FIG. 2, a CAR-T-containing expressed CD8 linker and TNFRSF16 transmembrane regions also exhibited very strong cytolytic activity when the CAR-T expressed CD8 linker and TNFRSF16 transmembrane regions were tested.

d) Cell Surface Expression Assay of CARs

It has been demonstrated that the cell surface expression of the CAR on the T cell plasma membrane was also an important parameter required for robust activity of therapeutic cellular populations expressing CARs. The cell surface expression of the CAR on the T cell plasma membrane was detected by flow cytometric analysis.

The analysis of cell surface expression (as determined by flow cytometric analysis) used indirect fluorescent staining of protein L bound to the Ig-derived binding domain of the CAR of transduced T cells with the Lentivirus expression vectors (LV). The results showed expression of the CARs utilizing the 4-1BB/CD3-zeta chain signaling motif and the FMC63-derived anti-CD19 binding motif featured either the CD8-derived linker and CD8-transmembrane domain (c.f, FIG. 4 (a)), the CD8 linker and CD4 transmembrane (c.f, FIG. 4 (b)), TNFRSF19 linker and transmembrane domains (c.f, FIG. 2 and FIG. 4 (c)), or an expressed CD8 linker and TNFRSF19 transmembrane regions (c.f., FIG. 4 (d)) constructed by the methods described in Example 1 supra is shown in Table 2 below.

The results of the cell surface expression of the TNFRSF transmembrane domain-containing CARs are depicted in the Table 2. The cell surface expression level for each CAR domain was determined by flow cytometric analysis of LV-transduced T cells using biotinylated protein L and streptavidin-conjugated phycoerythrin (PE). The TNFRSF19 transmembrane domain-containing CAR (LTG1564) exhibited high surface expression compared to an LNGFR-mCherry CAR (LTG1541) which expresses a control protein (LNGFR-mCherry) and has no surface expression or cytolytic activity (c.f., Example 1, FIG. 5 and Table 2).

Table 2 infra depicts the summary of the results of the cytolytic and surface expression of TNFRSF domain containing CARs. Activated human T cells received no LV (Mock) or were transduced with LV encoding the following combinations of linker and transmembrane (Linker_TM) domains: CD8-transmembrane and linker domain (LTG1494), CD8 linker and CD4 transmembrane (LTG1562), CD8 linker and TNFRSF19 transmembrane region (LTG1563), TNFRSF19 linker and TNFRSF19 transmembrane domains (LTG1564). LTG1541 expresses a control protein (LNGFR-mCherry) and has no cytolytic activity. Expression of cytolytic activity was determined using the Raji cell line, FIG. 4. Expression level for each CAR domain was determined by flow cytometric analysis of LV-transduced T cells using biotinylated protein L and streptavidin-conjugated phycoerythrin (PE).

TABLE 2

Summary of cytolytic and surface expression of TNFRSF domain containing CARs.

|  | Linker_TM | Expression | Cytolysis |
|---|---|---|---|
| Mock | None | n/a | none |
| LTG1541 | LNGFR | Hi | none |
| LTG1494 | CD8_CD8 | Hi | Hi |
| LTG1562 | 8_4 | Med | Hi |
| LTG1563 | 8_TNFRSF | Hi | Hi |
| LTG1564 | TNFRSF_TNFRSF | Low | Hi |

The CAR-T-containing expressed CD8 linker and TNFRSF16 transmembrane regions exhibited high cell surface expression as compared to the LNGFR-mCherry CAR (LTG1541) control.

Example 3

Utilization of Linker and/or Transmembrane Domains Derived from TNFRSF Members Enables Fine-Tuning of CAR T Anti-Tumor Function In this Example, the unexpected superiority of TNFRSF19 and TNFRSF9 to the CD8-encoded transmembrane domain is demonstrated. In CAR19-based tumor killing assays, and in the induction of IFN gamma, TNF alpha, IL-2, and GM-CSF cytokines in vitro upon co-culture with tumor target cells, both proved superior. Moreover, the TNFRSF19-derived CAR19 is demonstrated to be superior to the CD8 transmembrane CAR19 in elimination of an established Raji Burkitt lymphoma in a mouse model of human leukemia. Importantly, the incorporation of the transmembrane domain derived from TNFRSF16 (also known as LNGFR, low affinity neurotrophin receptor) into CAR19 blocked all in vitro and in vivo activity, despite high level of surface CAR expression in T cells. Thus indicating that not all transmembrane regions, even from proteins in the same superfamily such as the TNFRSF, function as components of a CAR.

The novel findings demonstrate that the transmembrane domain of CAR plays a role in CAR T function beyond a simple connection between the extracellular and the intracellular domains. Furthermore, the magnitude of a CAR T response can be enhanced or inhibited by the use of novel transmembrane domains.

Materials and Methods (a) Cell Lines (PBMC and Targets)

All cell lines and reagents were purchased from American Tissue Culture Collection (ATCC, Manassas, Va.), unless otherwise noted. The Raji and K562 cell lines were cultured in RPMI-1640 medium supplemented with 10% heat-inactivated fetal bovine serum and 2 mM glutamine. The human embryonic kidney cell line 293T was propagated in Dulbecco's modified Eagle medium (DMEM) supplemented with 10% heat-inactivated FBS.

Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. The mouse-adapted Raji-luc line was generated by engrafting a Raji clone stably expressing firefly luciferase into NSG mice (NOD.Cg-Prkd-$c^{scid}$ Il2rg$^{tm1Wjl}$/SzJ), The Jackson Laboratory Sacramento, Calif.), isolating the engrafted Raji-luc tumor cells from mouse spleens by either positive (CD19 microBeads, human, Miltenyi Biotec) or negative selection (mouse cell depletion kit, Miltenyi Biotec), expanding in culture, and re-cloning to facilitate the selection of clones with high expression of firefly luciferase.

Whole blood was collected from healthy volunteers at Oklahoma Blood Institute (OBI) with donors' written consent. CD4-positive and CD8-positive human T cells were purified from buffy coats via positive selection using a 1:1 mixture of CD4- and CD8-MicroBeads (Miltenyi Biotec, Bergisch Gladbach, FRG) according to manufacturer's protocol.

(b) Creation of Chimeric Antigen Receptor (CAR) Expression Vectors

CAR antigen-binding domains, scFv, sequences were derived from the mouse hybridoma FMC-63 for CD19 (FMC-63: aa 1-267, GenBank ID: HM852952.1). CAR T constructs were generated by linking FMC63 scFv in frame to the designated linking and transmembrane domains, and then to 4-1BB (CD137, aa 214-255, UniProt sequence ID Q07011) signaling domain and CD3 zeta signaling domain (CD247, aa 52-163, Ref sequence ID: NP_000725.1). Construct 1494 was designed to approximate the published CD19 CAR configuration (Chimeric receptors with 4-1BB signaling capacity provoke potent cytotoxicity against acute lymphoblastic leukemia, 2004, C Imai, K Mihara, M Andreansky, IC Nicholson, C-H Pui, TL Geiger, D Campana. Leukemia, 18:676-84) (referred to in the specification as "1494"). The 1494 construct incorporates the linker and transmembrane domains derived from the human CD8 alpha protein (UniProt sequence ID P01732, aa 138-206). CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T Cell Transduction

Human primary T cells from normal donors were purified from buffy coats following immunomagnetic bead selection of CD4+ and CD8+ cells, cultivated in TexMACS medium supplemented with 40 IU/ml IL-2 at a density of 0.3 and $2 \times 10^6$ cells/ml, activated with CD3/CD28 MACS® GMP TransAct reagent (Miltenyi Biotec) and transduced on day 3 with lentiviral vectors encoding CAR constructs in the presence of 10 μg/ml protamine sulfate (Sigma-Aldrich, St. Louis, Mo.) overnight, and media exchanged on day 4. On day 5, cultures were transferred to TexMACS medium supplemented with 200 IU/ml IL-2, and propagated until harvest on day 10-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). For cytokine release assays, effector and target cells were combined at ratio 10:1 and incubated overnight. Harvested supernatants were analyzed for secreted cytokines using or MACSplex human cytokine bead array kit (Miltenyi Biotec).

(e) Western Blot

Two million CAR T cells were washed twice in cold PBS (Lonza, Walkersville, Md.), lysed in cold RIPA buffer containing a protease and phosphatase inhibitor cocktail. The lysate was incubated at 4° C. for 20 minutes, pelleted at 13000 RPM in a table top centrifuge at 4° C. for 10 min, and supernatants collected and frozen at −20° C. Samples were resolved on 4%-12% gradient SDS-PAGE gel in MOPS buffer (Thermo-Fisher Scientific, Grand Island, N.Y.) according to manufacturer's protocol. Proteins were transferred to 0.45 micron nitrocellulose transfer membrane and probed with antibody against CD3 zeta (Clone ab40804, Abcam, Cambridge, Mass.). Bands were visualized using Vectastain ABC-AMP reagent kit (Vector Laboratories, Burlingame, Calif.) and images captured on an Odyssey imaging system (LI-COR, Lincoln, Nebr.).

(f) Flow Cytometric Analysis.

For cell staining one million CAR T transduced cells were harvested from culture, washed two times in cold staining buffer and CAR surface expression detected by staining with protein L-biotin conjugate (stock lmg/ml, 1:1000 dilution, GenScript, Piscataway, N.J.) for 30 minutes at 4° C., followed by two washes and staining with streptavidin-PE conjugate for 30 minutes at 4° C. (stock: 1.0 ml, 1:200 dilution, Jackson ImmunoResearch Laboratories, West Grove, Pa.). Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry.

Specific CAR T staining was carried out by incubating cells with 1 μg/ml Fc-tagged-CD19 peptide for 15 minutes at 4° C., followed by incubation with anti-Fc-AF647 F(ab')2 fragment. Flow cytometric analysis was performed on a MACSQuant®10 Analyzer (Miltenyi Biotec), and high resolution plots were generated using FlowJo software (Ashland, Oreg.).

(g) In Vivo Analysis of CAR-T Activity

All animal studies were approved by Jackson Laboratory Animal Care and Use Committee (Sacramento, Calif.). A half million mouse-adapted Raji-luc cells were injected into the tail vein of NSG (NOD.Cg-Prkdc$^{scid}$Il2rg$^{tm1Wjl}$/SzJ) mice. On day 6 following Raji-luc injection, tumor engraftment was measured by i.p. injection of 150 mg/kg luciferin and imaged 10 min later for 40 seconds on a Xenogen IVIS-200 instrument (Caliper Biosciences). Images were analyzed using Living Image, version 4.1, software (Perkin Elmer) and the bioluminescent signal flux for each mouse was expressed as average radiance (photons per second per $cm^2$ per steradian). CAR T cells were administered to mice via tail vein injection on Day 7. Imaging was performed on the indicated days following injection to establish the kinetics of tumor growth and eradication by CAR T cells.

(h) Statistical Analysis

Statistical analysis was performed using GraphPad Prism 7.01 statistical software (La Jolla, Calif.) as indicated in figure legends.

Results

Figure 6:
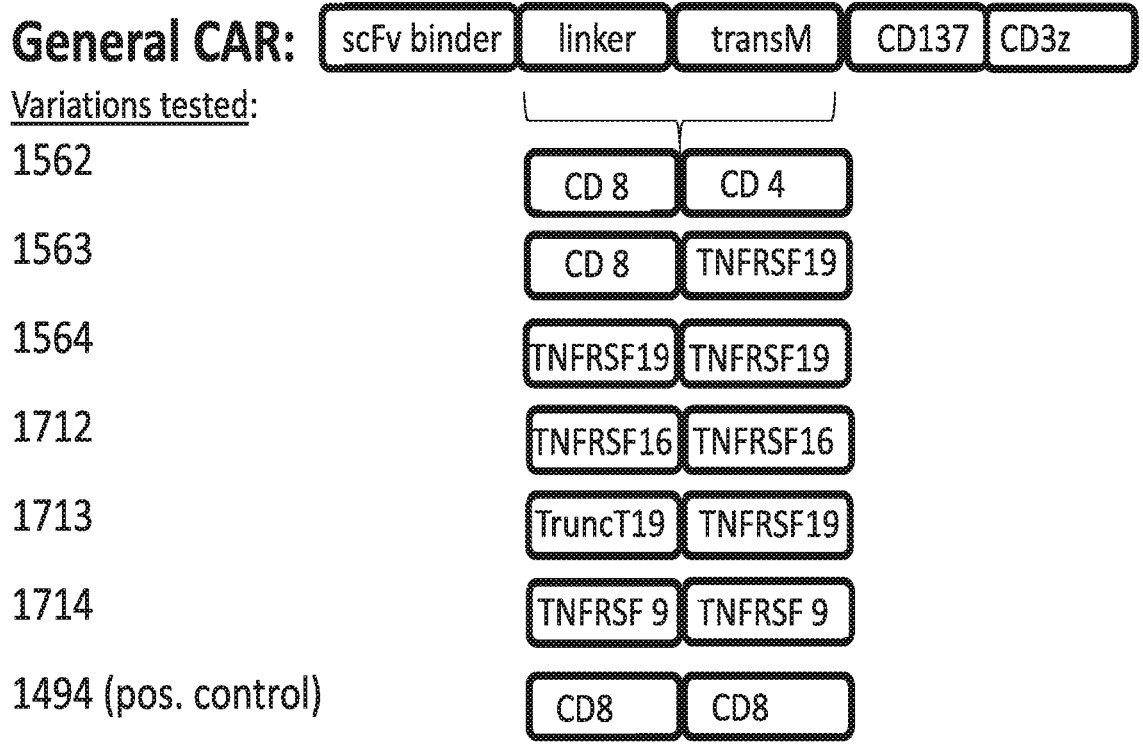
FIG. 6 depicts a diagram of novel linker and transmembrane domain CAR19 constructs. Six CAR19 constructs termed 1562, 1563, 1564 and 1712, 1713 and 1714, incorporating novel linker and transmembrane domain elements, were designed in order to determine whether altering CAR T linker and transmembrane domain composition alters CAR-T function. Construct 1494 denotes a CAR19 configuration comprised of FMC63 scFv binding domain, CD8 linker, CD8 transmembrane domain, CD137/4-1BB and CD3 zeta signaling domains, and serves as a positive control. "transM" refers to the transmembrane domain. "TruncT19" refers to a truncated TNFRSF19 linker in comparison to the extended version present in construct 1564.
Figure 7:
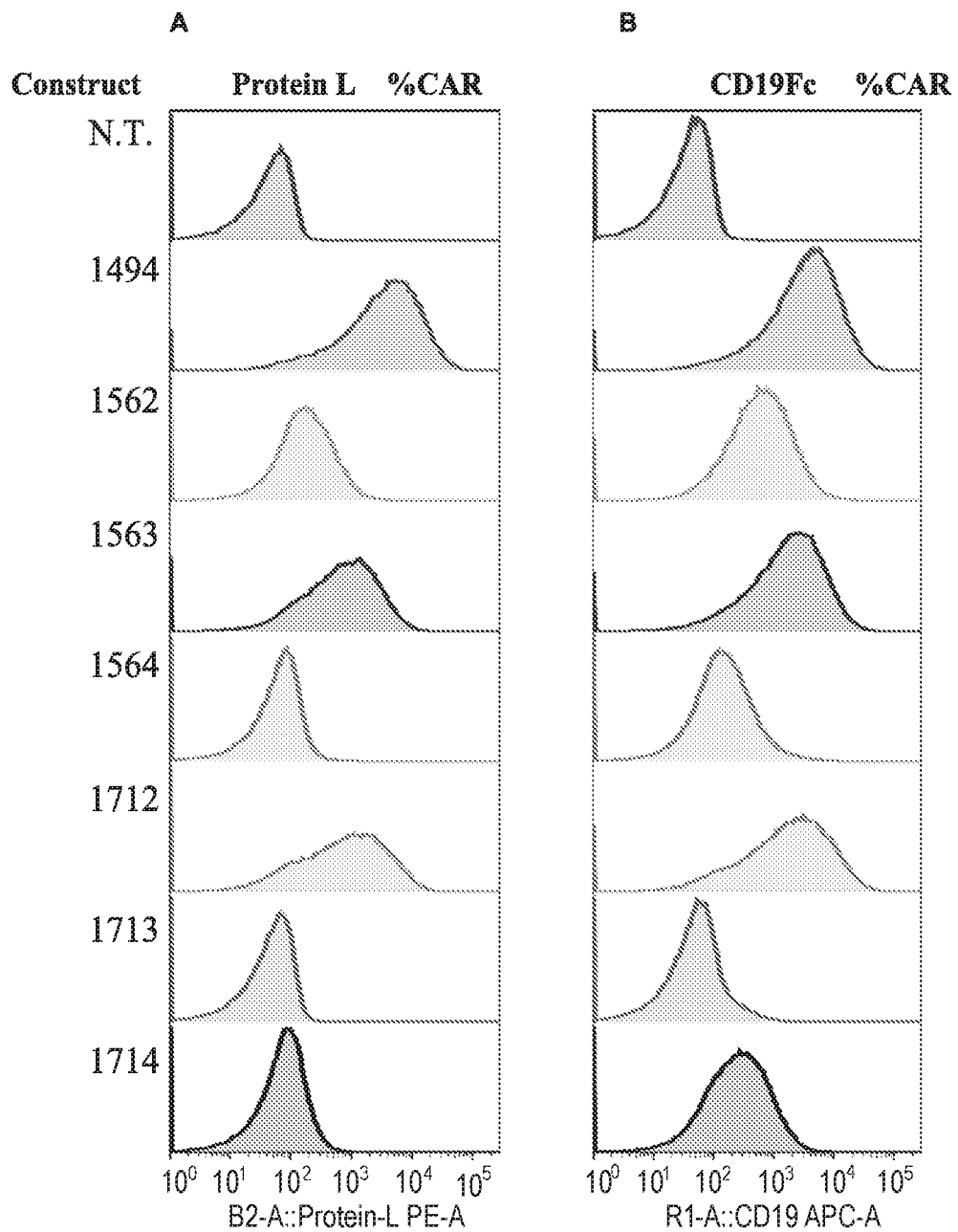
FIG. 7 depicts CAR19 surface expression in human T cells as determined by A) Protein L or B) CD19 Fc staining. Six novel CAR19 constructs and the construct 1494, were stably expressed in human primary T cells by LV transduction. Percentage CAR on T cell surface was determined by flow cytometry using either staining with protein L conjugated to biotin, followed by incubation with streptavidin-PE (left column), or staining with CD19 Fc peptide followed by F(ab)2 anti-Fc reagent conjugated to AF647 (detected in the APC channel). N.T., non-transduced T cells, were used as a negative control.

To investigate the role of transmembrane and linker domains in the function of CAR T cells transmembrane and linker elements derived from protein members of tumor necrosis factor receptor superfamily (TNFRSF) were incorporated in CAR 19 design (FIG. 6 and Table 3).

TABLE 3

Composition of CAR constructs

| Construct number | CD19 scFv domain | Linker domain | Trans-membrane domain | Signaling domains |
|---|---|---|---|---|
| 1562 | FMC63 | CD8 | CD4 | 4-1BB/CD3z |
| 1563 | FMC63 | CD8 | TNFRSF19 | 4-1BB/CD3z |
| 1564 | FMC63 | TNFRSF19 | TNFRSF19 | 4-1BB/CD3z |
| 1712 | FMC63 | TNFRSF16 | TNFRSF16 | 4-1BB/CD3z |
| 1713 | FMC63 | Truncated TNFRSF19 | TNFRSF19 | 4-1BB/CD3z |
| 1714 | FMC63 | *TNFRSF9 | *TNFRSF9 | 4-1BB/CD3z |
| 1494 (positive control) | FMC63 | CD8 | CD8 | 4-1BB/CD3z |
| GFP (negative control) | N/A | N/A | N/A | N/A |

*Please note that TNFRSF9 is an alternative name for CD137 (4-1BB)

Construct 1494 was based on published sequences and used as a positive control and comparator. Construct 1494 is comprised of the murine anti-CD19 scFv sequence, derived from the FMC63 antibody, linked in frame to the linker and transmembrane domain of human CD8-alpha (CD8-a), and the intracellular CD137 (4-1BB) activation domain, followed by the CD247 (CD3-zeta) signaling domain as in Materials and Methods. For each test construct, either the CD8 linker, the CD8 transmembrane domain, or both were substituted with the alternative sequences as described in Table 3. To generate constructs with substituted transmembrane domains, the CD8 transmembrane domain of construct 1494 were replaced with sequences forming the transmembrane helix in CD4, TNFRSF19, TNFRSF16, or TNFRSF9. The role of disulfide bond formation in CART function remains to be fully elucidated. For each novel linker design, structural complexity was reduced by incorporating short fragments of the native ectodomains. This approach gave rise to constructs 1564, 1712, 1714, whose linkers contain 4, 0 and 1 cysteine residues, respectively. To further minimize the potential for disulfide bond formation in construct 1564, construct 1713 was designed with a truncated TNFRSF19 linker to include only one cysteine residue.

To evaluate expression of CAR19 constructs, each construct was produced as a lentiviral vector (LV), and human primary T cells were transduced with LV as described in Materials and Methods. On day 10 after transduction, CAR T cells were analyzed for surface CAR19 expression by flow cytometry (FIG. 6). Two distinct staining methods were evaluated in parallel in order to identify the most sensitive and specific method for CAR19 surface detection. Protein L staining exploits the affinity of bacterial protein L to all immunoglobulin kappa light chains comprising the scFv. Protein L thus cannot differentiate CAR target antigen specificity, and often displays varying affinity to different CARTs. On the other hand, CD19 Fc peptide-binding is based on the binding of the CAR anti-CD19 scFv domain to the target CD19 protein at the T cell surface. Thus, staining with this reagent is both target-specific, and requires the proper conformation of scFv for binding. Protein L staining demonstrated varying degree of CAR T expression in the constructs presented here, ranging from 90.4% for construct 1494 to 0.3% for construct 1713 (FIG. 6). By contrast, staining with CD19Fc peptide yielded better sensitivity, and CART expression ranged from 94.2%-6.86%. Therefore, the CD19 Fc staining is more sensitive than protein L staining, is more uniform, and avoids construct-specific bias. Flow cytometry analysis demonstrates that all CAR19 constructs are expressed on the surface of human T cells transduced with CAR-encoding LV.

Flow cytometry CAR expression data was validated by an alternative method, Western blot, to also demonstrate that the expressed constructs correspond to the predicted molecular weight. Western blot analysis demonstrated strong bands for each tested construct when probed with an anti-CD3 zeta antibody, which also revealed a second strong band for the lower molecular weight native CD3-zeta chain (not illustrated). Lysates from CAR transduced T cells were resolved on denaturing 4-12% SDS-PAGE gel and probed with an antibody for CD3 zeta. GFP-transduced T cells and non-transduced T cells (N.T.) were used as negative controls. Native CD3 zeta was detected in all samples and had an approximate molecular weight of 16 kDa, as predicted. All CAR T constructs produced immunoreactive bands of the predicted molecular weight of 58 kDa. Additional bands seen in some of the lanes may represent post-translational modifications of the CAR T proteins, or residual non-denatured dimers of native CD3 zeta (notable in constructs 1712, 1714). Importantly, all CAR T constructs yielded a band of the predicted size of 58 kDa, thus corroborating the finding that all CARs were expressed in the human primary T cells.

Figure 8:
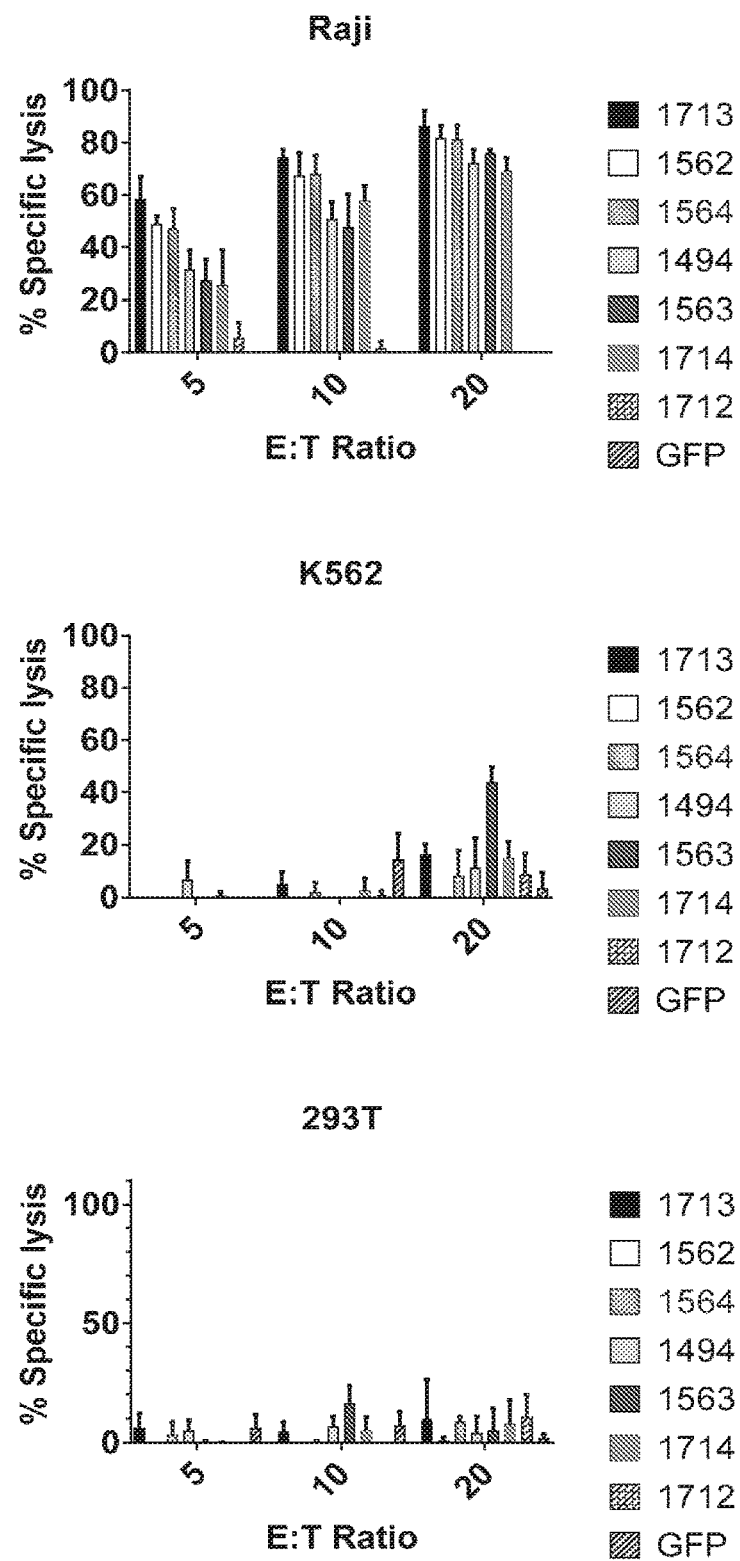
FIG. 8 depicts novel transmembrane CAR19s that demonstrate in vitro leukemia cell killing activity. In vitro killing activity of CAR T cells was evaluated by co-culturing CAR T cells with CD19-positive (Raji) and CD19-negative (293T, K562) tumor cell lines stably expressing firefly luciferase at the noted E:T ratios (x-axis). After overnight incubation, cells were lysed and live tumor luminescence from surviving cells quantified. Bars represent mean+SD.

To determine the lytic potential of the CAR T constructs, Raji CD19-positive lymphoma, which stably expressed firefly luciferase, were employed in an in vitro killing assay (FIG. 8). CAR T cells were combined with Raji-Luc cells at effector to target ratios of 5:1, 10:1 and 20:1 and incubated overnight in 96-wells, then cultures were harvested and analyzed for the residual luciferase activity, indicative of the surviving live Raji tumor cells. Two CD19-negative lines stably expressing luciferase, K562 and 293T were used as negative controls. The results demonstrate a clear ranking of lytic potency within the CAR19 LV tested. Construct 1713 was the most potent, followed by 1562 and 1564. Constructs 1563, 1714 and the positive control 1494 showing similar killing capacity. Unexpectedly, construct 1712 had no specific lytic activity against Raji cells, despite high expression levels (86.4% and 86.9% by Protein L and CD19 Fc staining respectively). Similarly, the negative control GFP showed no specific lysis of the tumor line.

Figure 9:
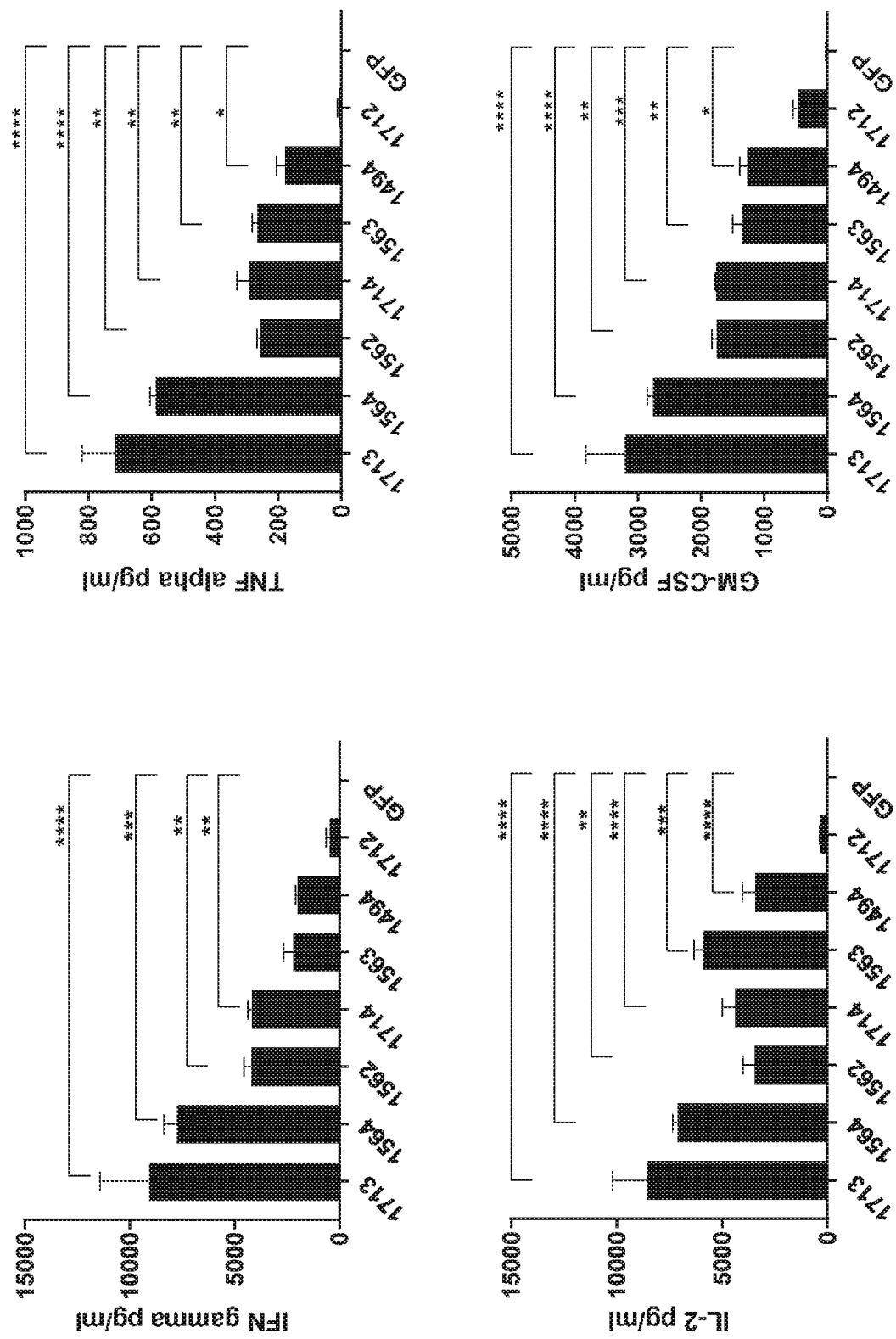
FIG. 9 depicts novel transmembrane CAR19 constructs that demonstrate tumor-specific cytokine response in vitro. Cytokine secretion analysis was performed on supernatants from CAR T challenged overnight with Raji tumor cells at E:T ratio 10:1. Cytokines in supernatants were measured by MACSPlex array (Miltenyi Biotec). Bars represent average of two replicates+SD. Statistical analysis was carried out on GraphPad Prizm software Sample means were compared by 1-Way ANOVA with Dunnett's post-hoc test, *$p<0.05$, $p<0.01$, *$p<0.001$, ****$p<0.0001$.

The magnitude of the induction of type I cytokines IFN gamma, IL-2, TNF alpha and GM-CSF in CAR19 cells co incubated with the CD19-positive Raji lymphoma was then measured. CAR T cells and Raji cells were combined at 10:1 effector to target ratio overnight, and culture supernatants were analyzed by human MACSPlex bead array (FIG. 9). As with the in vitro killing assay, cytokine induction followed a clear rank order, with construct 1713 yielding the highest concentrations of induced cytokines, and the novel transmembrane domain constructs producing more cytokines than the control 1494 construct, the non-lytic construct 1712, and the negative control GFP.

Figure 10:
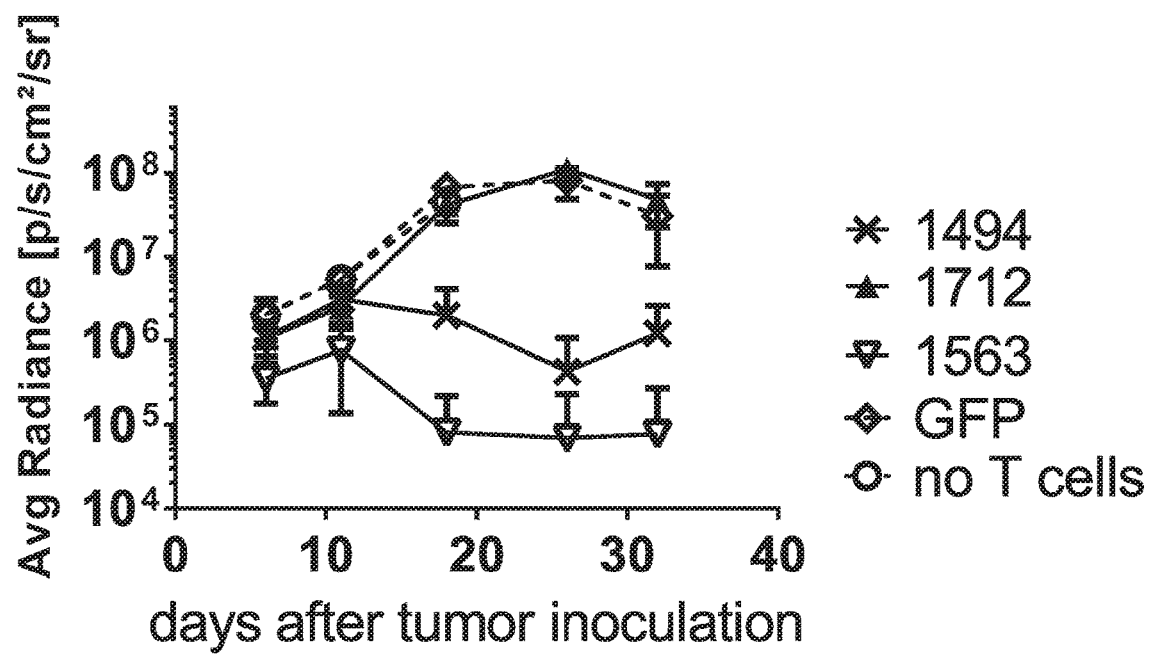
FIG. 10 depicts novel transmembrane CAR construct 1563 that is efficient in eliminating established disseminated Burkitt's lymphoma tumors in NSG mice. A. NSG mice were inoculated with half million Raji cells stably expressing firefly luciferase on day 0, and tumor engraftment was verified on day 6. Then, mice were distributed into groups based on bioluminescence and were dosed with 10 million CAR T cells via tail vein on day 7. Tumor burden was evaluated by bioluminescence up to day 32. Construct 1563 was more efficient than 1494 in Raji tumor elimination in this model.

The antitumor activity of novel transmembrane domain CAR19 constructs in vivo was then measured (FIG. 10). NSG mice were implanted with Raji-luc tumor cells on day 0. Then, on study day 6 tumor engraftment verified by bioluminescence imaging. Mice were randomized to obtain groups with similar tumor burden, and CAR T cells bearing novel transmembrane domains, CAR 1563, or CAR 1712, or positive control CAR1494, or negative control GFP-transduced T cells were injected into mice on study day 7. The tumor alone group (No T cells) served as an additional negative control. Kinetic measurements of tumor burden were performed weekly up to study day 32. As averaged radiance results in FIG. 10 demonstrate, CAR construct 1712, which showed no tumor lysis or cytokine induction in in vitro assays, also failed to alleviate Raji tumor burden in NSG mice, and resulted in tumor average radiance similar to the negative control groups GFP and no T cells over the time course of measurement. Furthermore, the positive control CAR19 construct 1494 was able to reduce, but not completely alleviate tumor growth in this aggressive lymphoma model. Importantly and unexpectedly, only the novel transmembrane domain construct 1563 was able to fully control Raji tumor growth starting from study day 18 and onwards.

Figure 11A:
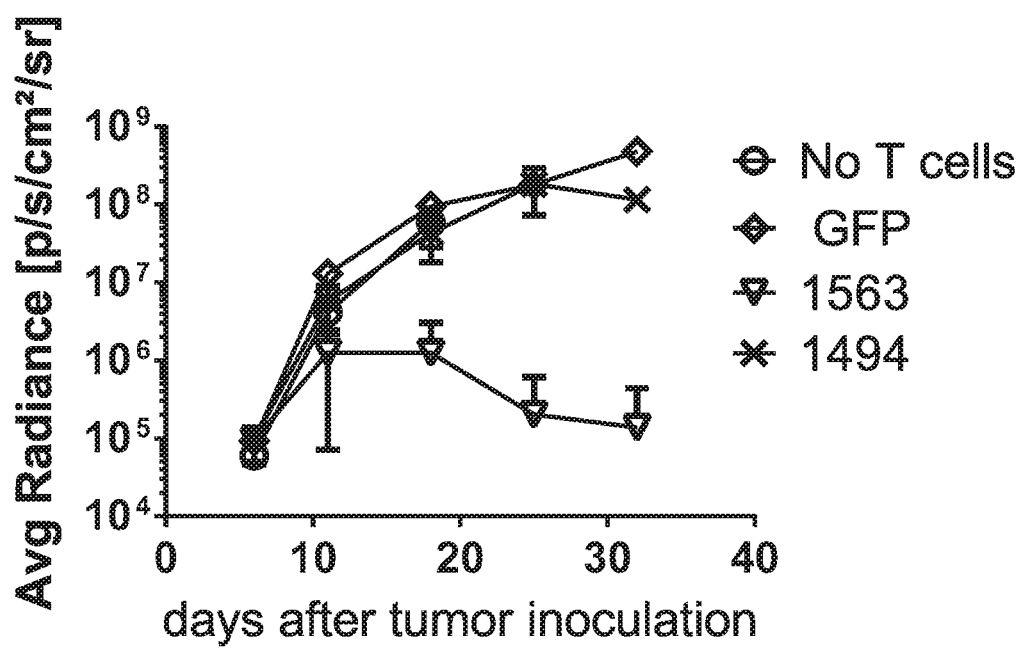
FIGS. 11A and 11B depict an in vivo study repeated with CAR T cells generated from a different T cell donor. Study was performed as in FIG. 10 above.
Figure 11B:
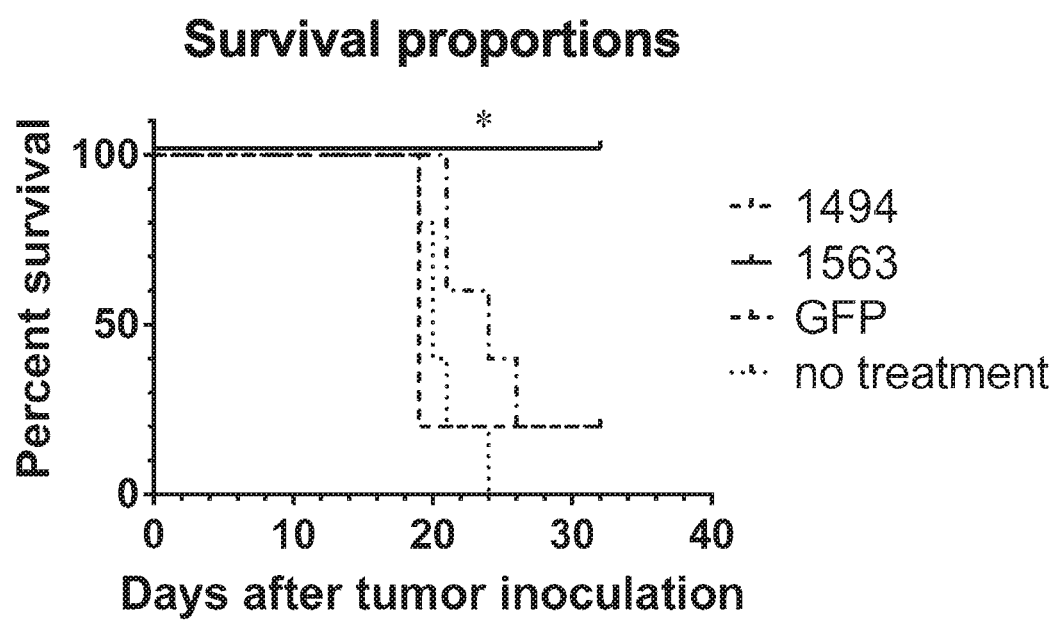

To confirm the in vivo findings in FIG. 10, and to rule out possible donor-to donor variability, the NSG model experiment was repeated with CAR T cells generated from a different human donor, using same experimental protocol (FIG. 11A). Here again, mice bearing bioluminescent Raji tumors were treated with either construct 1494, 1563, GFP, or no T cells. As before, construct 1563 was only able to control Raji tumor progression. It is noteworthy that these experiments were carried out with the more resistant Raji cell line, as opposed to the NALM-6 cell line commonly used in other reports. Thus, the assay employed is far more stringent and may have greater predictive power for relapsed or treatment-resistant human disease. Unexpectedly, in this experiment the positive control construct 1494 was not able to reduce Raji tumor burden below the level of the negative controls, GFP or the "No T cells" treatment (FIG. 11A). Furthermore, Kaplan-Meier survival analysis of mice in this experiment demonstrates a significant difference in survival between construct 1563, and either 1494, or any of the two negative controls, as determined by Log-rank Mantel-Cox test (FIG. 11B). The median survival was: for construct 1563—undetermined (i.e., all mice in this group survived for the duration of the study), for the GFP negative control—19 days, for "No Treatment" group—20 days, and for construct 1494-24 days from study day 0.

In conclusion, these results have demonstrated here that the novel transmembrane domain CAR19 constructs can be successfully expressed in human primary T cells, as evidenced by flow cytometry and Western blotting. Furthermore, the novel transmembrane domain CAR19-bearing T cells are functional in vitro and exhibit a superior functional profile as compared to the control construct 1494. Consequently, the novel transmembrane construct 1563, performed consistently better than the positive control (construct 1494) in controlling established disseminated Raji lymphoma tumors in NSG mouse model in two independent in vivo studies, employing CAR T cells originating from two separate human donors. These findings demonstrate the superiority of a number of CAR19 constructs incorporating transmembrane and/or linker domains derived from the TNFRSF notably, 19 and 9, over the previously described CAR19 construct based on CD8-a transmembrane and linker domains (i.e., CAR construct-1494). Unexpectedly, construct 1712 in which transmembrane and linker domains from TNFRSF16 were used instead of CD8a sequences, demonstrated neither cytolytic activity nor cytokine induction in vitro, and was inefficient in controlling tumors in vivo, despite being highly expressed on T cells. Therefore, the improvement of CAR19 function by substitution of linker or transmembrane domains was an unexpected finding indicating that not all transmembrane regions behave consistently across all type I and type II transmembrane glycoproteins, even within in a single superfamily sub-type such as the TNFRSF, to produce a functional CAR exhibiting in vitro and in vivo activity.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

REFERENCE TO THE SEQUENCE LISTING

This application contains a Sequence Listing electronically submitted to the United States Patent and Trademark Office via a PDF file entitled "Sequence Listing". The Sequence Listing is incorporated by reference.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 is the nucleotide sequence of TNSRFS 16 transmembrane
accgataacctgattccggtgtattgcagcattctggcggcggtggtggtgggcctggtg
gcgtatattgcgtttaaacgctgg SEQ ID NO: 2 is the amino acid sequence of TNFRSF16 transmembrane:
TDNLIPVYCSILAAVVVGLVAYIAFKRW SEQ ID NO: 3 is the nucleotide sequence of TNSRFS 19 transmembrane
gataccgcgctggcggcggtgatttgcagcgcgctggcgaccgtgctgctggcgctgctg
attctgtgcgtgatttattgcaaacgccag SEQ ID NO: 4 is the amino acid sequence of TNSRFS 19 transmembrane
DTALAAVICSALATVLLALLILCVIYCKRQ SEQ ID NO: 5 is the nucleotide sequence of leader/signal peptide sequence
atgctgctgctggtgaccagcctgctgctgtgcgaactgccgcatccggcgtttctgctgattccg SEQ ID NO: 6 is the amino acid sequence of leader/signal peptide sequence
MLLLVTSLLLCELPHPAFLLIP
```

SEQ ID NO: 7 is the nucleotide sequence of SP-CD19binder-CD8link-TNFRSF19tm-signals LTG1563 (FIG. 3D)

atgctgctgctggtgaccagcctgctgctgtgcgaactgccgcatccggcgtttctgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgctttagcggcagcggcagcggcaccgattatagcctgaccattagcaacctg gaacaggaagatattgcgacctatttttgccagcagggcaacacccctgccgtataccttt ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtttctgaaaatgaacagcctgcagaccgatgataccgcgatttattattgcgcg aaacattattattatggcggcagctatgcgatggattattggggccagggcaccagcgtg accgtgagcagcgcggcggcgccggcgccgcgcccgccgaccccggcgccgaccattgcg agccagccgctgagcctgcgcccggaagcgtgccgcccggcggcgggcggcgcggtgcat acccgcggcctggattagataccgcgctggcggcggtgatttgcagcgcgctggcgacc gtgctgctggcgctgctgattctgtgcgtgatttattgcaaacgccagccgcgccgcaaa aaactgctgtatatttttaaacagccgtttatgcgcccggtgcagaccacccaggaagaa gatggctgcagctgccgctttccggaagaagaagaaggcggctgcgaactgcgcgtgaaa tttagccgcagcgcggatgcgccggcgtatcagcagggccagaaccagctgtataacgaa ctgaacctgggccgccgcgaagaatatgatgtgctggataaacgccgcggccgcgatccg gaaatgggcggcaaaccgcgccgcaaaaacccgcaggaaggcctgtataacgaactgcag aaagataaaatggcggaagcgtatagcgaaattggcatgaaaggcgaacgccgccgcggc aaaggccatgatggcctgtatcagggcctgagcaccgcgaccaaagatacctatgatgcg ctgcatatgcaggcgctgccgccgcgc SEQ ID NO: 8 is the amino acid sequence of SP-CD19binder-CD8link-TNFRSF19tm-signals LTG1563 (FIG. 3D)

*MLLLVTSLLLCELPHPAFLLI*PDIQMTQTTSSLSASLGD

*RVTISCRASQDISKYLNWYQQKPDGTVKLLIYHTSRLHSGVPSRFSGSGS*

*GTDYSLTISNLEQEDL4TYFCQQGNTLPYTFGGGTKLEITGGGGSGGGGS*

*GGGGSEVKLQESGPGLVAPSQSLSVTCTVSGVSLPDYGVSWIRQPPRKGL*

*EWLGVIWGSETTYYNSALKSRLTIIKDNSKSQVFLICAINSLQTDDTAIYYC*

*AKHYYYGGSYAMDYWGQGTSVTVSS*AAAPAPRPPTPAPTIASQPLSLRPE

ACRPAAGGAVHTRGLDF<u>DTALAAVICSALATVLLALLILCVIYCKRQPRR

KKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYN

EL

QKDKMAEAYSEIGMKGERRRGKGHDGLYQGLSTATKDTYDALHMQALP

PR

SEQ ID NO: 9 is the nucleotide sequence of SP-CD19binder-TNFRSF19link-
TNFRSF19tm-signals LTG1564 (FIG. 3E)
atgctgctgctggtgaccagcctgctgctgtgcgaactgccgcatccggcgtttctgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgctttagcggcagcggcagcggcaccgattatagcctgaccattagcaacctg gaacaggaagatattgcgacctattttttgccagcagggcaacaccctgccgtataccttt ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtttctgaaaatgaacagcctgcagaccgatgataccgcgatttattattgcgcg aaacattattattatggcggcagctatgcgatggattattggggccagggcaccagcgtg accgtgagcagcgcggcggcggtgggctttcaggatatggaatgcgtgccgtgcggcgat ccgccgccgccgtatgaaccgcattgcgcgagcaaagtgaacctggtgaaaattgcgagc accgcgagcagcccgcgcgataccgcgctggcggcggtgatttgcagcgcgctggcgacc gtgctgctggcgctgctgattctgtgcgtgatttattgcaaacgccagccgcgccgcaaa aaactgctgtatatttttaaacagccgtttatgcgcccggtgcagaccacccaggaagaa gatggctgcagctgccgctttccggaagaagaagaaggcggctgcgaactgcgcgtgaaa tttagccgcagcgcggatgcgccggcgtatcagcagggccagaaccagctgtataacgaa ctgaacctgggccgccgcgaagaatatgatgtgctggataaacgccgcggccgcgatccg gaaatgggcggcaaaccgcgccgcaaaaacccgcaggaaggcctgtataacgaactgcag aaagataaaatggcggaagcgtatagcgaaattggcatgaaaggcgaacgccgccgcggc aaaggccatgatggcctgtatcagggcctgagcaccgcgaccaaagatacctatgatgcg ctgcatatgcaggcgctgccgccgcgc SEQ ID NO: 10 is the amino acid sequence of SP-CD19binder-TNFRSF19link-
TNFRSF19tm-signals LTG1564 (FIG. 3E)
*MLLLVTSLLLCELPHPAFLLIPDIQMTQTTSSLSASLGD*

*RVTISCRASQDISKYLNWYQQKPDGTVKLLIYHTSRLHSGVPSRFSGSGS*

*GTDYSLTISNLEQEDLATYFCQQGNTLPYTFGGGTKLEITGGGGSGGGGS*

*GGGGSEVKLQESGPGLVAPSQSLSVTCTVSGVSLPDYGVSWIRQPPRKGL*

*EWLGVIWGSETTYYNSALKSRLTIIKDNSKSQVFLICAINSLQTDDTAIYYC*

*AKHYYYGGSYAMDYWGQGTSVTVSSAAAVGFQDMECVPCGDPPPPYEPHC*

ASKVNLVKIASTASSPRD<u>TALAAVICSALATVLLALLILCVIYC</u>KRQPRR

KKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYN

EL

QKDKMAEAYSEIGMKGERRGKGHDGLYQGLSTATKDTYDALHMQALP

PR

SEQ ID NO.: 11 is the nucleotide sequence of DNA CD8 transmembrane domain
atctacatct gggcgccctt ggccgggact tgtggggtcc ttctcctgtc actggttatc acccttact gc SEQ ID NO. 12 is the amino acid sequence of CD8 transmembrane domain
Ile Trp Ala Pro Leu Ala Gly Thr Cys Gly Val Leu Leu Leu Ser Leu
Val Ile Thr Leu Tyr Cys SEQ ID NO: 13 is the nucleotide sequence of DNA CD8 hinge domain
accacgacgc cagcgccgcg accaccaaca ccggcgccca ccatcgcgtc gcagcccctg
tccctgcgcc cagaggcgtg ccggccagcg gcggggggcg cagtgcacac gagggggctg
gacttcgcct gtgat SEQ ID NO: 14 is the amino acid sequence of CD8 hinge domain
Thr Thr Thr Pro Ala Pro Arg Pro Pro Thr Pro Ala Pro Thr Ile Ala
Ser Gln Pro Leu Ser Leu Arg Pro Glu Ala Cys Arg Pro Ala Ala Gly
Gly Ala Val His Thr Arg Gly Leu Asp Phe Ala Cys Asp Ile Tyr SEQ ID NO: 15 is the amino acid sequence of amino acid numbers 118 to 178
hinge region of CD8.alpha. (NCBI RefSeq: NP.sub.--001759.3)
Lys Arg Gly Arg Lys Lys Leu Leu Tyr Ile Phe Lys Gln Pro Phe Met
Arg Pro Val Gln Thr Thr Gln Glu Glu Asp Gly Cys Ser Cys Arg Phe
Pro Glu Glu Glu Gly Gly Cys Glu Leu SEQ ID NO: 16 is the amino acid sequence of Human IgG CL sequence
Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser SEQ ID NO 17 is the nucleotide sequence of DNA signaling domain of 4-1BB
aaacggggca gaaagaaact cctgtatata ttcaaacaac catttatgag accagtacaa
actactcaag aggaagatgg ctgtagctgc cgatttccag aagaagaaga aggaggatgt
gaactg SEQ ID NO: 18 is the amino acid sequence of signaling domain of 4-1BB
Lys Arg Gly Arg Lys Lys Leu Leu Tyr Ile Phe Lys Gln Pro Phe Met
Arg Pro Val Gln Thr Thr Gln Glu Glu Asp Gly Cys Ser Cys Arg Phe
Pro Glu Glu Glu Gly Gly Cys Glu Leu SEQ ID NO: 19 is the nucleotide sequence of DNA signaling domain of CD3-
zeta
agagtgaagt tcagcaggag cgcagacgcc cccgcgtaca agcagggcca gaaccagctc tataacgagc tcaatctagg acgaagagag gagtacgatg ttttggacaa gagacgtggc cgggaccctg agatggggggg aaagccgaga aggaagaacc ctcaggaagg cctgtacaat gaactgcaga agataagat ggcggaggcc tacagtgaga ttgggatgaa aggcgagcgc cggaggggca aggggcacga tggcctttac cagggtctca gtacagccac caaggacacc tacgacgccc ttcacatgca ggccctgccc cctcgc SEQ ID NO: 20 is the amino acid sequence of CD3zeta
Arg Val Lys Phe Ser Arg Ser Ala Asp Ala Pro Ala Tyr Lys Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg SEQ ID NO: 21 is the nucleotide sequence of Nucleic acid sequence (DNA) SP-
CD19binder-CD8link-CD4tm-signals LTG1562
atgctgctgctggtgaccagcctgctgctgtgcgaactgccgcatccggcgtactgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgcatagcggcagcggcagcggcaccgattatagcctgaccattagcaacctg gaacaggaagatattgcgacctatattgccagcagggcaacaccctgccgtatacct ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtactgaaaatgaacagcctgcagaccgatgataccgcgatttattattgcgcg aaacattattattatggcggcagctatgcgatggattattggggccagggcaccagcgtg accgtgagcagcgcggcggcgccggcgccgcgcccgccgaccccggcgccgaccattgcg agccagccgctgagcctgcgcccggaagcgtgccgccggcggcgggcggcgcggtgcat acccgcggcctggattagtgcagccgatggcgctgattgtgctgggcggcgtggcgggc ctgctgctgatattggcctgggcatatatagcgtgcgctgccgcccgcgccgcaaa aaactgc tgtatatititaaacagccgtaatgcgcccggtgcagaccacccaggaagaa gatggctgcagc tgccgctttccggaagaagaagaaggcggctgcgaactgcgcgtgaaa tttagccgcagcgc ggatgcgccggcgtatcagcagggccagaaccagctgtataacgaa ctgaacctgggccgcc gcgaagaatatgatgtgctggataaacgccgcggccgcgatccg gaaatgggcggcaaacc gcgccgcaaaaacccgcaggaaggcctgtataacgaactgcag aaagataaaatggcggaa gcgtatagcgaaattggcatgaaaggcgaacgccgccgcggc aaaggccatgatggcctgtat cagggcctgagcaccgcgaccaaagataccatatgatgcg ctgcatatgcaggcgctgccgccgcgc SEQ ID NO: 22 is the amino acid sequence of SP-CD19binder-CD8link-CD4tm-signals LTG1562
MLLLVTSLLLCELPHPAFLLIPDIQMTQTTSSLSASLGD

RVTISCRASQDISKYLNWYQQKPDGTVKLLIYHTSRLHSGVPSRFSGSGS

GTDYSLTISNLEQEDL4TYFCQQGNTLPYTFGGGTKLEITGGGGSGGGGS

GGGGSEVKLQESGPGLVAPSQSLSVTCTVSGVSLPDYGVSWIRQPPRKGL

EWLGVIWGSETTYYNSALKSRLTIIKDNSKSQVFLICAINSLQTDDTAIYYC

AKHYYYGGSYAMDYWGQGTSVTVSSAAAPAPRPPTPAPTIASQPLSLRPE

ACRPAAGGAVHTRGLDFVQPMALIVLGGVAGLLLFIGLGIFFCVRCRPRR

KKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYN

EL

QKDKMAEAYSEIGMKGERRRGKGHDGLYQGLSTATKDTYDALHMQALP

PR

SEQ ID NO: 23 is the nucleotide sequence of TNFRSF 19 linker:
ggcgattgcctgccgggcttttatcgcaaaaccaaactggtgggctttcaggatatggaatgcgtgccgtgcggcgat
ccgccgccgccgtatgaaccgcattgcgcgagcaaagtgaac
ctggtgaaaattgcgagcaccgcgagcagcccgcgcgat SEQ ID NO: 24 is the amino acid sequence of TNFRSF 19 linker:
GDCLPGFYRKTKLVGFQDMECVPCGDPPPPYEPHCASKVNLVKIASTASS
PRD*

-continued

SEQ ID NO: 25 is the nucleotide sequence of TNFRSF16 linker:
gaagaaattccggccgctggattacccgcagcaccccgccggaaggcagcgatagcacc
gcgccgagcacccaggaaccggaagcgccgccggaacaggatctgattgcgagcaccgtg
gcgggcgtggtgaccaccgtgatgggcagcagccagccggtggtgacccgcggcaccacc gataac SEQ ID NO: 26 is the amino acid sequence of TNFRSF16 linker:
EEIPGRWITRSTPPEGSDSTAPSTQEPEAPPEQDLIASTVAGVVTTVMGSSQ
PVVTRGTTDN SEQ ID NO: 27 is the nucleotide sequence of Scvf cd 19
gacatccaga tgacacagac tacatcctcc ctgtctgcct ctctgggaga cagagtcacc atcagttgca
gggcaagtca ggacattagt aaatatttaa attggtatca gcagaaacca gatgaactg ttaaactcct
gatctaccat acatcaagat tacactcagg agtcccatca aggttcagtg gcagtgggtc tggaacagat
tattctctca ccattagcaa cctggagcaa aagatattg ccacttactt tgccaacag ggtaatacgc
ttccgtacac gttcggaggg gggaccaagc tggagatcac aggtggcggt ggctcgggcg tggtgggtc
gggtggcggc ggatctgagg tgaaactgca ggagtcagga cctggcctgg tggcgccctc acagagcctg
tccgtcacat gcactgtctc agggtgtctca ttacccgact atggtgtaag ctggattcgc cagcctccac
gaaagggtct ggagtggctg ggagtaatat ggggtagtga aaccacatac tataattcag ctctcaaatc
cagactgacc atcatcaagg acaactccaa gagccaagtt ttcttaaaaa tgaacagtct gcaaactgat
gacacagcca tttactactg tgccaaacat tattactacg gtggtagcta tgctatggac tactggggcc
aaggaacctc agtcaccgtc tcctca SEQ ID NO: 28 is the amino acid sequence of Scvf cd 19
Asp Ile Gln Met Thr Gln Thr Thr Ser Ser Leu Ser Ala Ser Leu Gly Asp Arg Val
Thr Ile Ser Cys Arg Ala Ser Gln Asp Ile Ser Lys Tyr Leu Asn Trp Tyr Gln Gln
Lys Pro Asp Gly Thr Val Lys Leu Leu Ile Tyr His Thr Ser Arg Leu His Ser Gly
Val Pro Ser Arg Phe Ser Gly Ser Gly Ser Gly Thr Asp Tyr Ser Leu Thr Ile Ser
Asn Leu Glu Gln Glu Asp Ile Ala Thr Tyr Phe Cys Gln Gln Gly Asn Thr Leu Pro
Tyr Thr Phe Gly Gly Gly Thr Lys Leu Glu Ile Thr Gly Gly Gly Gly Ser 100 105
110 Gly Gly Gly Gly Ser Gly Gly Gly Gly Ser Glu Val Lys Leu Gln Glu Ser Gly
Pro Gly Leu Val Ala Pro Ser Gln Ser Leu Ser Val Thr Cys Thr Val Ser Gly Val
Ser Leu Pro Asp Tyr Gly Val Ser Trp Ile Arg Gln Pro Pro Arg Lys Gly Leu Glu
Trp Leu Gly Val Ile Trp Gly Ser Glu Thr Thr Tyr Tyr Asn Ser Ala Leu Lys Ser
Arg Leu Thr Ile Ile Lys Asp Asn Ser Lys Ser Gln Val Phe Leu Lys Met Asn Ser
Leu Gln Thr Asp Asp Thr Ala Ile Tyr Tyr Cys Ala Lys His Tyr Tyr Tyr Gly Gly
Ser Tyr Ala Met Asp Tyr Trp Gly Gln Gly Thr Ser Val Thr Val Ser Ser SEQ ID NO: 29 is the nucleotide sequence of SP-CD19binder-CD8link-CD8tm-
signaling LTG1494 (FIG. 3A)
atgctgctgctggtgaccagcctgctgctgtgcgaactgccgcatccggcgtttctgctg
attccggataccgatattcagatgacccagaccaccagcagcctgagcgcgagcctgggc
gatcgcgtgaccattagctgccgcgcgagccaggatattagcaaatatctgaactggtat
cagcagaaaccggatggcaccgtgaaactgctgatttatcataccagccgcctgcatagc
ggcgtgccgagccgctttagcggcagcggcagcggcaccgattatagcctgaccattagc
aacctggaacaggaagatattgcgacctatttttgccagcagggcaacaccctgccgtat
acctttggcggcggcaccaaactggaaattaccggcagcaccagcggcagcggcaaaccg
ggcagcggcgaaggcagcaccaaaggcgaagtgaaactgcaggaaagcggcccgggcctg
gtggcgccgagccagagcctgagcgtgacctgcaccgtgagcggcgtgagcctgccggat
tatggcgtgagctggattcgccagccgccgcgcaaaggcctggaatggctgggcgtgatt -continued

```
tggggcagcgaaaccacctattataacagcgcgctgaaaagccgcctgaccattattaaa gataacagcaaaagccaggtgtttctgaaaatgaacagcctgcagaccgatgataccgcg atttattattgcgcgaaacattattattatggcggcagctatgcgatggattattgggc cagggcaccagcgtgaccgtgagcagcgcggcggcgaccaccaccccggcgccgcgcccg ccgaccccggcgccgaccattgcgagccagccgctgagcctgcgcccggaagcgtgccgc ccggcggcgggcggcgcggtgcatacccgcgcctggattttgcgtgcgatatttatatt tgggcgccgctggcgggcacctgcggcgtgctgctgctgagcctggtgattaccctgtat tgcaaacgcggccgcaaaaaactgctgtatattttaaacagccgtttatgcgcccggtg cagaccacccaggaagaagatggctgcagctgccgctttccggaagaagaagaaggcggc tgcgaactgcgcgtgaaatttagccgcagcgcggatgcgccggcgtatcagcagggccag aaccagctgtataacgaactgaacctgggccgccgcgaagaatatgatgtgctggataaa cgccgcggccgcgatccggaaatgggcggcaaaccgcgccgcaaaaaccgcaggaaggc ctgtataacgaactgcagaaagataaaatggcggaagcgtatagcgaaattggcatgaaa ggcgaacgccgccgcggcaaaggccatgatggcctgtatcagggcctgagcaccgcgacc aaagatacctatgatgcgctgcatatgcaggcgctgccgccgcgc
```

SEQ ID NO: 30 is the amino acid sequence of SP-CD19binder-CD8link-CD8tm-signaling LTG1494 (FIG. 3A)

*MLLLVTSLLLCELPHPAFLLIPDTDIQMTQTTSSLSASLGD*

*RVTISCRASQDISKYLNWYQQKPDGTVKLLIYHTSRLHSGVPSRFSGSGS*

*GTDYSLTISNLEQEDIATYFCQQGNTLPYTFGGGTKLEITGSTSGSGKPG*

*SGEGSTKGEVKLQESGPGLVAPSQSLSVTCTVSGVSLPDYGVSWIRQPPR*

*KGLEWLGVIWGSETTYYNSALKSRLTIIKDNSKSQVFLKMNSLQTDDTAIYYC*

*AKHYYYGGSYAMDYWGQGTSVTVSS*AAATTT*PAPRPPTPAPTIASQPLSLRPE*

ACRPAAGGAVHTRGLDF<u>ACDIYIWAPLAGTCGVLLLSLVITLYCKR</u>GRKKLLY

IFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSE

IGMKGERRRGKGHDGLYQGLSTATKDTYDALHMQALPPR

SEQ ID NO: 31 is the nucleotide sequence of SP-CD19binder-CD8link-CD8tm-signals (LTI re-engineered) (LTG1538) (FIG. 3B)

```
atgctgctgctggtgaccagcctgctgctgtgcgaactgccgcatccggcgtttctgctg attccggatattcagatgacccagaccaccagcagcctgagcgcgagcctgggcgatcgc gtgaccattagctgccgcgcgagccaggatattagcaaatatctgaactggtatcagcag aaaccggatggcaccgtgaaactgctgatttatcataccagccgcctgcatagcggcgtg ccgagccgctttagcggcagcggcagcggcaccgattatagcctgaccattagcaacctg gaacaggaagatattgcgacctattttgccagcagggcaacaccctgccgtatacctt ggcggcggcaccaaactggaaattaccggcggcggcggcagcggcggcggcggcagcggc ggcggcggcagcgaagtgaaactgcaggaaagcggcccgggcctggtggcgccgagccag agcctgagcgtgacctgcaccgtgagcggcgtgagcctgccggattatggcgtgagctgg attcgccagccgccgcgcaaaggcctggaatggctgggcgtgatttggggcagcgaaacc acctattataacagcgcgctgaaaagccgcctgaccattattaaagataacagcaaaagc caggtgtttctgaaaatgaacagcctgcagaccgatgataccgcgatttattattgcgcg aaacattattattatggcggcagctatgcgatggattattggggccagggcaccagcgtg accgtgagcagcgcggcggcgaccaccaccccggcgccgcgcccgccgaccccggcgccg
```

-continued accattgcgagccagccgctgagcctgcgcccggaagcgtgccgcccggcggcgggcggc gcggtgcatacccgcggcctggattttgcgtgcgatatttatatttgggcgccgctggcg ggcacctgcggcgtgctgctgctgagcctggtgattaccctgtattgcaaacgcggccgc aaaaaactgctgtatatttttaaacagccgtttatgcgcccggtgcagaccacccaggaa gaagatggctgcagctgccgcttccggaagaagaagaaggcggctgcgaactgcgcgtg aaatttagccgcagcgcggatgcgccggcgtatcagcagggccagaaccagctgtataac gaactgaacctgggccgccgcgaagaatatgatgtgctggataaacgccgcggccgcgat ccggaaatgggcggcaaaccgcgccgcaaaaacccgcaggaaggcctgtataacgaactg cagaaagataaaatggcggaagcgtatagcgaaattggcatgaaaggcgaacgccgccgc ggcaaaggccatgatggcctgtatcagggcctgagcaccgcgaccaaagatacctatgat gcgctgcatatgcaggcgctgccgccgcgc SEQ ID NO: 32 is the amino acid sequence of SP-CD19binder-CD8link-CD8tm-signals (LTI re-engineered) (LTG1538) (FIG. 3B)

*MLLLVTSLLLCELPHPAFLLIP*DIQMTQTTSSLSASLGD

*RVTISCRASQDISKYLNWYQQKPDGTVKLLIYHTSRLHSGVPSRFSGSGS*

*GTDYSLTISNLEQEDIATYFCQQGNTLPYTFGGGTKLEITGGGGSGGGGS*

*GGGGSEVKLQESGPGLVAPSQSLSVTCTVSGVSLPDYGVSWIRQPPRKGL*

*EWLGVIWGSETTYYNSALKSRLTIIKDNSKSQVFLKMNSLQTDDTAIYYC*

*AKHYYYGGSYAMDYWGQGTSVTVSS*AAATTTPAPRPPTPAPTIASQPLSLRPE

ACRPAAGGAVHTRGLDF<u>ACDIYIWAPLAGTCGVLLLSLVITLYCKRGRKKLLY</u>

IFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSE

IGMKGERRRGKGHDGLYQGLSTATKDTYDALHMQALPPR

SEQ ID NO: 33 is the nucleotide sequence of SP-CD19binder-TNFRSF16link-TNFRSF16tm-signaling (LTG1712) (FIG. 6)
ATGGGAGCCGGAGCTACTGGACGCGCAATGGACGGACCGAGACTGCT

GCTTCTCCTTCTG

CTGGGCGTGTCCCTTGGCGGTGCCGATATCCAGATGACCCAGACAACC

TCGTCCCTGTCG

GCCAGCCTGGGTGATCGCGTGACCATCTCGTGCCGCGCAAGCCAGGAC

ATCTCAAAGTAT

CTGAACTGGTACCAACAAAAGCCCGACGGGACTGTGAAGCTGCTGATC

TACCACACCTCC

CGACTCCATAGCGGAGTGCCAAGCCGATTCTCCGGTTCCGGCTCTGGA

ACCGATTACTCC

CTGACCATCTCCAACCTGGAGCAGGAGGATATTGCCACCTACTTTTGC

CAGCAGGGGAAC

ACCCTGCCGTACACTTTCGGGGGTGGTACTAAGCTGGAAATCACCGGA

GGCGGAGGAAGC

GGAGGAGGCGGTTCCGGAGGAGGAGGCTCAGAAGTGAAGCTGCAAGA

ATCCGGACCAGGC

TTGGTCGCCCCCTCCCAAAGCCTGTCAGTGACTTGTACCGTGTCGGGA

GTGTCGCTGCCC

GACTACGGCGTGTCCTGGATTAGACAGCCGCCGAGAAAGGGCCTGGA

GTGGCTGGGTGTC

ATTTGGGGCTCCGAAACCACCTACTACAACAGCGCCCTCAAGTCACGG

CTTACCATCATT

AAGGACAACTCCAAGAGCCAAGTGTTTCTCAAGATGAACAGCCTCCAG

ACCGACGACACC

GCCATCTACTACTGTGCTAAGCACTACTACTACGGGGGCTCCTACGCA

ATGGACTACTGG

GGTCAGGGCACCAGCGTGACCGTGTCCTCCGAAGAGATCCCTGGCAGA

TGGATTACACGG

TCTACGCCTCCTGAAGGCTCGGACTCCACTGCCCCGAGCACTCAGGAA

CCGGAAGCCCCT

CCAGAACAGGACTTGATCGCGAGCACTGTGGCCGGGGTGGTCACTACT

GTCATGGGATCG

TCCCAACCTGTGGTGACCCGGGGTACCACTGACAACCTGATCCCCGTC

TACTGCTCGATT

CTCGCAGCCGTCGTGGTCGGCCTGGTGGCATATATCGCATTCAAGAGG

GGCCGGAAGAAG

CTGCTCTACATCTTCAAACAACCATTCATGCGGCCGGTGCAGACTACC

CAGGAGGAGGAC

GGATGTTCGTGCCGCTTCCCGGAAGAGGAAGAGGGCGGATGCGAACT

GAGAGTCAAGTTC

TCGAGATCAGCGGATGCCCCCGCTTACCAGCAGGGACAGAATCAGCTC

TATAACGAGCTG

AACCTTGGCCGGCGGGAAGAGTACGATGTGCTGGATAAGAGAAGAGG

ACGCGATCCCGAG

ATGGGAGGAAAGCCTCGCCGGAAGAACCCGCAGGAAGGCCTGTACAA

CGAGCTTCAGAAG

GACAAGATGGCCGAGGCCTACTCCGAAATCGGAATGAAGGGAGAACG

CAGGCGGGGGAAA

GGCCACGATGGGCTCTACCAGGGTCTTAGCACCGCGACCAAGGACACC

TACGACGCCCTG

CATATGCAAGCGCTTCCTCCACGC

SEQ ID NO: 34 is the amino acid sequence of SP-CD19binder-TNFRSF16link-
TNFRSF16tm-signaling (LTG1712) (FIG. 6)
MGAGATGRAMDGPRLLLLLLLGVSLGGADIQMTQTTSSLSASLGDRVTIS

CRASQDISKY

LNWYQQKPDGTVKLLIYHTSRLHSGVPSRFSGSGSGTDYSLTISNLEQEDI

ATYFCQQGN

TLPYTFGGGTKLEITGGGSGGGGSGGGGSEVKLQESGPGLVAPSQSLSV

TCTVSGVSLP

DYGVSWIRQPPRKGLEWLGVIWGSETTYYNSALKSRLTIIKDNSKSQVFL

KMNSLQTDDT

AIYYCAKHYYYGGSYAMDYWGQGTSVTVSSEEIPGRWITRSTPPEGSDST

APSTQEPEAP

PEQDLIASTVAGVVTTVMGSSQPVVTRGTTDNLIPVYCSILAAVVVGLVA

YIAFKRGRKK

LLYIFKQPFMRPVQTTQEEDGCSCRFPEEEEGGCELRVKFSRSADAPAYQQ

GQNQLYNEL

NLGRREEYDVLDKRRGRDPEMGGKPRRKNPQEGLYNELQKDKMAEAYS

EIGMKGERRRGK

GHDGLYQGLSTATKDTYDALHMQALPPR

SEQ ID NO: 35 is the nucleotide sequence of SP-CD19binder-Truncated
TNFRSF19link-TNFRSF19tm-signaling (LTG1713) (FIG. 6)
ATGGCTCTGAAAGTGCTGTTGGAACAAGAAAAGACCTTCTTCACCTTG

CTCGTGTTGCTG

GGGTACCTGTCCTGCAAAGTCACCTGTGATATCCAGATGACCCAGACA

ACCTCGTCCCTG

TCGGCCAGCCTGGGTGATCGCGTGACCATCTCGTGCCGCGCAAGCCAG

GACATCTCAAAG

TATCTGAACTGGTACCAACAAAAGCCCGACGGGACTGTGAAGCTGCTG

ATCTACCACACC

TCCCGACTCCATAGCGGAGTGCCAAGCCGATTCTCCGGTTCCGGCTCT

GGAACCGATTAC

TCCCTGACCATCTCCAACCTGGAGCAGGAGGATATTGCCACCTACTTTT

GCCAGCAGGGG

AACACCCTGCCGTACACTTTCGGGGGTGGTACTAAGCTGGAAATCACC

GGAGGCGGAGGA

AGCGGAGGAGGCGGTTCCGGAGGAGGAGGCTCAGAAGTGAAGCTGCA

AGAATCCGGACCA

GGCTTGGTCGCCCCCTCCCAAAGCCTGTCAGTGACTTGTACCGTGTCG

GGAGTGTCGCTG

CCCGACTACGGCGTGTCCTGGATTAGACAGCCGCCGAGAAAGGGCCTG

GAGTGGCTGGGT

GTCATTTGGGGCTCCGAAACCACCTACTACAACAGCGCCCTCAAGTCA

CGGCTTACCATC

ATTAAGGACAACTCCAAGAGCCAAGTGTTTCTCAAGATGAACAGCCTC

CAGACCGACGAC

ACCGCCATCTACTACTGTGCTAAGCACTACTACTACGGGGGCTCCTAC

GCAATGGACTAC

TGGGGTCAGGGCACCAGCGTGACCGTGTCCTCCTACGAGCCTCACTGC

GCCAGCAAAGTC

-continued

```
AACTTGGTGAAGATCGCGAGCACTGCCTCGTCCCCTCGGGACACTGCT

CTGGCCGCCGTC

ATTTGCTCGGCGCTCGCAACGGTCCTGCTGGCCCTGCTCATTCTGTGCG

TGATCTACTGC

AAGAGGGGCCGGAAGAAGCTGCTCTACATCTTCAAACAACCATTCATG

CGGCCGGTGCAG

ACTACCCAGGAGGAGGACGGATGTTCGTGCCGCTTCCCGGAAGAGGA

AGAGGGCGGATGC

GAACTGAGAGTCAAGTTCTCGAGATCAGCGGATGCCCCCGCTTACCAG

CAGGGACAGAAT

CAGCTCTATAACGAGCTGAACCTTGGCCGGCGGGAAGAGTACGATGTG

CTGGATAAGAGA

AGAGGACGCGATCCCGAGATGGGAGGAAAGCCTCGCCGGAAGAACCC

GCAGGAAGGCCTG

TACAACGAGCTTCAGAAGGACAAGATGGCCGAGGCCTACTCCGAAAT

CGGAATGAAGGGA

GAACGCAGGCGGGGAAAGGCCACGATGGGCTCTACCAGGGTCTTAG

CACCGCGACCAAG

GACACCTACGACGCCCTGCATATGCAAGCGCTTCCTCCACGC
```

SEQ ID NO: 36 is the amino acid sequence of SP-CD19binder-Truncated
TNFRSF19link-TNFRSF19tm-signaling (LTG1713) (FIG. 6)
```
MALKVLLEQEKTFFTLLVLLGYLSCKVTCDIQMTQTTSSLSASLGDRVTIS

CRASQDISK

YLNWYQQKPDGTVKLLIYHTSRLHSGVPSRFSGSGSGTDYSLTISNLEQED

IATYFCQQG

NTLPYTFGGGTKLEITGGGGSGGGGSGGGGSEVKLQESGPGLVAPSQSLS

VTCTVSGVSL

PDYGVSWIRQPPRKGLEWLGVIWGSETTYYNSALKSRLTIIKDNSKSQVFL

KMNSLQTDD

TAIYYCAKHYYYGGSYAMDYWGQGTSVTVSSYEPHCASKVNLVKIASTA

SSPRDTALAAV

ICSALATVLLALLILCVIYCKRGRKKLLYIFKQPFMRPVQTTQEEDGCSCRF

PEEEEGGC

ELRVKFSRSADAPAYQQGQNQLYNELNLGRREEYDVLDKRRGRDPEMG

GKPRRKNPQEGL

YNELQKDKMAEAYSEIGMKGERRRGKGHDGLYQGLSTATKDTYDALHM

QALPPR
```

SEQ ID NO: 37 is the nucleotide sequence of SP-CD19binder-TNFRSF9link-
TNFRSF9tm-signaling (LTG1714) (FIG. 6)
```
ATGGGAAATTCCTGCTACAACATCGTCGCCACTCTGCTCCTCGTGCTGA

ACTTCGAGAGA

ACTCGCAGCGATATCCAGATGACCCAGACAACCTCGTCCCTGTCGGCC

AGCCTGGGTGAT
```

-continued

```
CGCGTGACCATCTCGTGCCGCGCAAGCCAGGACATCTCAAAGTATCTG

AACTGGTACCAA

CAAAAGCCCGACGGGACTGTGAAGCTGCTGATCTACCACACCTCCCGA

CTCCATAGCGGA

GTGCCAAGCCGATTCTCCGGTTCCGGCTCTGGAACCGATTACTCCCTG

ACCATCTCCAAC

CTGGAGCAGGAGGATATTGCCACCTACTTTTGCCAGCAGGGGAACACC

CTGCCGTACACT

TTCGGGGGTGGTACTAAGCTGGAAATCACCGGAGGCGGAGGAAGCGG

AGGAGGCGGTTCC

GGAGGAGGAGGCTCAGAAGTGAAGCTGCAAGAATCCGGACCAGGCTT

GGTCGCCCCTCC

CAAAGCCTGTCAGTGACTTGTACCGTGTCGGGAGTGTCGCTGCCCGAC

TACGGCGTGTCC

TGGATTAGACAGCCGCCGAGAAAGGGCCTGGAGTGGCTGGGTGTCATT

TGGGGCTCCGAA

ACCACCTACTACAACAGCGCCCTCAAGTCACGGCTTACCATCATTAAG

GACAACTCCAAG

AGCCAAGTGTTTCTCAAGATGAACAGCCTCCAGACCGACGACACCGCC

ATCTACTACTGT

GCTAAGCACTACTACTACGGGGGCTCCTACGCAATGGACTACTGGGGT

CAGGGCACCAGC

GTGACCGTGTCCTCCCTGGATGGCAAATCCGTGCTTGTGAACGGGACG

AAGGAAAGGGAC

GTGGTCTGTGGACCGAGCCCGGCCGACTTGAGCCCAGGCGCCTCATCC

GTCACTCCCCCT

GCTCCTGCACGGGAGCCTGGTCACAGCCCCCAGATCATTTCGTTCTTCC

TCGCATTGACC

TCCACTGCCCTGCTGTTCCTGCTGTTCTTCCTGACCCTGCGGTTCTCGGT

GGTCAAGAGG

GGCCGGAAGAAGCTGCTCTACATCTTCAAACAACCATTCATGCGGCCG

GTGCAGACTACC

CAGGAGGAGGACGGATGTTCGTGCCGCTTCCCGGAAGAGGAAGAGGG

CGGATGCGAACTG

AGAGTCAAGTTCTCGAGATCAGCGGATGCCCCCGCTTACCAGCAGGGA

CAGAATCAGCTC

TATAACGAGCTGAACCTTGGCCGGCGGGAAGAGTACGATGTGCTGGAT

AAGAGAAGAGGA

CGCGATCCCGAGATGGGAGGAAAGCCTCGCCGGAAGAACCCGCAGGA

AGGCCTGTACAAC
```

```
GAGCTTCAGAAGGACAAGATGGCCGAGGCCTACTCCGAAATCGGAAT

GAAGGGAGAACGC

AGGCGGGGAAAGGCCACGATGGGCTCTACCAGGGTCTTAGCACCGC

GACCAAGGACACC

TACGACGCCCTGCATATGCAAGCGCTTCCTCCACGC

SEQ ID NO: 38 is the amino acid sequence of SP-CD19binder-TNFRSF9link-
TNFRSF9tm-signaling (LTG1714) (FIG. 6)
MGNSCYNIVATLLLVLNFERTRSDIQMTQTTSSLSASLGDRVTISCRASQDI

SKYLNWYQ

QKPDGTVKLLIYHTSRLHSGVPSRFSGSGSGTDYSLTISNLEQEDIATYFCQ

QGNTLPYT

FGGGTKLEITGGGSGGGGSGGGGSEVKLQESGPGLVAPSQSLSVTCTVS

GVSLPDYGVS

WIRQPPRKGLEWLGVIWGSETTYYNSALKSRLTIIKDNSKSQVFLKMNSL

QTDDTAIYYC

AKHYYYGGSYAMDYWGQGTSVTVSSLDGKSVLVNGTKERDVVCGPSPA

DLSPGASSVTPP

APAREPGHSPQIISFFLALTSTALLFLLFFLTLRFSVVKRGRKKLLYIFKQPF

MRPVQTT

QEEDGCSCRFPEEEEGGCELRVKFSRSADAPAYQQGQNQLYNELNLGRRE

EYDVLDKRRG

RDPEMGGKPRRKNPQEGLYNELQKDKMAEAYSEIGMKGERRRGKGHDG

LYQGLSTATKDT

YDALHMQALPPR

SEQ ID NO: 39 is the nucleotide sequence of SP-CD19binder-CD8link-CD4tm-
signaling (LTG1562) (FIG.6)
ATGCTGCTGCTGGTCACCAGCCTGCTGCTGTGCGAGCTCCCTCACCCCG

CCTTTCTGCTT

ATCCCGGACATTCAGATGACACAGACCACCTCGAGCTTGTCCGCGTCG

CTGGGCGATCGC

GTGACCATCTCCTGCCGGGCCTCCCAAGACATTTCAAAGTATCTCAAC

TGGTACCAGCAG

AAGCCGGACGGAACCGTGAAACTGCTGATCTACCATACCAGCCGCCTG

CACTCCGGCGTG

CCGTCCCGCTTCTCCGGATCGGGTTCCGGAACTGACTACTCACTGACTA

TCTCCAACTTG

GAACAAGAGGACATCGCCACTTACTTCTGTCAACAAGGAAATACCCTT

CCCTACACCTTC

GGGGGGGGTACCAAGCTGGAGATCACTGGGGGCGGAGGCTCCGGTGG

AGGCGGATCCGGC

GGTGGAGGGAGCGAAGTCAAGCTGCAGGAATCAGGACCAGGACTCGT

GGCGCCATCCCAG

TCCCTGTCGGTGACCTGTACTGTCTCCGGAGTCAGCCTCCCCGATTACG
```

GAGTGTCATGG

ATTAGGCAACCCCCAAGAAAAGGGCTGGAATGGCTCGGAGTGATCTG

GGGCTCCGAAACC

ACCTACTACAACTCGGCGCTGAAGTCCCGGCTGACCATCATCAAGGAC

AACTCCAAGAGC

CAAGTGTTCTTGAAGATGAACAGCTTGCAGACCGACGATACCGCAATC

TACTACTGTGCC

AAGCACTATTACTACGGGGGGTCTTACGCCATGGACTACTGGGGACAG

GGCACCTCCGTG

ACTGTGTCGTCCGCGGCCGCGCCCGCCCCTCGGCCCCCGACTCCTGCC

CCGACGATCGCT

TCCCAACCTCTCTCGCTGCGCCCGGAAGCATGCCGGCCCGCCGCCGGT

GGCGCTGTCCAC

ACTCGCGGACTGGACTTTGTGCAGCCTATGGCACTGATCGTCCTGGGA

GGAGTGGCCGGA

CTGCTGCTGTTCATTGGGCTCGGAATCTTCTTCTGCGTGCGGTGCCGGC

CTAGGCGAAAG

AAGCTCCTCTACATTTTCAAGCAACCCTTCATGCGCCCCGTGCAAACC

ACCCAGGAGGAG

GATGGATGCTCATGCCGGTTCCCTGAGGAAGAAGAGGGCGGTTGCGA

GCTCAGAGTGAAA

TTCAGCCGGTCGGCTGACGCCCCGGCGTACCAGCAGGGCCAGAACCA

GCTGTACAATGAG

CTCAACCTGGGGCGCCGCGAAGAGTACGACGTGCTGGACAAGAGGAG

AGGCAGAGATCCG

GAAATGGGCGGAAAGCCAAGGCGGAAGAACCCGCAGGAAGGTCTTTA

CAACGAACTGCAG

AAGGACAAGATGGCCGAGGCCTACTCCGAGATTGGGATGAAGGGAGA

AAGACGGAGGGGA

AAGGGACATGACGGACTTTACCAGGGCCTGAGCACTGCCACGAAGGA

CACCTATGATGCC

CTGCACATGCAGGCGCTGCCGCCTCGG

SEQ ID NO: 40 is the nucleotide sequence of SP-CD19binder-CD8link-
TNFRSF19tm-signaling (LTG1563) (FIG. 6)
ATGCTGCTGCTGGTCACCAGCCTGCTGCTGTGCGAGCTCCCTCACCCCG

CCTTTCTGCTT

ATCCCGGACATTCAGATGACACAGACCACCTCGAGCTTGTCCGCGTCG

CTGGGCGATCGC

GTGACCATCTCCTGCCGGGCCTCCCAAGACATTTCAAAGTATCTCAAC

TGGTACCAGCAG

-continued

```
AAGCCGGACGGAACCGTGAAACTGCTGATCTACCATACCAGCCGCCTG

CACTCCGGCGTG

CCGTCCCGCTTCTCCGGATCGGGTTCCGGAACTGACTACTCACTGACTA

TCTCCAACTTG

GAACAAGAGGACATCGCCACTTACTTCTGTCAACAAGGAAATACCCTT

CCCTACACCTTC

GGGGGGGGTACCAAGCTGGAGATCACTGGGGGCGGAGGCTCCGGTGG

AGGCGGATCCGGC

GGTGGAGGGAGCGAAGTCAAGCTGCAGGAATCAGGACCAGGACTCGT

GGCGCCATCCCAG

TCCCTGTCGGTGACCTGTACTGTCTCCGGAGTCAGCCTCCCCGATTACG

GAGTGTCATGG

ATTAGGCAACCCCCAAGAAAAGGGCTGGAATGGCTCGGAGTGATCTG

GGGCTCCGAAACC

ACCTACTACAACTCGGCGCTGAAGTCCCGGCTGACCATCATCAAGGAC

AACTCCAAGAGC

CAAGTGTTCTTGAAGATGAACAGCTTGCAGACCGACGATACCGCAATC

TACTACTGTGCC

AAGCACTATTACTACGGGGGGTCTTACGCCATGGACTACTGGGGACAG

GGCACCTCCGTG

ACTGTGTCGTCCGCGGCCGCGCCCGCCCCTCGGCCCCCGACTCCTGCC

CCGACGATCGCT

TCCCAACCTCTCTCGCTGCGCCCGGAAGCATGCCGGCCCGCCGCCGGT

GGCGCTGTCCAC

ACTCGCGGACTGGACTTTGATACCGCACTGGCGGCCGTGATCTGTAGC

GCCCTGGCCACC

GTGCTGCTGGCGCTGCTCATCCTTTGCGTGATCTACTGCAAGCGGCAG

CCTAGGCGAAAG

AAGCTCCTCTACATTTTCAAGCAACCCTTCATGCGCCCCGTGCAAACC

ACCCAGGAGGAG

GATGGATGCTCATGCCGGTTCCCTGAGGAAGAAGAGGGCGGTTGCGA

GCTCAGAGTGAAA

TTCAGCCGGTCGGCTGACGCCCCGGCGTACCAGCAGGGCCAGAACCA

GCTGTACAATGAG

CTCAACCTGGGGCGCCGCGAAGAGTACGACGTGCTGGACAAGAGGAG

AGGCAGAGATCCG

GAAATGGGCGGAAAGCCAAGGCGGAAGAACCCGCAGGAAGGTCTTTA

CAACGAACTGCAG

AAGGACAAGATGGCCGAGGCCTACTCCGAGATTGGGATGAAGGGAGA

AAGACGGAGGGGA
```

AAGGGACATGACGGACTTTACCAGGGCCTGAGCACTGCCACGAAGGA

CACCTATGATGCC

CTGCACATGCAGGCGCTGCCGCCTCGG

SEQ ID NO: 41 is the nucleotide sequence of SP-CD19binder-TNFRSF19link-
TNFRSF19tm-signaling (LTG1564) (FIG. 6)
ATGCTGCTGCTGGTCACCAGCCTGCTGCTGTGCGAGCTCCCTCACCCCG

CCTTTCTGCTT

ATCCCGGACATTCAGATGACACAGACCACCTCGAGCTTGTCCGCGTCG

CTGGGCGATCGC

GTGACCATCTCCTGCCGGGCCTCCCAAGACATTTCAAAGTATCTCAAC

TGGTACCAGCAG

AAGCCGGACGGAACCGTGAAACTGCTGATCTACCATACCAGCCGCCTG

CACTCCGGCGTG

CCGTCCCGCTTCTCCGGATCGGGTTCCGGAACTGACTACTCACTGACTA

TCTCCAACTTG

GAACAAGAGGACATCGCCACTTACTTCTGTCAACAAGGAAATACCCTT

CCCTACACCTTC

GGGGGGGGTACCAAGCTGGAGATCACTGGGGGCGGAGGCTCCGGTGG

AGGCGGATCCGGC

GGTGGAGGGAGCGAAGTCAAGCTGCAGGAATCAGGACCAGGACTCGT

GGCGCCATCCCAG

TCCCTGTCGGTGACCTGTACTGTCTCCGGAGTCAGCCTCCCCGATTACG

GAGTGTCATGG

ATTAGGCAACCCCCAAGAAAAGGGCTGGAATGGCTCGGAGTGATCTG

GGGCTCCGAAACC

ACCTACTACAACTCGGCGCTGAAGTCCCGGCTGACCATCATCAAGGAC

AACTCCAAGAGC

CAAGTGTTCTTGAAGATGAACAGCTTGCAGACCGACGATACCGCAATC

TACTACTGTGCC

AAGCACTATTACTACGGGGGGTCTTACGCCATGGACTACTGGGGACAG

GGCACCTCCGTG

ACTGTGTCGTCCGCGGCCGCGGTCGGATTCCAAGACATGGAATGCGTG

CCCTGCGGCGAC

CCGCCACCTCCTTACGAGCCGCACTGCGCATCGAAGGTCAACCTCGTG

AAGATCGCGAGC

ACCGCGTCCTCACCCCGGGATACTGCTCTGGCCGCCGTGATTTGTTCCG

CCTTGGCCACC

GTGCTTCTGGCCCTGCTGATCCTCTGTGTGATCTACTGCAAGCGCCAGC

CTAGGCGAAAG

AAGCTCCTCTACATTTTCAAGCAACCCTTCATGCGCCCCGTGCAAACC

ACCCAGGAGGAG

-continued

```
GATGGATGCTCATGCCGGTTCCCTGAGGAAGAAGAGGGCGGTTGCGA

GCTCAGAGTGAAA

TTCAGCCGGTCGGCTGACGCCCCGGCGTACCAGCAGGGCCAGAACCA

GCTGTACAATGAG

CTCAACCTGGGGCGCCGCGAAGAGTACGACGTGCTGGACAAGAGGAG

AGGCAGAGATCCG

GAAATGGGCGGAAAGCCAAGGCGGAAGAACCCGCAGGAAGGTCTTTA

CAACGAACTGCAG

AAGGACAAGATGGCCGAGGCCTACTCCGAGATTGGGATGAAGGGAGA

AAGACGGAGGGGA

AAGGGACATGACGGACTTTACCAGGGCCTGAGCACTGCCACGAAGGA

CACCTATGATGCC

CTGCACATGCAGGCGCTGCCGCCTCGG
```

What is claimed is:

1. A method of treating cancer in a subject in need thereof, the method comprising administering to the subject a pharmaceutical composition comprising an anti-tumor effective amount of a population of T cells, wherein the T cells comprise a nucleic acid sequence that encodes a chimeric antigen receptor (CAR) comprising the amino acid sequence of SEQ ID NO: 8.

2. The method of claim 1, wherein the cancer is a hematological cancer selected from the group consisting of leukemia, lymphoma, and multiple myeloma.

3. The method of claim 2, wherein the leukemia is chronic lymphocytic leukemia (CLL), acute lymphocytic leukemia (ALL), or chronic myelogenous leukemia (CIVIL).

4. The method of claim 2, wherein the lymphoma is mantle cell lymphoma, non-Hodgkin's lymphoma or Hodgkin's lymphoma.

5. The method of claim 1, wherein the cancer is selected from the group consisting of oral and pharynx cancer, a hematological cancer, a digestive system cancer, a respiratory system cancer, a bone and joint cancer, a soft tissue cancer, a skin cancer, a pediatric tumor, a tumor of the central nervous system, a cancer of the breast, a cancer of the genital system, a cancer of the urinary system, a cancer of the eye and orbit, a cancer of the endocrine system, a cancer of the brain and other nervous system, and a combination thereof.

6. The method of claim 1, wherein the nucleic acid sequence that encodes the CAR comprises the nucleic acid sequence of SEQ ID NO: 7, or a sequence with 85%, 90%, 95%, 96%, 97%, 98% or 99% identity thereof.

7. The method of claim 1, wherein the nucleic acid sequence that encodes the CAR comprises the nucleic acid sequence of SEQ ID NO: 40, or a sequence with 85%, 90%, 95%, 96%, 97%, 98% or 99% identity thereof.

8. A method of treating cancer in a subject in need thereof, the method comprising administering to the subject a pharmaceutical composition comprising an anti-tumor effective amount of a population of T cells, wherein the T cells comprise a nucleic acid sequence that encodes a chimeric antigen receptor (CAR) comprising the amino acid sequence of SEQ ID NO: 10.

9. The method of claim 8, wherein the nucleic acid sequence that encodes the CAR comprises the nucleic acid sequence of SEQ ID NO: 9, or a sequence with 85%, 90%, 95%, 96%, 97%, 98% or 99% identity thereof.

10. The method of claim 8, wherein the cancer is a hematological cancer selected from the group consisting of leukemia, lymphoma, and multiple myeloma.

11. The method of claim 10, wherein the leukemia is chronic lymphocytic leukemia (CLL), acute lymphocytic leukemia (ALL), or chronic myelogenous leukemia (CML).

12. The method of claim 10, wherein the lymphoma is mantle cell lymphoma, non-Hodgkin's lymphoma or Hodgkin's lymphoma.

13. The method of claim 8, wherein the cancer is selected from the group consisting of oral and pharynx cancer, a hematological cancer, a digestive system cancer, a respiratory system cancer, a bone and joint cancer, a soft tissue cancer, a skin cancer, a pediatric tumor, a tumor of the central nervous system, a cancer of the breast, a cancer of the genital system, a cancer of the urinary system, a cancer of the eye and orbit, a cancer of the endocrine system, a cancer of the brain and other nervous system, and a combination thereof.

14. A method of treating cancer in a subject in need thereof, the method comprising administering to the subject a pharmaceutical composition comprising an anti-tumor effective amount of a population of T cells, wherein the T cells comprise a nucleic acid sequence that encodes a chimeric antigen receptor (CAR) comprising the amino acid sequence of SEQ ID NO: 36.

15. The method of claim 14, wherein the nucleic acid sequence that encodes the CAR comprises the nucleic acid sequence of SEQ ID NO: 35, or a sequence with 85%, 90%, 95%, 96%, 97%, 98% or 99% identity thereof.

16. The method of claim 14, wherein the cancer is a hematological cancer selected from the group consisting of leukemia, lymphoma, and multiple myeloma.

17. The method of claim 16, wherein the leukemia is chronic lymphocytic leukemia (CLL), acute lymphocytic leukemia (ALL), or chronic myelogenous leukemia (CML).

18. The method of claim 16, wherein the lymphoma is mantle cell lymphoma, non-Hodgkin's lymphoma or Hodgkin's lymphoma.

19. The method of claim 14, wherein the cancer is selected from the group consisting of oral and pharynx cancer, a hematological cancer, a digestive system cancer, a respiratory system cancer, a bone and joint cancer, a soft tissue cancer, a skin cancer, a pediatric tumor, a tumor of the central nervous system, a cancer of the breast, a cancer of the genital system, a cancer of the urinary system, a cancer of the eye and orbit, a cancer of the endocrine system, a cancer of the brain and other nervous system, and a combination thereof.

* * * * *

SEQUENCE LISTING

<160> NUMBER OF SEQ ID NOS: 40

<210> SEQ ID NO 1
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 1

```
accgataacc tgattccggt gtattgcagc attctggcgg cggtggtggt gggcctggtg    60
gcgtatattg cgtttaaacg ctgg                                          84
```

<210> SEQ ID NO 2
<211> LENGTH: 28
<212> TYPE: PRT
<213> ORGANISM: Artificial Sequence
<220> FEATURE:
<223> OTHER INFORMATION: synthetic peptide

<400> SEQUENCE: 2

```
Thr Asp Asn Leu Ile Pro Val Tyr Cys Ser Ile Leu Ala Ala Val Val
1               5                   10                  15

Val Gly Leu Val Ala Tyr Ile Ala Phe Lys Arg Trp
            20                  25
```

<210> SEQ ID NO 3
<211> LENGTH: 90
<212> TYPE: DNA
<213> ORGANISM: Artificial Sequence
<220> FEATURE:
<223> OTHER INFORMATION: synthetic oligonucleotide

<400> SEQUENCE: 3

```
gataccgcgc tggcggcggt gatttgcagc gcgctggcga ccgtgctgct ggcgctgctg    60
attctgtgcg tgatttattg caaacgccag                                     90
```

<210> SEQ ID NO 4
<211> LENGTH: 30
<212> TYPE: PRT

```
<213> ORGANISM: Artificial Sequence
<220> FEATURE:
<223> OTHER INFORMATION: synthetic peptide

<400> SEQUENCE: 4

Asp Thr Ala Leu Ala Ala Val Ile Cys Ser Ala Leu Ala Thr Val Leu
1               5                   10                  15

Leu Ala Leu Leu Ile Leu Cys Val Ile Tyr Cys Lys Arg Gln
            20                  25                  30

<210> SEQ ID NO 5
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 5
atgctgctgc tggtgaccag cctgctgctg tgcgaactgc cgcatccggc gtttctgctg    60
attccg                                                                66

<210> SEQ ID NO 6
<211> LENGTH: 22
<212> TYPE: PRT
<213> ORGANISM: Artificial Sequence
<220> FEATURE:
<223> OTHER INFORMATION: synthetic peptide

<400> SEQUENCE: 6

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 7
<211> LENGTH: 1467
<212> TYPE: DNA
<213> ORGANISM: Artificial Sequence
<220> FEATURE:
<223> OTHER INFORMATION: synthetic oligonucleotide

<400> SEQUENCE: 7
atgctgctgc tggtgaccag cctgctgctg tgcgaactgc cgcatccggc gtttctgctg    60
attccggata ttcagatgac ccagaccacc agcagcctga gcgcgagcct gggcgatcgc   120
gtgaccatta gctgccgcgc gagccaggat attagcaaat atctgaactg gtatcagcag   180
aaaccggatg gcaccgtgaa actgctgatt tatcatacca gccgcctgca tagcggcgtg   240
ccgagccgct ttagcggcag cggcagcggc accgattata gcctgaccat tagcaacctg   300
gaacaggaag atattgcgac ctatttttgc cagcagggca cacccctgcc gtatacccttt   360 ggcggcggca ccaaactgga aattaccggc ggcggcggca gcggcggcgg cggcagcggc   420
ggcggcggca gcgaagtgaa actgcaggaa gcggcccgg gcctggtggc gccgagccag   480
agcctgagcg tgacctgcac cgtgagcggc gtgagcctgc cggattatgg cgtgagctgg   540
attcgccagc cgccgcgcaa aggcctggaa tggctgggcg tgatttgggg cagcgaaacc   600
acctattata cagcgcgct gaaaagccgc ctgaccatta ttaaagataa cagcaaaagc   660
caggtgtttc tgaaaatgaa cagcctgcag accgatgata ccgcgattta ttattgcgcg   720
aaacattatt attatggcgg cagctatgcg atggattatt ggggccaggg caccagcgtg   780
accgtgagca gcgcggcggc gccggcgccg cgcccgccga cccggcgcc gaccattgcg   840
```

```
agccagccgc tgagcctgcg cccggaagcg tgccgcccgg cggcgggcgg cgcggtgcat    900
acccgcggcc tggattttga taccgcgctg gcggcggtga tttgcagcgc gctggcgacc    960
gtgctgctgg cgctgctgat tctgtgcgtg atttattgca aacgccagcc gcgccgcaaa   1020
aaactgctgt atattttaa acagccgttt atgcgcccgg tgcagaccac ccaggaagaa    1080
gatggctgca gctgccgctt ccggaagaa gaagaaggcg gctgcgaact cgcgtgaaa     1140
tttagccgca gcgcggatgc gccggcgtat cagcagggcc agaaccagct gtataacgaa   1200
ctgaacctgg ccgccgcga gaatatgat gtgctggata aacgccgcgg ccgcgatccg     1260
gaaatgggcg gcaaaccgcg ccgcaaaaac ccgcaggaag gcctgtataa cgaactgcag   1320
aaagataaaa tggcggaagc gtatagcgaa attggcatga aaggcgaacg ccgccgcggc   1380
aaaggccatg atggcctgta tcagggcctg agcaccgcga ccaaagatac ctatgatgcg   1440
ctgcatatgc aggcgctgcc gccgcgc                                       1467

<210> SEQ ID NO 8
<211> LENGTH: 489
<212> TYPE: PRT
<213> ORGANISM: Artificial Sequence
<220> FEATURE:
<223> OTHER INFORMATION: synthetic peptide

<400> SEQUENCE: 8

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
```

```
                    245                 250                 255
Gly Thr Ser Val Thr Val Ser Ser Ala Ala Pro Ala Pro Arg Pro
                260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
        290                 295                 300

Asp Phe Asp Thr Ala Leu Ala Ala Val Ile Cys Ser Ala Leu Ala Thr
305                 310                 315                 320

Val Leu Leu Ala Leu Leu Ile Leu Cys Val Ile Tyr Cys Lys Arg Gln
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 9
<211> LENGTH: 1467
<212> TYPE: DNA
<213> ORGANISM: Artificial Sequence
<220> FEATURE:
<223> OTHER INFORMATION: synthetic oligonucleotide

<400> SEQUENCE: 9
atgctgctgc tggtgaccag cctgctgctg tgcgaactgc cgcatccggc gtttctgctg      60
attccggata ttcagatgac ccagaccacc agcagcctga gcgcgagcct gggcgatcgc     120
gtgaccatta gctgccgcgc gagccaggat attagcaaat atctgaactg gtatcagcag     180
aaaccggatg gcaccgtgaa actgctgatt tatcatacca gccgcctgca tagcggcgtg     240
ccgagccgct ttagcggcag cggcagcggc accgattata gcctgaccat tagcaacctg     300
gaacaggaag atattgcgac ctatttttgc agcagggca acaccctgcc gtataccttt     360
ggcggcggca ccaaactgga aattaccggc ggcggcggca gcggcggcgg cggcagcggc     420
ggcggcggca gcgaagtgaa actgcaggaa agcggcccgg gcctggtggc gccgagccag     480
agcctgagcg tgacctgcac cgtgagcggc gtgagcctgc cggattatgg cgtgagctgg     540
attcgccagc cgccgcgcaa aggcctggaa tggctgggcg tgatttgggg cagcgaaacc     600
acctattata cagcgcgct gaaaagccgc ctgaccatta ttaaagataa cagcaaaagc     660
```

```
caggtgtttc tgaaaatgaa cagcctgcag accgatgata ccgcgattta ttattgcgcg    720
aaacattatt attatggcgg cagctatgcg atggattatt ggggccaggg caccagcgtg    780
accgtgagca gcgcggcggc ggtgggcttt caggatatgg aatgcgtgcc gtgcggcgat    840
ccgccgccgc cgtatgaacc gcattgcgcg agcaaagtga acctggtgaa aattgcgagc    900
accgcgagca gcccgcgcga taccgcgctg gcggcggtga tttgcagcgc gctggcgacc    960
gtgctgctgg cgctgctgat tctgtgcgtg atttattgca aacgccagcc gcgccgcaaa   1020
aaactgctgt atatttttaa acagccgttt atgcgcccgg tgcagaccac ccaggaagaa   1080
gatggctgca gctgccgctt tccggaagaa gaagaaggcg gctgcgaact gcgcgtgaaa   1140
tttagccgca gcgcggatgc gccggcgtat cagcagggcc agaaccagct gtataacgaa   1200
ctgaacctgg gccgccgcga agaatatgat gtgctggata acgccgcggc cgcgatccg   1260 gaaatgggcg gcaaaccgcg ccgcaaaaac ccgcaggaag gcctgtataa cgaactgcag   1320
aaagataaaa tggcggaagc gtatagcgaa attggcatga aggcgaacg ccgccgcggc   1380 aaaggccatg atggcctgta tcagggcctg agcaccgcga ccaaagatac ctatgatgcg   1440
ctgcatatgc aggcgctgcc gccgcgc                                      1467
```

<210> SEQ ID NO 10
<211> LENGTH: 489
<212> TYPE: PRT
<213> ORGANISM: Artificial Sequence
<220> FEATURE:
<223> OTHER INFORMATION: synthetic peptide

<400> SEQUENCE: 10

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220
```

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
            245                 250                 255

Gly Thr Ser Val Thr Val Ser Ser Ala Ala Ala Val Gly Phe Gln Asp
        260                 265                 270

Met Glu Cys Val Pro Cys Gly Asp Pro Pro Pro Tyr Glu Pro His
    275                 280                 285

Cys Ala Ser Lys Val Asn Leu Val Lys Ile Ala Ser Thr Ala Ser Ser
290                 295                 300

Pro Arg Asp Thr Ala Leu Ala Ala Val Ile Cys Ser Ala Leu Ala Thr
305                 310                 315                 320

Val Leu Leu Ala Leu Leu Ile Leu Cys Val Ile Tyr Cys Lys Arg Gln
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 11
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 11
atctacatct gggcgccctt ggccgggact tgtggggtcc ttctcctgtc actggttatc    60 acccttact gc                                                          72

<210> SEQ ID NO 12
<211> LENGTH: 22
<212> TYPE: PRT
<213> ORGANISM: Artificial Sequence
<220> FEATURE:
<223> OTHER INFORMATION: synthetic peptide

<400> SEQUENCE: 12

Ile Trp Ala Pro Leu Ala Glx Thr Cys Gly Val Leu Leu Leu Ser Leu
1               5                   10                  15

```
Val Ile Thr Leu Tyr Cys
            20
```

```
<210> SEQ ID NO 13
<211> LENGTH: 135
<212> TYPE: DNA
<213> ORGANISM: Artificial Sequence
<220> FEATURE:
<223> OTHER INFORMATION: synthetic oligonucleotide

<400> SEQUENCE: 13
accacgacgc cagcgccgcg accaccaaca ccggcgccca ccatcgcgtc gcagcccctg    60
tccctgcgcc agaggcgtg ccggccagcg gcgggggggcg cagtgcacac gagggggctg   120
gacttcgcct gtgat                                                    135
```

```
<210> SEQ ID NO 14
<211> LENGTH: 47
<212> TYPE: PRT
<213> ORGANISM: Artificial Sequence
<220> FEATURE:
<223> OTHER INFORMATION: synthetic peptide

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

```
<210> SEQ ID NO 15
<211> LENGTH: 42
<212> TYPE: PRT
<213> ORGANISM: Artificial Sequence
<220> FEATURE:
<223> OTHER INFORMATION: synthetic peptide

<400> SEQUENCE: 15

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 16
<211> LENGTH: 106
<212> TYPE: PRT
<213> ORGANISM: Artificial Sequence
<220> FEATURE:
<223> OTHER INFORMATION: synthetic peptide

<400> SEQUENCE: 16

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 17
<211> LENGTH: 126
<212> TYPE: DNA
<213> ORGANISM: Artificial Sequence
<220> FEATURE:
<223> OTHER INFORMATION: synthetic oligonucleotide

<400> SEQUENCE: 17
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 18
<211> LENGTH: 42
<212> TYPE: PRT
<213> ORGANISM: Artificial Sequence
<220> FEATURE:
<223> OTHER INFORMATION: synthetic peptide

<400> SEQUENCE: 18

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 19
<211> LENGTH: 336
<212> TYPE: DNA
<213> ORGANISM: Artificial Sequence
<220> FEATURE:
<223> OTHER INFORMATION: synthetic oligonucleotide

<400> SEQUENCE: 19
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca gggggcacga tggcctttac cagggtctca gtacagccac caaggacacc   300
tacgacgccc ttcacatgca ggccctgccc cctcgc                            336

<210> SEQ ID NO 20
<211> LENGTH: 112
<212> TYPE: PRT
<213> ORGANISM: Artificial Sequence
<220> FEATURE:
<223> OTHER INFORMATION: synthetic peptide

<400> SEQUENCE: 20

Arg Val Lys Phe Ser Arg Ser Ala Asp Ala Pro Ala Tyr Lys Gln Gly
1               5                   10                  15

```
Gln Asn Gln Leu Tyr Asn Glu Leu Asn Leu Gly Arg Arg Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110

<210> SEQ ID NO 21
<211> LENGTH: 1467
<212> TYPE: DNA
<213> ORGANISM: Artificial Sequence
<220> FEATURE:
<223> OTHER INFORMATION: synthetic oligonucleotide

<400> SEQUENCE: 21
atgctgctgc tggtgaccag cctgctgctg tgcgaactgc cgcatccggc gtttctgctg      60
attccggata ttcagatgac ccagaccacc agcagcctga gcgcgagcct gggcgatcgc     120
gtgaccatta gctgccgcgc gagccaggat attagcaaat atctgaactg gtatcagcag     180
aaaccggatg gcaccgtgaa actgctgatt tatcatacca gccgcctgca tagcggcgtg     240
ccgagccgct tagcggcag cggcagcggc accgattata gcctgaccat tagcaacctg     300
gaacaggaag atattgcgac ctatttttgc cagcagggca caccctgcc gtataccttt     360 ggcggcggca ccaaactgga aattaccggc ggcggcggca gcggcggcgg cggcagcggc     420
ggcggcggca gcgaagtgaa actgcaggaa agcggcccgg gcctggtggc gccgagccag     480
agcctgagcg tgacctgcac cgtgagcggc gtgagcctgc cggattatgg cgtgagctgg     540
attcgccagc cgccgcgcaa aggcctggaa tggctgggcg tgatttgggg cagcgaaacc     600
acctattata cagcgcgct gaaaagccgc ctgaccatta ttaaagataa cagcaaaagc     660
caggtgtttc tgaaaatgaa cagcctgcag accgatgata ccgcgattta ttattgcgcg     720
aaacattatt attatggcgg cagctatgcg atggattatt ggggccaggg caccagcgtg     780
accgtgagca gcgcggcggc gccggcgccg cgcccgccga cccggcgcc gaccattgcg     840 agccagccgc tgagcctgcg cccggaagcg tgccgcccgg cggcgggcgg cgcggtgcat     900
acccgcggcc tggattttgt gcagccgatg gcgctgattg tgctgggcgg cgtggcgggc     960
ctgctgctgt ttattggcct gggcattttt ttttgcgtgc gctgccgccc cgccgcaaa     1020 aaactgctgt atatttttaa acagccgttt atgcgcccgg tgcagaccac ccaggaagaa     1080
gatggctgca gctgccgctt tccggaagaa gaagaaggcg gctgcgaact ggcgtgaaa     1140 tttagccgca gcgcggatgc gccggcgtat cagcagggcc agaaccagct gtataacgaa     1200
ctgaacctgg gccgccgcga agaatatgat gtgctggata acgccgcgg ccgcgatccg     1260 gaaatgggcg gcaaaccgcg ccgcaaaaac ccgcaggaag gcctgtataa cgaactgcag     1320
aaagataaaa tggcggaagc gtatagcgaa attggcatga aaggcgaacg ccgccgcggc     1380
aaaggccatg atggcctgta tcagggcctg agcaccgcga ccaaagatac ctatgatgcg     1440
ctgcatatgc aggcgctgcc gccgcgc                                        1467
```

<210> SEQ ID NO 22
<211> LENGTH: 489
<212> TYPE: PRT
<213> ORGANISM: Artificial Sequence
<220> FEATURE:
<223> OTHER INFORMATION: synthetic peptide

<400> SEQUENCE: 22

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Val Gln Pro Met Ala Leu Ile Val Leu Gly Gly Val Ala Gly
305                 310                 315                 320

Leu Leu Leu Phe Ile Gly Leu Gly Ile Phe Phe Cys Val Arg Cys Arg
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
```

```
                370                375                380
Ala Asp Ala Pro Ala Tyr Gln Gln Gly Gln Asn Gln Leu Tyr Asn Glu
385                390                395                400

Leu Asn Leu Gly Arg Arg Glu Glu Tyr Asp Val Leu Asp Lys Arg Arg
                405                410                415

Gly Arg Asp Pro Glu Met Gly Gly Lys Pro Arg Arg Lys Asn Pro Gln
                420                425                430

Glu Gly Leu Tyr Asn Glu Leu Gln Lys Asp Lys Met Ala Glu Ala Tyr
                435                440                445

Ser Glu Ile Gly Met Lys Gly Glu Arg Arg Arg Gly Lys Gly His Asp
    450                455                460

Gly Leu Tyr Gln Gly Leu Ser Thr Ala Thr Lys Asp Thr Tyr Asp Ala
465                470                475                480

Leu His Met Gln Ala Leu Pro Pro Arg
                485

<210> SEQ ID NO 23
<211> LENGTH: 159
<212> TYPE: DNA
<213> ORGANISM: Artificial Sequence
<220> FEATURE:
<223> OTHER INFORMATION: synthetic oligonucleotide

<400> SEQUENCE: 23
ggcgattgcc tgccgggctt ttatcgcaaa accaaactgg tgggctttca ggatatggaa      60
tgcgtgccgt gcggcgatcc gccgccgccg tatgaaccgc attgcgcgag caaagtgaac     120
ctggtgaaaa ttgcgagcac cgcgagcagc ccgcgcgat                            159

<210> SEQ ID NO 24
<211> LENGTH: 53
<212> TYPE: PRT
<213> ORGANISM: Artificial Sequence
<220> FEATURE:
<223> OTHER INFORMATION: synthetic peptide

<400> SEQUENCE: 24

Gly Asp Cys Leu Pro Gly Phe Tyr Arg Lys Thr Lys Leu Val Gly Phe
1                5                10                15

Gln Asp Met Glu Cys Val Pro Cys Gly Asp Pro Pro Pro Pro Tyr Glu
                20                25                30

Pro His Cys Ala Ser Lys Val Asn Leu Val Lys Ile Ala Ser Thr Ala
            35                40                45

Ser Ser Pro Arg Asp
    50

<210> SEQ ID NO 25
<211> LENGTH: 186
<212> TYPE: DNA
<213> ORGANISM: Artificial Sequence
<220> FEATURE:
<223> OTHER INFORMATION: synthetic oligonucleotide

<400> SEQUENCE: 25
gaagaaattc cgggccgctg gattacccgc agcacccngc cggaaggcag cgatagcacc      60
gcgccgagca cccaggaacc ggaagcgccg ccggaacagg atctgattgc gagcaccgtg     120
gcgggcgtgg tgaccaccgt gatgggcagc agccagccgg tggtgacccg cggcaccacc     180
gataac                                                                186
```

<210> SEQ ID NO 26
<211> LENGTH: 62
<212> TYPE: PRT
<213> ORGANISM: Artificial Sequence
<220> FEATURE:
<223> OTHER INFORMATION: synthetic peptide

<400> SEQUENCE: 26

```
Glu Glu Ile Pro Gly Arg Trp Ile Thr Arg Ser Thr Pro Glu Gly
1               5                   10                  15

Ser Asp Ser Thr Ala Pro Ser Thr Gln Glu Pro Glu Ala Pro Pro Glu
            20                  25                  30

Gln Asp Leu Ile Ala Ser Thr Val Ala Gly Val Val Thr Thr Val Met
            35                  40                  45

Gly Ser Ser Gln Pro Val Val Thr Arg Gly Thr Thr Asp Asn
            50                  55                  60
```

<210> SEQ ID NO 27
<211> LENGTH: 726
<212> TYPE: DNA
<213> ORGANISM: Artificial Sequence
<220> FEATURE:
<223> OTHER INFORMATION: synthetic oligonucleotide

<400> SEQUENCE: 27

```
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat acactcagg agtcccatca      180
aggttcagtg gcagtgggtc tggaacagat tattctctca ccattagcaa cctggagcaa     240
gaagatattg ccacttactt tgccaacag ggtaatacgc ttccgtacac gttcggaggg      300
gggaccaagc tggagatcac aggtggcggt ggctcgggcg gtggtgggtc gggtggcggc    360
ggatctgagg tgaaactgca ggagtcagga cctggcctgg tggcgccctc acagagcctg     420
tccgtcacat gcactgtctc aggggtctca ttacccgact atggtgtaag ctggattcgc     480
cagcctccac gaaagggtct ggagtggctg gagtaatat ggggtagtga aaccacatac      540
tataattcag ctctcaaatc cagactgacc atcatcaagg acaactccaa gagccaagtt     600
ttcttaaaaa tgaacagtct gcaaactgat gacacagcca tttactactg tgccaaacat     660
tattactacg gtggtagcta tgctatggac tactggggcc aaggaacctc agtcaccgtc     720
tcctca                                                                726
```

<210> SEQ ID NO 28
<211> LENGTH: 242
<212> TYPE: PRT
<213> ORGANISM: Artificial Sequence
<220> FEATURE:
<223> OTHER INFORMATION: synthetic peptide

<400> SEQUENCE: 28

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
            50                  55                  60
```

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
210                 215                 220

Gly Ser Tyr Ala Met Asp Tyr Trp Gly Gln Gly Thr Ser Val Thr Val
225                 230                 235                 240

Ser Ser

<210> SEQ ID NO 29
<211> LENGTH: 1485
<212> TYPE: DNA
<213> ORGANISM: Artificial Sequence
<220> FEATURE:
<223> OTHER INFORMATION: synthetic oligonucleotide

<400> SEQUENCE: 29

```
atgctgctgc tggtgaccag cctgctgctg tgcgaactgc cgcatccggc gtttctgctg      60
attccggata ccgatattca gatgacccag accaccagca gcctgagcgc gagcctgggc     120
gatcgcgtga ccattagctg ccgcgcgagc caggatatta gcaaatatct gaactggtat     180
cagcagaaac cggatggcac cgtgaaactg ctgatttatc ataccagccg cctgcatagc     240
ggcgtgccga gccgctttag cggcagcggc agcggcaccg attatagcct gaccattagc     300
aacctggaac aggaagatat tgcgacctat ttttgccagc agggcaacac cctgccgtat     360 accttttggcg gcggcaccaa actggaaatt accggcagca ccagcggcag cggcaaaccg     420
ggcagcggcg aaggcagcac caaaggcgaa gtgaaactgc aggaaagcgg cccgggcctg     480
gtggcgccga gccagagcct gagcgtgacc tgcaccgtga gcggcgtgag cctgccggat     540
tatggcgtga gctggattcg ccagccgccg cgcaaaggcc tggaatggct gggcgtgatt     600
tggggcagcg aaaccaccta ttataacagc gcgctgaaaa gccgcctgac cattattaaa     660
gataacagca aaagccaggt gtttctgaaa atgaacagcc tgcagaccga tgataccgcg     720
atttattatt gcgcgaaaca ttattattat ggcggcagct atgcgatgga ttattgggc      780 cagggcacca gcgtgaccgt gagcagcgcg gcggcgacca ccaccccggc gccgcgcccg     840
ccgaccccgg cgccgaccat tgcgagccag ccgctgagcc tgcgcccgga agcgtgccgc     900
ccggcggcgg gcggcgcggt gcatacccgc ggcctggatt ttgcgtgcga tatttatatt     960
tgggcgccgc tggcgggcac ctgcggcgtg ctgctgctga gcctggtgat taccctgtat    1020
```

```
tgcaaacgcg gccgcaaaaa actgctgtat attttttaaac agccgtttat gcgcccggtg    1080
cagaccaccc aggaagaaga tggctgcagc tgccgctttc cggaagaaga agaaggcggc    1140
tgcgaactgc gcgtgaaatt tagccgcagc gcggatgcgc cggcgtatca gcagggccag    1200
aaccagctgt ataacgaact gaacctgggc cgccgcgaag aatatgatgt gctggataaa    1260
cgccgcggcc gcgatccgga atgggcggc aaaccgcgcc gcaaaaaccc gcaggaaggc    1320
ctgtataacg aactgcagaa agataaaatg gcggaagcgt atagcgaaat tggcatgaaa    1380
ggcgaacgcc gccgcggcaa aggccatgat ggcctgtatc agggcctgag caccgcgacc    1440
aaagatacct atgatgcgct gcatatgcag gcgctgccgc cgcgc                    1485
```

<210> SEQ ID NO 30
<211> LENGTH: 495
<212> TYPE: PRT
<213> ORGANISM: Artificial Sequence
<220> FEATURE:
<223> OTHER INFORMATION: synthetic peptide

<400> SEQUENCE: 30

```
Met Leu Leu Leu Val Thr Ser Leu Leu Cys Glu Leu Pro His Pro
1               5                   10                  15

Ala Phe Leu Leu Ile Pro Asp Thr Asp Ile Gln Met Thr Gln Thr Thr
                20                  25                  30

Ser Ser Leu Ser Ala Ser Leu Gly Asp Arg Val Thr Ile Ser Cys Arg
            35                  40                  45

Ala Ser Gln Asp Ile Ser Lys Tyr Leu Asn Trp Tyr Gln Gln Lys Pro
        50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
                100                 105                 110

Gln Gln Gly Asn Thr Leu Pro Tyr Thr Phe Gly Gly Gly Thr Lys Leu
            115                 120                 125

Glu Ile Thr Gly Ser Thr Ser Gly Ser Gly Lys Pro Gly Ser Gly Glu
        130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
                180                 185                 190

Gly Leu Glu Trp Leu Gly Val Ile Trp Gly Ser Glu Thr Thr Tyr Tyr
            195                 200                 205

Asn Ser Ala Leu Lys Ser Arg Leu Thr Ile Ile Lys Asp Asn Ser Lys
        210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Ala Ala Ala
            260                 265                 270

Thr Thr Thr Pro Ala Pro Arg Pro Pro Thr Pro Ala Pro Thr Ile Ala
```

|  |  |  | 275 |  |  |  | 280 |  |  |  | 285 |  |
|---|---|---|---|---|---|---|---|---|---|---|---|---|
| Ser | Gln | Pro | Leu | Ser | Leu | Arg | Pro | Glu | Ala | Cys | Arg | Pro | Ala | Ala | Gly |
|  |  |  | 290 |  |  |  | 295 |  |  |  | 300 |  |
| Gly | Ala | Val | His | Thr | Arg | Gly | Leu | Asp | Phe | Ala | Cys | Asp | Ile | Tyr | Ile |
| 305 |  |  |  |  | 310 |  |  |  |  | 315 |  |  |  |  | 320 |
| Trp | Ala | Pro | Leu | Ala | Gly | Thr | Cys | Gly | Val | Leu | Leu | Ser | Leu | Val |
|  |  |  |  | 325 |  |  |  |  | 330 |  |  |  |  | 335 |
| Ile | Thr | Leu | Tyr | Cys | Lys | Arg | Gly | Arg | Lys | Lys | Leu | Leu | Tyr | Ile | Phe |
|  |  |  | 340 |  |  |  | 345 |  |  |  | 350 |  |
| Lys | Gln | Pro | Phe | Met | Arg | Pro | Val | Gln | Thr | Thr | Gln | Glu | Glu | Asp | Gly |
|  |  |  | 355 |  |  |  | 360 |  |  |  | 365 |  |
| Cys | Ser | Cys | Arg | Phe | Pro | Glu | Glu | Glu | Glu | Gly | Gly | Cys | Glu | Leu | Arg |
|  | 370 |  |  |  |  | 375 |  |  |  |  | 380 |  |
| Val | Lys | Phe | Ser | Arg | Ser | Ala | Asp | Ala | Pro | Ala | Tyr | Gln | Gln | Gly | Gln |
| 385 |  |  |  |  | 390 |  |  |  |  | 395 |  |  |  |  | 400 |
| Asn | Gln | Leu | Tyr | Asn | Glu | Leu | Asn | Leu | Gly | Arg | Arg | Glu | Glu | Tyr | Asp |
|  |  |  |  | 405 |  |  |  |  | 410 |  |  |  |  | 415 |
| Val | Leu | Asp | Lys | Arg | Arg | Gly | Arg | Asp | Pro | Glu | Met | Gly | Gly | Lys | Pro |
|  |  |  | 420 |  |  |  | 425 |  |  |  | 430 |  |
| Arg | Arg | Lys | Asn | Pro | Gln | Glu | Gly | Leu | Tyr | Asn | Glu | Leu | Gln | Lys | Asp |
|  |  |  | 435 |  |  |  | 440 |  |  |  | 445 |  |
| Lys | Met | Ala | Glu | Ala | Tyr | Ser | Glu | Ile | Gly | Met | Lys | Gly | Glu | Arg | Arg |
|  | 450 |  |  |  |  | 455 |  |  |  |  | 460 |  |
| Arg | Gly | Lys | Gly | His | Asp | Gly | Leu | Tyr | Gln | Gly | Leu | Ser | Thr | Ala | Thr |
| 465 |  |  |  |  | 470 |  |  |  |  | 475 |  |  |  |  | 480 |
| Lys | Asp | Thr | Tyr | Asp | Ala | Leu | His | Met | Gln | Ala | Leu | Pro | Pro | Arg |
|  |  |  |  | 485 |  |  |  |  | 490 |  |  |  |  | 495 |

<210> SEQ ID NO 31
<211> LENGTH: 1470
<212> TYPE: DNA
<213> ORGANISM: Artificial Sequence
<220> FEATURE:
<223> OTHER INFORMATION: synthetic oligonucleotide

<400> SEQUENCE: 31

| atgctgctgc tggtgaccag cctgctgctg tgcgaactgc cgcatccggc gtttctgctg | 60 |
| attccggata ttcagatgac ccagaccacc agcagcctga cgcgagcct gggcgatcgc | 120 |
| gtgaccatta gctgccgcgc gagccaggat attagcaaat atctgaactg gtatcagcag | 180 |
| aaaccggatg gcaccgtgaa actgctgatt tatcatacca gccgcctgca tagcggcgtg | 240 |
| ccgagccgct ttagcggcag cggcagcggc accgattata gcctgaccat tagcaacctg | 300 |
| gaacaggaag atattgcgac ctattttgc cagcagggca cacccctgcc gtataccttt | 360 |
| ggcggcggca ccaaactgga aattaccggc ggcggcggca gcggcggcgg cggcagcggc | 420 |
| ggcggcggca gcgaagtgaa actgcaggaa agcggcccgg gcctggtggc gccgagccag | 480 |
| agcctgagcg tgacctgcac cgtgagcggc gtgagcctgc cggattatgg cgtgagctgg | 540 |
| attcgccagc cgccgcgcaa aggcctggaa tggctgggcg tgatttgggg cagcgaaacc | 600 |
| acctattata cagcgcgct gaaaagccgc ctgaccatta ttaaagataa cagcaaaagc | 660 |
| caggtgtttc tgaaaatgaa cagcctgcag accgatgata ccgcgattta ttattgcgcg | 720 |
| aaacattatt attatggcgg cagctatgcg atggattatt ggggccaggg caccagcgtg | 780 |
| accgtgagca gcgcggcggc gaccaccacc ccggcgccgc cccgccgac cccggcgccg | 840 |

-continued

| | | |
|---|---|---|
| accattgcga gccagccgct gagcctgcgc ccggaagcgt gccgcccggc ggcgggcggc | 900 | |
| gcggtgcata cccgcggcct ggattttgcg tgcgatattt atatttgggc gccgctggcg | 960 | |
| ggcacctgcg gcgtgctgct gctgagcctg gtgattaccc tgtattgcaa acgcggccgc | 1020 | |
| aaaaaactgc tgtatatttt taaacagccg tttatgcgcc cggtgcagac cacccaggaa | 1080 | |
| gaagatggct gcagctgccg ctttccggaa gaagaagaag gcggctgcga actgcgcgtg | 1140 | |
| aaatttagcc gcagcgcgga tgcgccggcg tatcagcagg ccagaaacca gctgtataac | 1200 | |
| gaactgaacc tgggccgccg cgaagaatat gatgtgctgg ataaacgccg cggccgcgat | 1260 | |
| ccggaaatgg gcggcaaacc gccgccgcaa aacccgcagg aaggcctgta taacgaactg | 1320 | |
| cagaaagata aaatggcgga agcgtatagc gaaattggca tgaaaggcga acgccgccgc | 1380 | |
| ggcaaaggcc atgatggcct gtatcagggc ctgagcaccg cgaccaaaga tacctatgat | 1440 | |
| gcgctgcata tgcaggcgct gccgccgcgc | 1470 | |

<210> SEQ ID NO 32
<211> LENGTH: 490
<212> TYPE: PRT
<213> ORGANISM: Artificial Sequence
<220> FEATURE:
<223> OTHER INFORMATION: synthetic peptide

<400> SEQUENCE: 32

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255
```

```
Gly Thr Ser Val Thr Val Ser Ala Ala Ala Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
                370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 33
<211> LENGTH: 1524
<212> TYPE: DNA
<213> ORGANISM: Artificial Sequence
<220> FEATURE:
<223> OTHER INFORMATION: synthetic oligonucleotide

<400> SEQUENCE: 33
atgggagccg agctactggg acgcgcaatg gacggaccga gactgctgct tctccttctg      60
ctgggcgtgt cccttggcgg tgccgatatc cagatgaccc agacaacctc gtccctgtcg     120
gccagcctgg gtgatcgcgt gaccatctcg tgccgcgcaa gccaggacat ctcaaagtat     180
ctgaactggt accaacaaaa gcccgacggg actgtgaagc tgctgatcta ccacacctcc     240
cgactccata gcggagtgcc aagccgattc tccggttccg gctctggaac cgattactcc     300
ctgaccatct ccaacctgga gcaggaggat attgccacct acttttgcca gcaggggaac     360
accctgccgt acactttcgg gggtggtact aagctggaaa tcaccggagg cggaggaagc     420
ggaggaggcg gttccggagg aggaggctca gaagtgaagc tgcaagaatc cggaccaggc     480
ttggtcgccc cctcccaaag cctgtcagtg acttgtaccg tgtcgggagt gtcgctgccc     540
gactacggcg tgtcctggat tagacagccg ccgagaaagg gcctgagtg gctgggtgtc     600 atttggggct ccgaaaccac ctactacaac agcccctca gtcacggct accatcatt       660 aaggacaact ccaagagcca agtgtttctc aagatgaaca gcctccagac cgacgacacc     720
```

-continued

```
gccatctact actgtgctaa gcactactac tacgggggct cctacgcaat ggactactgg    780
ggtcagggca ccagcgtgac cgtgtcctcc aagagatcc ctggcagatg gattacacgg    840
tctacgcctc ctgaaggctc ggactccact gccccgagca ctcaggaacc ggaagcccct   900
ccagaacagg acttgatcgc gagcactgtg gccggggtgg tcactactgt catgggatcg   960
tcccaacctg tggtgacccg ggtaccact gacaacctga tccccgtcta ctgctcgatt   1020
ctcgcagccg tcgtggtcgg cctggtggca tatatcgcat tcaagagggg ccggaagaag  1080
ctgctctaca tcttcaaaca accattcatg cggccggtgc agactaccca ggaggaggac  1140
ggatgttcgt gccgcttccc ggaagaggaa gagggcggat gcgaactgag agtcaagttc  1200
tcgagatcag cggatgcccc cgcttaccag cagggacaga atcagctcta taacgagctg  1260
aaccttggcc ggcgggaaga gtacgatgtg ctggataaga aagaggacg cgatcccgag   1320 atgggaggaa agcctcgccg gaagaacccg caggaaggcc tgtacaacga gcttcagaag  1380
gacaagatgg ccgaggccta ctccgaaatc ggaatgaagg gagaacgcag gcggggggaaa 1440 ggccacgatg ggctctacca gggtcttagc accgcgacca aggacaccta cgacgccctg  1500
catatgcaag cgcttcctcc acgc                                         1524
```

<210> SEQ ID NO 34
<211> LENGTH: 508
<212> TYPE: PRT
<213> ORGANISM: Artificial Sequence
<220> FEATURE:
<223> OTHER INFORMATION: synthetic peptide

<400> SEQUENCE: 34

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Asp Ile Gln Met
                20                  25                  30

Thr Gln Thr Thr Ser Ser Leu Ser Ala Ser Leu Gly Asp Arg Val Thr
            35                  40                  45

Ile Ser Cys Arg Ala Ser Gln Asp Ile Ser Lys Tyr Leu Asn Trp Tyr
        50                  55                  60

Gln Gln Lys Pro Asp Gly Thr Val Lys Leu Leu Ile Tyr His Thr Ser
65                  70                  75                  80

Arg Leu His Ser Gly Val Pro Ser Arg Phe Ser Gly Ser Gly Ser Gly
                85                  90                  95

Thr Asp Tyr Ser Leu Thr Ile Ser Asn Leu Glu Gln Glu Asp Ile Ala
            100                 105                 110

Thr Tyr Phe Cys Gln Gln Gly Asn Thr Leu Pro Tyr Thr Phe Gly Gly
        115                 120                 125

Gly Thr Lys Leu Glu Ile Thr Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
```

```
              210                 215                 220
Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Glu Glu
                260                 265                 270

Ile Pro Gly Arg Trp Ile Thr Arg Ser Thr Pro Glu Gly Ser Asp
                275                 280                 285

Ser Thr Ala Pro Ser Thr Gln Glu Pro Glu Ala Pro Pro Glu Gln Asp
290                 295                 300

Leu Ile Ala Ser Thr Val Ala Gly Val Val Thr Thr Val Met Gly Ser
305                 310                 315                 320

Ser Gln Pro Val Val Thr Arg Gly Thr Thr Asp Asn Leu Ile Pro Val
                325                 330                 335

Tyr Cys Ser Ile Leu Ala Ala Val Val Val Gly Leu Val Ala Tyr Ile
                340                 345                 350

Ala Phe Lys Arg Gly Arg Lys Lys Leu Leu Tyr Ile Phe Lys Gln Pro
                355                 360                 365

Phe Met Arg Pro Val Gln Thr Thr Gln Glu Glu Asp Gly Cys Ser Cys
                370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
                420                 425                 430

Lys Arg Arg Gly Arg Asp Pro Glu Met Gly Gly Lys Pro Arg Arg Lys
                435                 440                 445

Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
                500                 505

<210> SEQ ID NO 35
<211> LENGTH: 1422
<212> TYPE: DNA
<213> ORGANISM: Artificial Sequence
<220> FEATURE:
<223> OTHER INFORMATION: synthetic oligonucleotide

<400> SEQUENCE: 35
atggctctga aagtgctgtt ggaacaagaa aagaccttct tcaccttgct cgtgttgctg      60
gggtacctgt cctgcaaagt cacctgtgat atccagatga cccagacaac ctcgtccctg     120
tcggccagcc tgggtgatcg cgtgaccatc tcgtgccgcg caagccagga catctcaaag     180
tatctgaact ggtaccaaca aaagcccgac gggactgtga agctgctgat ctaccacacc     240
tcccgactcc atagcggagt gccaagccga ttctccggtt ccggctctgg aaccgattac     300
tccctgacca tctccaacct ggagcaggag gatattgcca cctactttg ccagcagggg     360 aacacccctg cgtacacttt cgggggtggt actaagctgg aaatcaccgg aggcggagga     420
```

```
agcggaggag gcggttccgg aggaggaggc tcagaagtga agctgcaaga atccggacca    480
ggcttggtcg ccccctccca aagcctgtca gtgacttgta ccgtgtcggg agtgtcgctg    540
cccgactacg gcgtgtcctg gattagacag ccgccgagaa agggcctgga gtggctgggt    600
gtcatttggg gctccgaaac cacctactac aacagcgccc tcaagtcacg gcttaccatc    660
attaaggaca actccaagag ccaagtgttt ctcaagatga acagcctcca gaccgacgac    720
accgccatct actactgtgc taagcactac tactacgggg ctcctacgc aatggactac    780
tggggtcagg gcaccagcgt gaccgtgtcc tcctacgagc tcactgcgc cagcaaagtc    840
aacttggtga gatcgcgag cactgcctcg tccctcggg acactgctct ggccgccgtc    900
atttgctcgg cgctcgcaac ggtcctgctg ccctgctca ttctgtgcgt gatctactgc    960
aagaggggcc ggaagaagct gctctacatc ttcaaacaac cattcatgcg gccggtgcag    1020
actacccagg aggaggacgg atgttcgtgc cgcttccgg aagaggaaga gggcggatgc    1080
gaactgagag tcaagttctc gagatcagcg gatgccccg cttaccagca gggacagaat    1140
cagctctata cgagctgaa ccttggccgg cgggaagagt acgatgtgct ggataagaga    1200
agaggacgcg atcccgagat gggaggaaag cctcgccgga agaacccgca ggaaggcctg    1260
tacaacgagc ttcagaagga caagatggcc gaggcctact ccgaaatcgg aatgaaggga    1320
gaacgcaggc gggggaaagg ccacgatggg ctctaccagg gtcttagcac cgcgaccaag    1380
gacacctacg acgccctgca tatgcaagcg cttcctccac gc                      1422

<210> SEQ ID NO 36
<211> LENGTH: 474
<212> TYPE: PRT
<213> ORGANISM: Artificial Sequence
<220> FEATURE:
<223> OTHER INFORMATION: synthetic peptide

<400> SEQUENCE: 36

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Asp Ile Gln
            20                  25                  30

Met Thr Gln Thr Thr Ser Ser Leu Ser Ala Ser Leu Gly Asp Arg Val
        35                  40                  45

Thr Ile Ser Cys Arg Ala Ser Gln Asp Ile Ser Lys Tyr Leu Asn Trp
    50                  55                  60

Tyr Gln Gln Lys Pro Asp Gly Thr Val Lys Leu Leu Ile Tyr His Thr
65                  70                  75                  80

Ser Arg Leu His Ser Gly Val Pro Ser Arg Phe Ser Gly Ser Gly Ser
                85                  90                  95

Gly Thr Asp Tyr Ser Leu Thr Ile Ser Asn Leu Glu Gln Glu Asp Ile
            100                 105                 110

Ala Thr Tyr Phe Cys Gln Gln Gly Asn Thr Leu Pro Tyr Thr Phe Gly
        115                 120                 125

Gly Gly Thr Lys Leu Glu Ile Thr Gly Gly Gly Gly Ser Gly Gly Gly
    130                 135                 140

Gly Ser Gly Gly Gly Gly Ser Glu Val Lys Leu Gln Glu Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
```

|     |     |     |     | 180 |     |     |     | 185 |     |     |     | 190 |     |
| --- | --- | --- | --- | --- | --- | --- | --- | --- | --- | --- | --- | --- | --- |
| Arg | Lys | Gly | Leu | Glu | Trp | Leu | Gly | Val | Ile | Trp | Gly | Ser | Glu | Thr | Thr |
|     |     |     |     |     | 195 |     |     |     |     | 200 |     |     |     |     | 205 |

Tyr Tyr Asn Ser Ala Leu Lys Ser Arg Leu Thr Ile Ile Lys Asp Asn
            210                215                    220

Ser Lys Ser Gln Val Phe Leu Lys Met Asn Ser Leu Gln Thr Asp Asp
225                     230                235                240

Thr Ala Ile Tyr Tyr Cys Ala Lys His Tyr Tyr Gly Gly Ser Tyr
                245                250                255

Ala Met Asp Tyr Trp Gly Gln Gly Thr Ser Val Thr Val Ser Ser Tyr
            260                265                270

Glu Pro His Cys Ala Ser Lys Val Asn Leu Val Lys Ile Ala Ser Thr
        275                280                285

Ala Ser Ser Pro Arg Asp Thr Ala Leu Ala Ala Val Ile Cys Ser Ala
        290                295                300

Leu Ala Thr Val Leu Leu Ala Leu Leu Ile Leu Cys Val Ile Tyr Cys
305                310                315                320

Lys Arg Gly Arg Lys Lys Leu Leu Tyr Ile Phe Lys Gln Pro Phe Met
                325                330                335

Arg Pro Val Gln Thr Thr Gln Glu Glu Asp Gly Cys Ser Cys Arg Phe
                340                345                350

Pro Glu Glu Glu Glu Gly Gly Cys Glu Leu Arg Val Lys Phe Ser Arg
            355                360                365

Ser Ala Asp Ala Pro Ala Tyr Gln Gln Gly Gln Asn Gln Leu Tyr Asn
        370                375                380

Glu Leu Asn Leu Gly Arg Arg Glu Glu Tyr Asp Val Leu Asp Lys Arg
385                390                395                400

Arg Gly Arg Asp Pro Glu Met Gly Gly Lys Pro Arg Arg Lys Asn Pro
                405                410                415

Gln Glu Gly Leu Tyr Asn Glu Leu Gln Lys Asp Lys Met Ala Glu Ala
            420                425                430

Tyr Ser Glu Ile Gly Met Lys Gly Glu Arg Arg Arg Gly Lys Gly His
            435                440                445

Asp Gly Leu Tyr Gln Gly Leu Ser Thr Ala Thr Lys Asp Thr Tyr Asp
        450                455                460

Ala Leu His Met Gln Ala Leu Pro Pro Arg
465                470

<210> SEQ ID NO 37
<211> LENGTH: 1476
<212> TYPE: DNA
<213> ORGANISM: Artificial Sequence
<220> FEATURE:
<223> OTHER INFORMATION: synthetic oligonucleotide

<400> SEQUENCE: 37

| atgggaaatt | cctgctacaa | catcgtcgcc | actctgctcc | tcgtgctgaa | cttcgagaga | 60 |
| actcgcagcg | atatccagat | gacccagaca | acctcgtccc | tgtcggccag | cctgggtgat | 120 |
| cgcgtgacca | tctcgtgccg | cgcaagccag | gacatctcaa | agtatctgaa | ctggtaccaa | 180 |
| caaaagcccg | acgggactgt | gaagctgctg | atctaccaca | cctcccgact | ccatagcgga | 240 |
| gtgccaagcc | gattctccgg | ttccggctct | ggaaccgatt | actccctgac | catctccaac | 300 |
| ctggagcagg | aggatattgc | cacctacttt | tgccagcagg | ggacacccct | gccgtacact | 360 |
| ttcggggggtg | gtactaagct | ggaaatcacc | ggaggcggag | gaagcggagg | aggcggttcc | 420 |

```
ggaggaggag gctcagaagt gaagctgcaa gaatccggac caggcttggt cgccccctcc    480
caaagcctgt cagtgacttg taccgtgtcg ggagtgtcgc tgcccgacta cggcgtgtcc    540
tggattagac agccgccgag aaagggcctg gagtggctgg gtgtcatttg gggctccgaa    600
accacctact acaacagcgc cctcaagtca cggcttacca tcattaagga caactccaag    660
agccaagtgt ttctcaagat gaacagcctc cagaccgacg acaccgccat ctactactgt    720
gctaagcact actactacgg gggctcctac gcaatggact actggggtca gggcaccagc    780
gtgaccgtgt cctccctgga tggcaaatcc gtgcttgtga acgggacgaa ggaaagggac    840
gtggtctgtg gaccgagccc ggccgacttg agcccaggcg cctcatccgt cactcccccct   900 gctcctgcac gggagcctgg tcacagcccc cagatcattt cgttcttcct cgcattgacc    960
tccactgccc tgctgttcct gctgttcttc ctgaccctgc ggttctcggt ggtcaagagg   1020
ggccggaaga agctgctcta catcttcaaa caaccattca tgcggccggt gcagactacc   1080
caggaggagg acggatgttc gtgccgcttc ccggaagagg aagagggcgg atgcgaactg   1140
agagtcaagt tctcgagatc agcggatgcc cccgcttacc agcagggaca gaatcagctc   1200
tataacgagc tgaaccttgg ccggcgggaa gagtacgatg tgctggataa gagaagagga   1260
cgcgatcccg agatgggagg aaagcctcgc cggaagaacc cgcaggaagg cctgtacaac   1320
gagcttcaga aggacaagat ggccgaggcc tactccgaaa tcggaatgaa gggagaacgc   1380
aggcggggga aaggccacga tgggctctac cagggtctta gcaccgcgac caaggacacc   1440
tacgacgccc tgcatatgca agcgcttcct ccacgc                             1476
```

<210> SEQ ID NO 38
<211> LENGTH: 492
<212> TYPE: PRT
<213> ORGANISM: Artificial Sequence
<220> FEATURE:
<223> OTHER INFORMATION: synthetic peptide

<400> SEQUENCE: 38

```
Met Gly Asn Ser Cys Tyr Asn Ile Val Ala Thr Leu Leu Val Leu
1               5                   10                  15

Asn Phe Glu Arg Thr Arg Ser Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Ile Thr Gly Gly Gly Gly Ser Gly Gly Gly Ser Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175
```

```
Tyr Gly Val Ser Trp Ile Arg Gln Pro Arg Lys Gly Leu Glu Trp
            180                 185                 190

Leu Gly Val Ile Trp Gly Ser Glu Thr Thr Tyr Tyr Asn Ser Ala Leu
        195                 200                 205

Lys Ser Arg Leu Thr Ile Ile Lys Asp Asn Ser Lys Ser Gln Val Phe
210                 215                 220

Leu Lys Met Asn Ser Leu Gln Thr Asp Thr Ala Ile Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Ser Val Thr Val Ser Leu Asp Gly Lys Ser Val Leu
            260                 265                 270

Val Asn Gly Thr Lys Glu Arg Asp Val Val Cys Gly Pro Ser Pro Ala
            275                 280                 285

Asp Leu Ser Pro Gly Ala Ser Ser Val Thr Pro Ala Pro Ala Arg
    290                 295                 300

Glu Pro Gly His Ser Pro Gln Ile Ile Ser Phe Phe Leu Ala Leu Thr
305                 310                 315                 320

Ser Thr Ala Leu Leu Phe Leu Leu Phe Phe Leu Thr Leu Arg Phe Ser
                325                 330                 335

Val Val Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 39
<211> LENGTH: 1467
<212> TYPE: DNA
<213> ORGANISM: Artificial Sequence
<220> FEATURE:
<223> OTHER INFORMATION: synthetic oligonucleotide

<400> SEQUENCE: 39
atgctgctgc tggtcaccag cctgctgctg tgcgagctcc ctcacccgc ctttctgctt      60 atcccggaca ttcagatgac acagaccacc tcgagcttgt ccgcgtcgct gggcgatcgc     120
gtgaccatct cctgccgggc ctcccaagac atttcaaagt atctcaactg gtaccagcag     180
aagccggacg gaaccgtgaa actgctgatc taccatacca gccgcctgca ctccggcgtg     240
```

```
ccgtcccgct tctccggatc gggttccgga actgactact cactgactat ctccaacttg    300
gaacaagagg acatcgccac ttacttctgt caacaaggaa ataccctccc ctacaccttc    360 gggggggta ccaagctgga gatcactggg ggcggaggct ccggtggagg cggatccggc    420
ggtggaggga gcgaagtcaa gctgcaggaa tcaggaccag gactcgtggc gccatcccag    480
tccctgtcgg tgacctgtac tgtctccgga gtcagcctcc ccgattacgg agtgtcatgg    540
attaggcaac ccccaagaaa agggctgaa tggctcggag tgatctgggg ctccgaaacc    600
acctactaca actcggcgct gaagtcccgg ctgaccatca tcaaggacaa ctccaagagc    660
caagtgttct tgaagatgaa cagcttgcag accgacgata ccgcaatcta ctactgtgcc    720
aagcactatt actacggggg gtcttacgcc atggactact ggggacaggg cacctccgtg    780
actgtgtcgt ccgcggccgc gcccgcccct cggcccccga ctcctgcccc gacgatcgct    840
tcccaacctc tctcgctgcg cccggaagca tgccggcccg ccgccggtgg cgctgtccac    900
actcgcggac tggactttgt gcagcctatg cactgatcg tcctgggagg agtggccgga    960
ctgctgctgt tcattgggct cggaatcttc ttctgcgtgc ggtgccggcc taggcgaaag   1020
aagctcctct acattttcaa gcaacccttc atgcgccccg tgcaaaccac ccaggaggag   1080
gatggatgct catgccggtt ccctgaggaa gaagagggcg gttgcgagct cagagtgaaa   1140
ttcagccggt cggctgacgc cccggcgtac cagcagggcc agaaccagct gtacaatgag   1200
ctcaacctgg ggcgccgcga agagtacgac gtgctggaca gaggagagg cagagatccg   1260 gaaatgggcg gaaagccaag gcggaagaac ccgcaggaag gtctttacaa cgaactgcag   1320
aaggacaaga tggccgaggc ctactccgag attgggatga aggagaaag acggaggga   1380 aagggacatg acggacttta ccagggcctg agcactgcca cgaaggacac ctatgatgcc   1440
ctgcacatgc aggcgctgcc gcctcgg                                      1467
```

<210> SEQ ID NO 40
<211> LENGTH: 1260
<212> TYPE: DNA
<213> ORGANISM: Artificial Sequence
<220> FEATURE:
<223> OTHER INFORMATION: synthetic oligonucleotide

<400> SEQUENCE: 40

```
atgctgctgc tggtcaccag cctgctgctg tgcgagctcc ctcacccgc ctttctgctt     60 atcccggaca ttcagatgac acagaccacc tcgagcttgt ccgcgtcgct gggcgatcgc    120
gtgaccatct cctgccgggc ctcccaagac atttcaaagt atctcaactg gtaccagcag    180
aagccggacg gaaccgtgaa actgctgatc taccatacca gccgcctgca ctccggcgtg    240
ccgtcccgct tctccggatc gggttccgga actgactact cactgactat ctccaacttg    300
gaacaagagg acatcgccac ttacttctgt caacaaggaa ataccctccc ctacaccttc    360 gggggggta ccaagctgga gatcactggg ggcggaggct ccggtggagg cggatccggc    420
ggtggaggga gcgaagtcaa gctgcaggaa tcaggaccag gactcgtggc gccatcccag    480
tccctgtcgg tgacctgtac tgtctccgga gtcagcctcc ccgattacgg agtgtcatgg    540
attaggcaac ccccaagaaa agggctgaa tggctcggag tgatctgggg ctccgaaacc    600
acctactaca actcggcgct gaagtcccgg ctgaccatca tcaaggacaa ctccaagagc    660
caagtgttct tgaagatgaa cagcttgcag accgacgata ccgcaatcta ctactgtgcc    720
aagcactatt actacggggg gtcttacgcc atggactact ggggacaggg cacctccgtg    780
actgtgtcgt ccgcggccgc gcccgcccct cggcccccga ctcctgcccc gacgatcgct    840
```

```
tcccaacctc tctcgctgcg cccggaagca tgccggcccg ccgccggtgg cgctgtccac    900
actcgcggac tggactttga taccgcactg gcggccgtga tctgtagcgc cctggccacc    960
gtgctgctgg cgctgctcat cctttgcgtg atctactgca agcggcagcc taggcgaaag   1020
aagctcctct acatttcaa gcaacccttc atgcgcccg tgcaaaccac ccaggaggag    1080
gatggatgct catgccggtt ccctgaggaa gaagagggcg gttgcgagct cagagtgaaa   1140
ttcagccggt cggctgacgc cccggcgtac cagcagggcc agaaccagct gtacaatgag   1200
ctcaacctgg ggcgccgcga agagtacgac gtgctggaca agaggagagg cagagatccg   1260
```

UNITED STATES PATENT AND TRADEMARK OFFICE
CERTIFICATE OF CORRECTION

PATENT NO.        : 10,421,810 B2
APPLICATION NO.   : 15/767076
DATED             : September 24, 2019
INVENTOR(S)       : Rimas Orentas, Dina Schneider and Boro Dropulic Page 1 of 1

It is certified that error appears in the above-identified patent and that said Letters Patent is hereby corrected as shown below:

In the Claims

Column 135, Line 30, Claim 3, delete "(Civil)." and insert -- (CML). --.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*